US012655208B1

(12) United States Patent
Kwan et al.

(10) Patent No.: US 12,655,208 B1
(45) Date of Patent: Jun. 16, 2026

(54) IL-23 BINDING PROTEIN COMPOSITIONS AND METHODS OF USE

(71) Applicant: Paragon Therapeutics, Inc., Waltham, MA (US)

(72) Inventors: Byron Hua Kwan, Waltham, MA (US); Hussam Hisham Shaheen, Vega Alta, PR (US); Gopalan Raghunathan, Santa Clara, CA (US)

(73) Assignee: Paragon Therapeutics, Inc., Waltham, MA (US)

( * ) Notice: Subject to any disclaimer, the term of this patent is extended or adjusted under 35 U.S.C. 154(b) by 0 days.

(21) Appl. No.: 19/274,134

(22) Filed: Jul. 18, 2025

Related U.S. Application Data

(63) Continuation of application No. PCT/US2025/014593, filed on Feb. 5, 2025.

(60) Provisional application No. 63/706,462, filed on Oct. 11, 2024, provisional application No. 63/697,429, filed on Sep. 20, 2024, provisional application No. 63/573,893, filed on Apr. 3, 2024, provisional application No. 63/573,721, filed on Apr. 3, 2024, provisional application No. 63/574,165, filed on Apr. 3, 2024, provisional application No. 63/573,741, filed on Apr. 3, 2024, provisional application No. 63/550,233, filed on Feb. 6, 2024, provisional application No. 63/550,110, filed on Feb. 6, 2024, provisional application No. 63/550,382, filed on Feb. 6, 2024.

(51) Int. Cl.
C07K 16/24 (2006.01)
A61K 39/00 (2006.01)

(52) U.S. Cl.
CPC ...... *C07K 16/244* (2013.01); *A61K 2039/505* (2013.01); *C07K 2317/24* (2013.01); *C07K 2317/76* (2013.01); *C07K 2317/92* (2013.01); *C07K 2317/94* (2013.01)

(58) Field of Classification Search
CPC .............. C07K 16/244; C07K 2317/24; C07K 2317/76; C07K 2317/92; C07K 2317/94; A61K 2039/505
See application file for complete search history.

(56) References Cited

U.S. PATENT DOCUMENTS

| | | |
|---|---|---|
| 7,872,102 B2 | 1/2011 | Beidler et al. |
| 8,012,476 B2 | 9/2011 | Dall'Acqua et al. |
| 8,778,346 B2 | 7/2014 | Barrett et al. |
| 9,441,036 B2 | 9/2016 | Barrett et al. |
| 10,059,763 B2 | 8/2018 | Barrett et al. |
| 10,202,448 B2 | 2/2019 | Barrett et al. |
| 10,280,231 B2 | 5/2019 | Singh et al. |
| 10,507,241 B2 | 12/2019 | Visvanathan et al. |
| 10,526,384 B2 | 1/2020 | Hinner et al. |
| 11,016,099 B2 | 5/2021 | Georgantas, III et al. |
| 11,028,166 B2 | 6/2021 | Cini et al. |
| 11,078,265 B2 | 8/2021 | Nabozny et al. |
| 11,168,134 B2 | 11/2021 | Alimonti et al. |
| 11,345,728 B2 | 5/2022 | Hinner et al. |
| 11,492,650 B2 | 11/2022 | Mandell et al. |
| 12,098,195 B2 | 9/2024 | Liu et al. |
| 12,319,742 B1 | 6/2025 | De Silva et al. |
| 2012/0121597 A1 | 5/2012 | Ho et al. |
| 2012/0282269 A1 | 11/2012 | Barrett et al. |
| 2016/0060338 A1 | 3/2016 | Barrett et al. |
| 2016/0222102 A1 | 8/2016 | Arndt et al. |
| 2016/0304602 A1 | 10/2016 | Arndt et al. |
| 2017/0022294 A1 | 1/2017 | Singh et al. |
| 2017/0081400 A1 | 3/2017 | Poulton et al. |
| 2017/0081402 A1 | 3/2017 | Boecher et al. |
| 2017/0298126 A1 | 10/2017 | Baum et al. |
| 2018/0105588 A1 | 4/2018 | Baum et al. |
| 2019/0048078 A1 | 2/2019 | Georgiou et al. |
| 2019/0144534 A1 | 5/2019 | Barrett et al. |
| 2020/0299378 A1 | 9/2020 | Baum et al. |
| 2020/0308271 A1 | 10/2020 | Baum et al. |
| 2020/0376117 A1 | 12/2020 | Visvanathan et al. |
| 2021/0032325 A1 | 2/2021 | Canavan et al. |
| 2021/0070852 A1 | 3/2021 | Garidel et al. |
| 2021/0115130 A1 | 4/2021 | Liu et al. |
| 2021/0198355 A1 | 7/2021 | Barrett et al. |
| 2021/0277105 A1 | 9/2021 | Gommoll et al. |
| 2021/0317201 A1 | 10/2021 | Nabozny et al. |
| 2022/0259301 A1 | 8/2022 | Wallace et al. |
| 2023/0159633 A1* | 5/2023 | Germinaro ................ A61P 1/04 424/158.1 |

(Continued)

FOREIGN PATENT DOCUMENTS

| | | |
|---|---|---|
| WO | 2012/061448 A1 | 5/2012 |
| WO | 2019/129261 A1 | 7/2019 |

(Continued)

OTHER PUBLICATIONS

Timmins P et al. Industry update: the latest developments in the field of therapeutic delivery, Apr. 2024 (Therapeutic Delivery 2024 15(9) 639-651). (Year: 2024).*
Prihoda D et al. BioPhi: A platform for antibody design, humanization, and humanness evaluation based on natural antibody repertoires and deep learning (MAbs. Feb. 8, 2022;14(1):2020203) (Year: 2022).*
Bertani et al., "Baseline Assessment of Serum Cytokines Predicts Clinical and Endoscopic Response to Ustekinumab in Patients With Crohn's Disease: A Prospective Pilot Study", Inflammatory Bowel Diseases, vol. 30, pp. 2449-2456, 2024.
Booth, B. et al., "Extending human IgG half-life using structure-guided design," MABS, vol. 10(7):1098-1110 (2018).

(Continued)

*Primary Examiner* — Karen A. Canella
*Assistant Examiner* — John J Skoko, III
(74) *Attorney, Agent, or Firm* — Greenberg Traurig, LLP; Sagar Antala; Prashant Girinath

(57) ABSTRACT

IL-23 binding proteins (e.g., antibodies) and methods of use, including methods of treating inflammatory bowel disease (e.g., ulcerative colitis or Crohn's disease) comprising administering IL-23 binding proteins.

20 Claims, 11 Drawing Sheets

Specification includes a Sequence Listing.

(56) References Cited

U.S. PATENT DOCUMENTS

| | | | |
|---|---|---|---|
| 2023/0173069 A1 | 6/2023 | Cao et al. | |
| 2023/0226095 A1 | 7/2023 | Chatila et al. | |
| 2024/0132558 A1 | 4/2024 | Bhandari et al. | |
| 2024/0141032 A1 | 5/2024 | Germinaro et al. | |
| 2024/0254217 A1 | 8/2024 | Krishnan et al. | |
| 2024/0391994 A1 | 11/2024 | Shan | |
| 2025/0034243 A1 | 1/2025 | Canavan et al. | |
| 2025/0101093 A1 | 3/2025 | Barrett et al. | |

FOREIGN PATENT DOCUMENTS

| | | |
|---|---|---|
| WO | 2023/064278 A2 | 4/2023 |
| WO | 2023051798 A1 | 4/2023 |
| WO | 2023/133538 A2 | 7/2023 |
| WO | 2023/241659 A1 | 12/2023 |
| WO | 2023244746 A1 | 12/2023 |
| WO | 2024/175031 A1 | 8/2024 |
| WO | 2024/178157 A1 | 8/2024 |
| WO | 2024/263900 A2 | 12/2024 |
| WO | 2025/071362 A1 | 4/2025 |
| WO | 2025/111585 A1 | 5/2025 |
| WO | 2025137347 A1 | 6/2025 |
| WO | 2025/144089 A1 | 7/2025 |
| WO | 2025/170982 A2 | 8/2025 |

OTHER PUBLICATIONS

Dall'Acqua, W. et al., "Properties of Human IgG1s Engineered for Enhanced Binding to the Neonatal Fc Receptor (FcRn)," The Journal of Biological Chemistry, vol. 281 ( 33): 23514-23524 (2006).

Danese et al., "Efficacy and safety of 48 weeks of guselkumab for patients with Crohn's disease: maintenance results from the phase 2, randomised, double-blind GALAXI-1 trial".

D'Haens et al., "Mirikizumab as Induction and Maintenance Therapy for Ulcerative Colitis", n. Engl. J. Med., vol. 388, No. 26, pp. 2444-2445, Jun. 29, 2023., vol. 399, pp. 2015-2030, 2022.

D'Haens et al., "Risankizumab as induction therapy for Crohn's disease: results from the phase 3 Advance and Motivate induction trials", Lancet, vol. 399, pp. 2015-2030, 2022.

Feagan et al., "Induction therapy with the selective interleukin-23 inhibitor risankizumab in patients with moderate-to-severe Crohn's disease: a randomised, double-blind, placebo-controlled phase 2 study", The Lancet, vol. 389, pp. 1699-1709, Apr. 29, 2017.

Ferrante et al., "Maintenance Risankizumab Sustains Induction Response in Patients with Crohn's Disease in a Randomized Phase 3 Trial", Manuscript Doi: 10.1093/ecco-jcc/jjad168, Oct. 15, 2023.

Ferrante et al., "Risankizumab as maintenance therapy for moderately to severely active Crohn's disease: results from the multicentre, randomised, double-blind, placebo-controlled, withdrawal phase 3 Fortify maintenance trial", Lancet, vol. 399, pp. 2031-2046, May 28, 2022.

Gros et al., "Guselkumab in the IL-23 inhibition landscape for ulcerative colitis", The Lancet, vol. 405, No. 10472, pp. 2-3, Jan. 4, 2025.

Kwan, B. et al., "Characterization of ORKA-001, a Novel Extended Half-life Monoclonal Antibody Targeting IL-23 for the Treatment of Psoriasis," EADV conference Jan. 17-20, 2025, Poster Presentation, 1 page.

Kwan, B. et al., "Characterization of ORKA-001, a Novel Extended Half-life Monoclonal Antibody Targeting IL-23 for the Treatment of Psoriasis," EADV conference Jan. 20-24, 2025, Poster Presentation, 1 page.

Kwan, B. et al., "Characterization of ORKA-001, a Novel Extended Half-life Monoclonal Antibody Targeting IL-23 for the Treatment of Psoriasis," EADV conference Oct. 24-27, Poster Presentation, 1 page.

Kwan, B. et al., "Characterization of ORKA-001, a Novel Extended Half-life Monoclonal An-tibody Targeting IL-23 for the Treatment of Psoriasis," EADV conference Sep. 25-28, 2024, P3283, 1 page.

Louis et al., "Risankizumab for Ulcerative Colitis Two Randomized Clinical Trials", JAMA, Original Investigation, JAMA, vol. 332, No. 11, pp. 881-897, 2024.

Louis et al., "Risankizumab Induction Therapy in Patients With Moderately to Severely Active Ulcerative Colitis: Efficacy and Safety in the Randomized Phase 3 Inspire Study", The American Journal of Gastroenterology, vol. 118, Supplement, pp. 1-2, Oct. 2023.

Papp et al., "Risankizumab versus Ustekinumab for Moderate-to-Severe Plaque Psoriasis", The New England Journal of Medicine, vol. 376, No. 16, pp. 1551-1560, Apr. 20, 2017.

Robbie, G. et al., "A Novel Investigational Fc-Modified Humanized Monoclonal Antibody, Motavizumab-YTE, Has an Extended Half-Life in Healthy Adults," Antimicrobial Agents and Chemotherapy, vol. 57(12): 6147-6153 (2013).

Rocca, A. et al., "Passive Immunoprophylaxis against Respiratory Syncytial Virus in Children: Where Are We Now?," Int. J. Mol. Sci.., vol. 22 (3703) 22 pages (2021).

Sandborn et al., "Efficacy and Safety of Mirikizumab in a Randomized Phase 2 Study of Patients With Ulcerative Colitis", Gastroentolgy, vol. 158, No. 3, pp. 537-549, Feb. 2020.

Steere, B. et al., "Generation and Characterization of Mirikizumab, a Humanized Monoclonal Antibody Targeting the p19 Subunit of IL-23", The Journal of Pharmacology and Experimental Therapeutics, vol. 387(2):180-187 (2023).

Suleiman et al., "Population Pharmacokinetic and Exposure—Response Analyses for Efficacy and Safety of Risankizumab in Patients With Active Crohn's Disease", Clinical Pharmacology & Therapeutics, vol. 113, No. 4, pp. 839-850, Apr. 2023.

Thakre et al., "Population Pharmacokinetic and Exposure-Response Modeling to Inform Risankizumab Dose Selection in Patients With Ulcerative Colitis", Clinical Pharmacology & Therapeutics, vol. 116 No. 3, ppl 847-857, Sep. 2024.

Zhuang et al., "First-in-human study to assess guselkumab (anti-IL-23 mAb) pharmacokinetics/safety in healthy subjects and patients with moderate-to-severe psoriasis", Eru. J. Clin. Pharmacol., vol. 72, pp. 1303-1310, 2016.

Zinger et al., "Risankizumab Effectiveness and Safety in Crohn's Disease: Real-world Data from a Large Tertiary Center", Clinical Gastroenterology and Hepatology, vol. 22, pp. 1336-1338, Jun. 2024.

International Search Report and Written Opinion, PCT/US2025/014593, dated Jun. 2, 2025, 17 pages.

Singh et al., "Selective targeting of the IL23 pathway: Generation and characterization of a novel high-affinity humanized anti-IL23A antibody", mAbs, vol. 7, Iss. 4, pp. 778-791, Jul. 2015.

Baeten et al., "IL-23 Inhibition in Ankylosing Spondylitis: Where Did It Go Wrong?", Front Immunol., vol. 11:623874, pp. 1-4, Feb. 18, 2021.

Blumberg et al., "Unraveling the Autoimmune Translational Research Process Layer by Layer", Nat. Med., vol. 18, No. 1, pp. 35-41, Jan. 6, 2012.

Kwan, B. et al., "Characterization of ORKA-001, a Novel Extended Half-life Monoclonal Antibody Targeting IL-23 for the Treatment of Psoriasis," EADV conference Oct. 24-27, 2024, Poster Presentation, 1 page.

Ma, "Animal Models of Disease", Modern Drug Discovery, vol. 7, No. 6, Jun. 2004.

McGonagle et al., "Why Inhibition of IL-23 Lacked Efficacy in Ankylosing Spondylitis", Front Immunol., vol. 12, Article 614255, pp. 1-9, Mar. 19, 2021.

Saunders, K., "Conceptual Approaches to Modulating Antibody Effector Functions and Circulation Half-Life," Frontiers in Immunology, vol. 10 (Article 1296): 20 pages (2019).

Steinman et al., "Optimization of Current and Future Therapy for Autoimmune Diseases", Nat. Med. vol. 18, No. 1, pp. 59-65, Jan. 6, 2012.

International Search Report and Written Opinion, PCT/US2024/034997, dated Jan. 21, 2025.

* cited by examiner

MAb002 epitope

Reference Antibody 1 epitope

SEQUENCE LISTING

Sequence total quantity: 174
SEQ ID NO: 1            moltype = AA   length = 120
FEATURE                 Location/Qualifiers -continued

```
source                    1..120
                          mol_type = protein
                          organism = synthetic construct
SEQUENCE: 1
QVQLVQSGAE VKKPGSSVKV SCKASGYTFT TQTLHWMRQA PGQGLEWIGY IYPRDGSTKY       60
NENFKGKVTI TADKSTSTAY MELSSLRSED TAVYYCAIPD RSGYAWFQHW GQGTLVTVSS      120

SEQ ID NO: 2              moltype = AA   length = 107
FEATURE                   Location/Qualifiers
source                    1..107
                          mol_type = protein
                          organism = synthetic construct
SEQUENCE: 2
DIQMTQSPSS LSASVGDRVT ITCKASRDVA IAVAWYQQKP GKVPKLLIYW ASTRHTGVPS       60
RFSGSGSRTD FTLTISSLQP EDVADYFCHQ YSSYPFTFGS GTKLEIK                    107

SEQ ID NO: 3              moltype = AA   length = 5
FEATURE                   Location/Qualifiers
source                    1..5
                          mol_type = protein
                          organism = synthetic construct
SEQUENCE: 3
TQTLH                                                                    5

SEQ ID NO: 4              moltype = AA   length = 17
FEATURE                   Location/Qualifiers
source                    1..17
                          mol_type = protein
                          organism = synthetic construct
SEQUENCE: 4
YIYPRDGSTK YNENFKG                                                      17

SEQ ID NO: 5              moltype = AA   length = 11
FEATURE                   Location/Qualifiers
source                    1..11
                          mol_type = protein
                          organism = synthetic construct
SEQUENCE: 5
PDRSGYAWFQ H                                                            11

SEQ ID NO: 6              moltype = AA   length = 11
FEATURE                   Location/Qualifiers
source                    1..11
                          mol_type = protein
                          organism = synthetic construct
SEQUENCE: 6
KASRDVAIAV A                                                            11

SEQ ID NO: 7              moltype = AA   length = 7
FEATURE                   Location/Qualifiers
source                    1..7
                          mol_type = protein
                          organism = synthetic construct
SEQUENCE: 7
WASTRHT                                                                  7

SEQ ID NO: 8              moltype = AA   length = 9
FEATURE                   Location/Qualifiers
source                    1..9
                          mol_type = protein
                          organism = synthetic construct
SEQUENCE: 8
HQYSSYPFT                                                                9

SEQ ID NO: 9              moltype = AA   length = 8
FEATURE                   Location/Qualifiers
source                    1..8
                          mol_type = protein
                          organism = synthetic construct
SEQUENCE: 9
GYTFTTQT                                                                 8

SEQ ID NO: 10             moltype = AA   length = 8
FEATURE                   Location/Qualifiers
source                    1..8
                          mol_type = protein
                          organism = synthetic construct
SEQUENCE: 10
IYPRDGST                                                                 8
```

-continued

```
SEQ ID NO: 11               moltype = AA   length = 13
FEATURE                     Location/Qualifiers
source                      1..13
                            mol_type = protein
                            organism = synthetic construct
SEQUENCE: 11
AIPDRSGYAW FQH                                                           13

SEQ ID NO: 12               moltype = AA   length = 6
FEATURE                     Location/Qualifiers
source                      1..6
                            mol_type = protein
                            organism = synthetic construct
SEQUENCE: 12
RDVAIA                                                                   6

SEQ ID NO: 13               moltype = AA   length = 7
FEATURE                     Location/Qualifiers
source                      1..7
                            mol_type = protein
                            organism = synthetic construct
SEQUENCE: 13
GYTFTTQ                                                                  7

SEQ ID NO: 14               moltype = AA   length = 6
FEATURE                     Location/Qualifiers
source                      1..6
                            mol_type = protein
                            organism = synthetic construct
SEQUENCE: 14
YPRDGS                                                                   6

SEQ ID NO: 15               moltype = AA   length = 9
FEATURE                     Location/Qualifiers
source                      1..9
                            mol_type = protein
                            organism = synthetic construct
SEQUENCE: 15
DRSGYAWFQ                                                                9

SEQ ID NO: 16               moltype = AA   length = 7
FEATURE                     Location/Qualifiers
source                      1..7
                            mol_type = protein
                            organism = synthetic construct
SEQUENCE: 16
SRDVAIA                                                                  7

SEQ ID NO: 17               moltype = AA   length = 6
FEATURE                     Location/Qualifiers
source                      1..6
                            mol_type = protein
                            organism = synthetic construct
SEQUENCE: 17
YSSYPF                                                                   6

SEQ ID NO: 18               moltype = AA   length = 120
FEATURE                     Location/Qualifiers
source                      1..120
                            mol_type = protein
                            organism = synthetic construct
SEQUENCE: 18
QVQLVQSGAE VKKPGSSVKV SCKASGYTFT SQTMHWMRQA PGQGLEWIGY IYPRDDYPKY 60
NDNFKGKVTI TADKSTSTAY MELSSLRSED TAVYYCAIPD RSGYAWFIHW GQGTLVTVSS 120

SEQ ID NO: 19               moltype = AA   length = 5
FEATURE                     Location/Qualifiers
source                      1..5
                            mol_type = protein
                            organism = synthetic construct
SEQUENCE: 19
SQTMH                                                                    5

SEQ ID NO: 20               moltype = AA   length = 17
FEATURE                     Location/Qualifiers
source                      1..17
                            mol_type = protein
                            organism = synthetic construct
```

-continued

```
SEQUENCE: 20
YIYPRDDYPK YNDNFKG                                                   17

SEQ ID NO: 21           moltype = AA  length = 11
FEATURE                 Location/Qualifiers
source                  1..11
                        mol_type = protein
                        organism = synthetic construct
SEQUENCE: 21
PDRSGYAWFI H                                                         11

SEQ ID NO: 22           moltype = AA  length = 8
FEATURE                 Location/Qualifiers
source                  1..8
                        mol_type = protein
                        organism = synthetic construct
SEQUENCE: 22
GYTFTSQT                                                             8

SEQ ID NO: 23           moltype = AA  length = 8
FEATURE                 Location/Qualifiers
source                  1..8
                        mol_type = protein
                        organism = synthetic construct
SEQUENCE: 23
IYPRDDYP                                                             8

SEQ ID NO: 24           moltype = AA  length = 13
FEATURE                 Location/Qualifiers
source                  1..13
                        mol_type = protein
                        organism = synthetic construct
SEQUENCE: 24
AIPDRSGYAW FIH                                                       13

SEQ ID NO: 25           moltype = AA  length = 7
FEATURE                 Location/Qualifiers
source                  1..7
                        mol_type = protein
                        organism = synthetic construct
SEQUENCE: 25
GYTFTSQ                                                              7

SEQ ID NO: 26           moltype = AA  length = 6
FEATURE                 Location/Qualifiers
source                  1..6
                        mol_type = protein
                        organism = synthetic construct
SEQUENCE: 26
YPRDDY                                                               6

SEQ ID NO: 27           moltype = AA  length = 9
FEATURE                 Location/Qualifiers
source                  1..9
                        mol_type = protein
                        organism = synthetic construct
SEQUENCE: 27
DRSGYAWFI                                                            9

SEQ ID NO: 28           moltype = AA  length = 120
FEATURE                 Location/Qualifiers
source                  1..120
                        mol_type = protein
                        organism = synthetic construct
SEQUENCE: 28
EVQLLESGGG LVQPGGSLRL SCAASGYTFT DQTIHWVRQA PGKGLEWIGY IYPRDDSPKY    60
NENFKGRATL SADNSKNTAY LQMNSLRAED TAVYYCAIPD RSGYAWFIYW GQGTTVTVSS    120

SEQ ID NO: 29           moltype = AA  length = 107
FEATURE                 Location/Qualifiers
source                  1..107
                        mol_type = protein
                        organism = synthetic construct
SEQUENCE: 29
EIVMTQSPAT LSVSPGERAT LSCKASRDVA IAVAWYQQKP GQAPRLLLFW ASTRHTGIPA    60
RFSGSGSRTE FTLTISSLQS EDFAVYYCHQ YSSYPFTFGG GTKVEIK                  107

SEQ ID NO: 30           moltype = AA  length = 5
FEATURE                 Location/Qualifiers
```

-continued

```
source                      1..5
                            mol_type = protein
                            organism = synthetic construct
SEQUENCE: 30
DQTIH                                                                    5

SEQ ID NO: 31               moltype = AA  length = 17
FEATURE                     Location/Qualifiers
source                      1..17
                            mol_type = protein
                            organism = synthetic construct
SEQUENCE: 31
YIYPRDDSPK YNENFKG                                                       17

SEQ ID NO: 32               moltype = AA  length = 11
FEATURE                     Location/Qualifiers
source                      1..11
                            mol_type = protein
                            organism = synthetic construct
SEQUENCE: 32
PDRSGYAWFI Y                                                             11

SEQ ID NO: 33               moltype = AA  length = 8
FEATURE                     Location/Qualifiers
source                      1..8
                            mol_type = protein
                            organism = synthetic construct
SEQUENCE: 33
GYTFTDQT                                                                 8

SEQ ID NO: 34               moltype = AA  length = 8
FEATURE                     Location/Qualifiers
source                      1..8
                            mol_type = protein
                            organism = synthetic construct
SEQUENCE: 34
IYPRDDSP                                                                 8

SEQ ID NO: 35               moltype = AA  length = 13
FEATURE                     Location/Qualifiers
source                      1..13
                            mol_type = protein
                            organism = synthetic construct
SEQUENCE: 35
AIPDRSGYAW FIY                                                           13

SEQ ID NO: 36               moltype = AA  length = 7
FEATURE                     Location/Qualifiers
source                      1..7
                            mol_type = protein
                            organism = synthetic construct
SEQUENCE: 36
GYTFTDQ                                                                  7

SEQ ID NO: 37               moltype = AA  length = 6
FEATURE                     Location/Qualifiers
source                      1..6
                            mol_type = protein
                            organism = synthetic construct
SEQUENCE: 37
YPRDDS                                                                   6

SEQ ID NO: 38               moltype = AA  length = 120
FEATURE                     Location/Qualifiers
source                      1..120
                            mol_type = protein
                            organism = synthetic construct
SEQUENCE: 38
QVQLVQSGAE VKKPGSSVKV SCKASGYTFT AQTMHWMRQA PGQGLEWIGY IYPRDGSTKY        60
NENFKGKVTI TADKSTSTAY MELSSLRSED TAVYYCAIPD RSGYAWFIVW GQGTLVTVSS       120

SEQ ID NO: 39               moltype = AA  length = 5
FEATURE                     Location/Qualifiers
source                      1..5
                            mol_type = protein
                            organism = synthetic construct
SEQUENCE: 39
AQTMH                                                                    5
```

-continued

```
SEQ ID NO: 40             moltype = AA  length = 11
FEATURE                   Location/Qualifiers
source                    1..11
                          mol_type = protein
                          organism = synthetic construct
SEQUENCE: 40
PDRSGYAWFI V                                                          11

SEQ ID NO: 41             moltype = AA  length = 8
FEATURE                   Location/Qualifiers
source                    1..8
                          mol_type = protein
                          organism = synthetic construct
SEQUENCE: 41
GYTFTAQT                                                              8

SEQ ID NO: 42             moltype = AA  length = 13
FEATURE                   Location/Qualifiers
source                    1..13
                          mol_type = protein
                          organism = synthetic construct
SEQUENCE: 42
AIPDRSGYAW FIV                                                        13

SEQ ID NO: 43             moltype = AA  length = 7
FEATURE                   Location/Qualifiers
source                    1..7
                          mol_type = protein
                          organism = synthetic construct
SEQUENCE: 43
GYTFTAQ                                                               7

SEQ ID NO: 44             moltype = AA  length = 329
FEATURE                   Location/Qualifiers
source                    1..329
                          mol_type = protein
                          organism = Homo sapiens
SEQUENCE: 44
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                      329

SEQ ID NO: 45             moltype = AA  length = 324
FEATURE                   Location/Qualifiers
source                    1..324
                          mol_type = protein
                          organism = Homo sapiens
SEQUENCE: 45
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSP                                           324

SEQ ID NO: 46             moltype = AA  length = 327
FEATURE                   Location/Qualifiers
source                    1..327
                          mol_type = protein
                          organism = Homo sapiens
SEQUENCE: 46
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                        327

SEQ ID NO: 47             moltype = AA  length = 327
FEATURE                   Location/Qualifiers
source                    1..327
                          mol_type = protein
                          organism = synthetic construct
SEQUENCE: 47
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV   120
```

```
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 48            moltype = AA   length = 327
FEATURE                  Location/Qualifiers
source                   1..327
                         mol_type = protein
                         organism = synthetic construct
SEQUENCE: 48
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEELGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327

SEQ ID NO: 49            moltype = AA   length = 329
FEATURE                  Location/Qualifiers
source                   1..329
                         mol_type = protein
                         organism = synthetic construct
SEQUENCE: 49
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKTHTC PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 50            moltype = AA   length = 329
FEATURE                  Location/Qualifiers
source                   1..329
                         mol_type = protein
                         organism = synthetic construct
SEQUENCE: 50
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP CPAPAPELLGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 51            moltype = AA   length = 329
FEATURE                  Location/Qualifiers
source                   1..329
                         mol_type = protein
                         organism = synthetic construct
SEQUENCE: 51
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP CPAPEAAGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 52            moltype = AA   length = 329
FEATURE                  Location/Qualifiers
source                   1..329
                         mol_type = protein
                         organism = synthetic construct
SEQUENCE: 52
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP CPAPELAGA  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 53            moltype = AA   length = 329
FEATURE                  Location/Qualifiers
source                   1..329
                         mol_type = protein
                         organism = synthetic construct
SEQUENCE: 53
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP CPAPEAAGA  120
PSVFLFPPKP KDTLMISRTP EVTCVVVDVS HEDPEVKFNW YVDGVEVHNA KTKPREEQYN  180
```

```
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 54              moltype = AA   length = 329
FEATURE                    Location/Qualifiers
source                     1..329
                           mol_type = protein
                           organism = synthetic construct
SEQUENCE: 54
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 55              moltype = AA   length = 329
FEATURE                    Location/Qualifiers
source                     1..329
                           mol_type = protein
                           organism = synthetic construct
SEQUENCE: 55
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 56              moltype = AA   length = 329
FEATURE                    Location/Qualifiers
source                     1..329
                           mol_type = protein
                           organism = synthetic construct
SEQUENCE: 56
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLYITREP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 57              moltype = AA   length = 329
FEATURE                    Location/Qualifiers
source                     1..329
                           mol_type = protein
                           organism = synthetic construct
SEQUENCE: 57
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLYITREP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 58              moltype = AA   length = 329
FEATURE                    Location/Qualifiers
source                     1..329
                           mol_type = protein
                           organism = synthetic construct
SEQUENCE: 58
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                      329

SEQ ID NO: 59              moltype = AA   length = 329
FEATURE                    Location/Qualifiers
source                     1..329
                           mol_type = protein
                           organism = synthetic construct
SEQUENCE: 59
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
```

```
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 60             moltype = AA  length = 329
FEATURE                   Location/Qualifiers
source                    1..329
                          mol_type = protein
                          organism = synthetic construct
SEQUENCE: 60
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 61             moltype = AA  length = 329
FEATURE                   Location/Qualifiers
source                    1..329
                          mol_type = protein
                          organism = synthetic construct
SEQUENCE: 61
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLYITREP EVTCVVVDVS HEDPEVKFNW YVDGVEVHNA KTKPREEQYN    180
STYRVVSVLT VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 62             moltype = AA  length = 329
FEATURE                   Location/Qualifiers
source                    1..329
                          mol_type = protein
                          organism = synthetic construct
SEQUENCE: 62
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                       329

SEQ ID NO: 63             moltype = AA  length = 329
FEATURE                   Location/Qualifiers
source                    1..329
                          mol_type = protein
                          organism = synthetic construct
SEQUENCE: 63
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                       329

SEQ ID NO: 64             moltype = AA  length = 329
FEATURE                   Location/Qualifiers
source                    1..329
                          mol_type = protein
                          organism = synthetic construct
SEQUENCE: 64
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                       329

SEQ ID NO: 65             moltype = AA  length = 329
FEATURE                   Location/Qualifiers
source                    1..329
                          mol_type = protein
                          organism = synthetic construct
SEQUENCE: 65
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
```

```
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                      329

SEQ ID NO: 66            moltype = AA  length = 329
FEATURE                  Location/Qualifiers
source                   1..329
                         mol_type = protein
                         organism = synthetic construct
SEQUENCE: 66
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                      329

SEQ ID NO: 67            moltype = AA  length = 329
FEATURE                  Location/Qualifiers
source                   1..329
                         mol_type = protein
                         organism = synthetic construct
SEQUENCE: 67
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                      329

SEQ ID NO: 68            moltype = AA  length = 329
FEATURE                  Location/Qualifiers
source                   1..329
                         mol_type = protein
                         organism = synthetic construct
SEQUENCE: 68
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHSHYT QKSLSLSPG                                      329

SEQ ID NO: 69            moltype = AA  length = 329
FEATURE                  Location/Qualifiers
source                   1..329
                         mol_type = protein
                         organism = synthetic construct
SEQUENCE: 69
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 70            moltype = AA  length = 329
FEATURE                  Location/Qualifiers
source                   1..329
                         mol_type = protein
                         organism = synthetic construct
SEQUENCE: 70
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 71            moltype = AA  length = 329
FEATURE                  Location/Qualifiers
source                   1..329
                         mol_type = protein
                         organism = synthetic construct
SEQUENCE: 71
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
```

```
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 72             moltype = AA  length = 329
FEATURE                   Location/Qualifiers
source                    1..329
                          mol_type = protein
                          organism = synthetic construct
SEQUENCE: 72
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 73             moltype = AA  length = 329
FEATURE                   Location/Qualifiers
source                    1..329
                          mol_type = protein
                          organism = synthetic construct
SEQUENCE: 73
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 74             moltype = AA  length = 329
FEATURE                   Location/Qualifiers
source                    1..329
                          mol_type = protein
                          organism = synthetic construct
SEQUENCE: 74
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 75             moltype = AA  length = 329
FEATURE                   Location/Qualifiers
source                    1..329
                          mol_type = protein
                          organism = synthetic construct
SEQUENCE: 75
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VDHHDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHSHYT QKSLSLSPG                                      329

SEQ ID NO: 76             moltype = AA  length = 327
FEATURE                   Location/Qualifiers
source                    1..327
                          mol_type = protein
                          organism = synthetic construct
SEQUENCE: 76
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV    120
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                       327

SEQ ID NO: 77             moltype = AA  length = 327
FEATURE                   Location/Qualifiers
source                    1..327
                          mol_type = protein
                          organism = synthetic construct
SEQUENCE: 77
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV    120
FLFPPKPKDT LYITREPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
```

-continued

```
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 78           moltype = AA  length = 327
FEATURE                 Location/Qualifiers
source                  1..327
                        mol_type = protein
                        organism = synthetic construct
SEQUENCE: 78
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEELGGPSV   120
FLFPPKPKDT LYITREPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 79           moltype = AA  length = 326
FEATURE                 Location/Qualifiers
source                  1..326
                        mol_type = protein
                        organism = synthetic construct
SEQUENCE: 79
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSYTQKSL SLSLGK                                        326

SEQ ID NO: 80           moltype = AA  length = 327
FEATURE                 Location/Qualifiers
source                  1..327
                        mol_type = protein
                        organism = synthetic construct
SEQUENCE: 80
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSYTQKS LSLSLGK                                        327

SEQ ID NO: 81           moltype = AA  length = 327
FEATURE                 Location/Qualifiers
source                  1..327
                        mol_type = protein
                        organism = synthetic construct
SEQUENCE: 81
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSYTQKS LSLSLGK                                        327

SEQ ID NO: 82           moltype = AA  length = 327
FEATURE                 Location/Qualifiers
source                  1..327
                        mol_type = protein
                        organism = synthetic construct
SEQUENCE: 82
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSYTQKS LSLSLGK                                        327

SEQ ID NO: 83           moltype = AA  length = 327
FEATURE                 Location/Qualifiers
source                  1..327
                        mol_type = protein
                        organism = synthetic construct
SEQUENCE: 83
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
```

-continued

```
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLGK                                      327

SEQ ID NO: 84            moltype = AA  length = 327
FEATURE                  Location/Qualifiers
source                   1..327
                         mol_type = protein
                         organism = synthetic construct
SEQUENCE: 84
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEELGGPSV   120
FLFPPKPKDT LMISRTPEVT CVVVDVSQED PEVQFNWYVD GVEVHNAKTK PREEQFNSTY   180
RVVSVLTVDH HDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHSHYTQKS LSLSLGK                                      327

SEQ ID NO: 85            moltype = AA  length = 324
FEATURE                  Location/Qualifiers
source                   1..324
                         mol_type = protein
                         organism = synthetic construct
SEQUENCE: 85
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL YITREPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVLHEA LHSHYTQKSL SLSP                                         324

SEQ ID NO: 86            moltype = AA  length = 324
FEATURE                  Location/Qualifiers
source                   1..324
                         mol_type = protein
                         organism = synthetic construct
SEQUENCE: 86
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSP                                         324

SEQ ID NO: 87            moltype = AA  length = 324
FEATURE                  Location/Qualifiers
source                   1..324
                         mol_type = protein
                         organism = synthetic construct
SEQUENCE: 87
ASTKGPSVFP LAPCSRSTSE STAALGCLVK DYFPEPVTVS WNSGALTSGV HTFPAVLQSS   60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVDHH DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHSHYTQKSL SLSP                                         324

SEQ ID NO: 88            moltype = AA  length = 327
FEATURE                  Location/Qualifiers
source                   1..327
                         mol_type = protein
                         organism = synthetic construct
SEQUENCE: 88
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPPCP APEFLGPSV    120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 89            moltype = AA  length = 329
FEATURE                  Location/Qualifiers
source                   1..329
                         mol_type = protein
                         organism = synthetic construct
SEQUENCE: 89
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
```

-continued

```
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 90            moltype = AA  length = 329
FEATURE                  Location/Qualifiers
source                   1..329
                         mol_type = protein
                         organism = synthetic construct
SEQUENCE: 90
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 91            moltype = AA  length = 329
FEATURE                  Location/Qualifiers
source                   1..329
                         mol_type = protein
                         organism = synthetic construct
SEQUENCE: 91
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 92            moltype = AA  length = 329
FEATURE                  Location/Qualifiers
source                   1..329
                         mol_type = protein
                         organism = synthetic construct
SEQUENCE: 92
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 93            moltype = AA  length = 329
FEATURE                  Location/Qualifiers
source                   1..329
                         mol_type = protein
                         organism = synthetic construct
SEQUENCE: 93
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 94            moltype = AA  length = 329
FEATURE                  Location/Qualifiers
source                   1..329
                         mol_type = protein
                         organism = synthetic construct
SEQUENCE: 94
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHAHYT QKSLSLSPG                                       329

SEQ ID NO: 95            moltype = AA  length = 329
FEATURE                  Location/Qualifiers
source                   1..329
                         mol_type = protein
                         organism = synthetic construct
SEQUENCE: 95
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
```

-continued

```
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHAHYT QKSLSLSPG                                     329

SEQ ID NO: 96               moltype = AA  length = 329
FEATURE                     Location/Qualifiers
source                      1..329
                            mol_type = protein
                            organism = synthetic construct
SEQUENCE: 96
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 97               moltype = AA  length = 329
FEATURE                     Location/Qualifiers
source                      1..329
                            mol_type = protein
                            organism = synthetic construct
SEQUENCE: 97
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 98               moltype = AA  length = 329
FEATURE                     Location/Qualifiers
source                      1..329
                            mol_type = protein
                            organism = synthetic construct
SEQUENCE: 98
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 99               moltype = AA  length = 329
FEATURE                     Location/Qualifiers
source                      1..329
                            mol_type = protein
                            organism = synthetic construct
SEQUENCE: 99
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 100              moltype = AA  length = 329
FEATURE                     Location/Qualifiers
source                      1..329
                            mol_type = protein
                            organism = synthetic construct
SEQUENCE: 100
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                     329

SEQ ID NO: 101              moltype = AA  length = 329
FEATURE                     Location/Qualifiers
source                      1..329
                            mol_type = protein
                            organism = synthetic construct
SEQUENCE: 101
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
```

```
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                      329

SEQ ID NO: 102            moltype = AA  length = 329
FEATURE                   Location/Qualifiers
source                    1..329
                          mol_type = protein
                          organism = synthetic construct
SEQUENCE: 102
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHAHYT QKSLSLSPG                                      329

SEQ ID NO: 103            moltype = AA  length = 329
FEATURE                   Location/Qualifiers
source                    1..329
                          mol_type = protein
                          organism = synthetic construct
SEQUENCE: 103
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                      329

SEQ ID NO: 104            moltype = AA  length = 329
FEATURE                   Location/Qualifiers
source                    1..329
                          mol_type = protein
                          organism = synthetic construct
SEQUENCE: 104
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                      329

SEQ ID NO: 105            moltype = AA  length = 329
FEATURE                   Location/Qualifiers
source                    1..329
                          mol_type = protein
                          organism = synthetic construct
SEQUENCE: 105
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                      329

SEQ ID NO: 106            moltype = AA  length = 329
FEATURE                   Location/Qualifiers
source                    1..329
                          mol_type = protein
                          organism = synthetic construct
SEQUENCE: 106
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHWHYT QKSLSLSPG                                      329

SEQ ID NO: 107            moltype = AA  length = 329
FEATURE                   Location/Qualifiers
source                    1..329
                          mol_type = protein
                          organism = synthetic construct
SEQUENCE: 107
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
```

-continued

```
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHWHYT QKSLSLSPG                                       329

SEQ ID NO: 108            moltype = AA   length = 329
FEATURE                   Location/Qualifiers
source                    1..329
                          mol_type = protein
                          organism = synthetic construct
SEQUENCE: 108
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGA     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHWHYT QKSLSLSPG                                       329

SEQ ID NO: 109            moltype = AA   length = 329
FEATURE                   Location/Qualifiers
source                    1..329
                          mol_type = protein
                          organism = synthetic construct
SEQUENCE: 109
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LGAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHWHYT QKSLSLSPG                                       329

SEQ ID NO: 110            moltype = AA   length = 329
FEATURE                   Location/Qualifiers
source                    1..329
                          mol_type = protein
                          organism = synthetic construct
SEQUENCE: 110
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG     120
PSVFLFPPKP KDTLMISRDP EVTCVVVDVS HEDPEVKFNW YVDGVEVHNA KTKPREEQYN     180
STYRVVSVLQ VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                       329

SEQ ID NO: 111            moltype = AA   length = 329
FEATURE                   Location/Qualifiers
source                    1..329
                          mol_type = protein
                          organism = synthetic construct
SEQUENCE: 111
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG     120
PSVFLFPPKP KDTLMISRDP EVTCVVVDVS HEDPEVKFNW YVDGVEVHNA KTKPREEQYA     180
STYRVVSVLQ VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                       329

SEQ ID NO: 112            moltype = AA   length = 329
FEATURE                   Location/Qualifiers
source                    1..329
                          mol_type = protein
                          organism = synthetic construct
SEQUENCE: 112
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG     120
PSVFLFPPKP KDTLMISRDP EVTCVVVAVS HEDPEVKFNW YVDGVEVHNA KTKPREEQYN     180
STYRVVSVLQ VLHQDWLNGK EYKCKVSNKA LPAPIEKTIS KAKGQPREPQ VYTLPPSRDE     240
LTKNQVSLTC LVKGFYPSDI AVEWESNGQP ENNYKTTPPV LDSDGSFFLY SKLTVDKSRW     300
QQGNVFSCSV MHEALHNHYT QKSLSLSPG                                       329

SEQ ID NO: 113            moltype = AA   length = 329
FEATURE                   Location/Qualifiers
source                    1..329
                          mol_type = protein
                          organism = synthetic construct
SEQUENCE: 113
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPEAAGG     120
PSVFLFPPKP KDTLMISRDP EVTCVVVDVS HEDPEVKFNW YVDGVEVHNA KTKPREEQYN     180
```

```
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 114          moltype = AA   length = 329
FEATURE                 Location/Qualifiers
source                  1..329
                        mol_type = protein
                        organism = synthetic construct
SEQUENCE: 114
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 115          moltype = AA   length = 329
FEATURE                 Location/Qualifiers
source                  1..329
                        mol_type = protein
                        organism = synthetic construct
SEQUENCE: 115
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 116          moltype = AA   length = 329
FEATURE                 Location/Qualifiers
source                  1..329
                        mol_type = protein
                        organism = synthetic construct
SEQUENCE: 116
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRDP EVTCVVVDVS HEDPEVKFNW YVDGVEVHNA KTKPREEQYN   180
STYRVVSVLQ VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 117          moltype = AA   length = 329
FEATURE                 Location/Qualifiers
source                  1..329
                        mol_type = protein
                        organism = synthetic construct
SEQUENCE: 117
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 118          moltype = AA   length = 329
FEATURE                 Location/Qualifiers
source                  1..329
                        mol_type = protein
                        organism = synthetic construct
SEQUENCE: 118
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVDVS HEDPEVKFNW YVDGVEVHNA KTKPREEQYA   180
STYRVVSVLW VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 119          moltype = AA   length = 329
FEATURE                 Location/Qualifiers
source                  1..329
                        mol_type = protein
                        organism = synthetic construct
SEQUENCE: 119
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRDP EVTCVVVAVS HEDPEVKFNW YVDGVEVHNA KTKPREEQYN   180
STYRVVSVLW VLHQDWLNGK EYKCKVSNKA LPAPIEKTIS KAKGQPREPQ VYTLPPSRDE   240
```

-continued

```
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 120              moltype = AA  length = 329
FEATURE                     Location/Qualifiers
source                      1..329
                            mol_type = protein
                            organism = synthetic construct
SEQUENCE: 120
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVHNA KTKPREEQYN    180
STYRVVSVLW VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 121              moltype = AA  length = 329
FEATURE                     Location/Qualifiers
source                      1..329
                            mol_type = protein
                            organism = synthetic construct
SEQUENCE: 121
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRDP EVTCVVVDVS HEDPEVKFNW YVDGVEVHNA KTKPREEQYN    180
STYRVVSVLW VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 122              moltype = AA  length = 329
FEATURE                     Location/Qualifiers
source                      1..329
                            mol_type = protein
                            organism = synthetic construct
SEQUENCE: 122
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRDP EVTCVVVDVS HEDPEVKFNW YVDGVEVHNA KTKPREEQYN    180
STYRVVSVLW VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 123              moltype = AA  length = 329
FEATURE                     Location/Qualifiers
source                      1..329
                            mol_type = protein
                            organism = synthetic construct
SEQUENCE: 123
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVHNA KTKPREEQYN    180
STYRVVSVLW VLHQDWLNGK EYKCKVSNKA LGAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 124              moltype = AA  length = 329
FEATURE                     Location/Qualifiers
source                      1..329
                            mol_type = protein
                            organism = synthetic construct
SEQUENCE: 124
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLYISRDP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                       329

SEQ ID NO: 125              moltype = AA  length = 329
FEATURE                     Location/Qualifiers
source                      1..329
                            mol_type = protein
                            organism = synthetic construct
SEQUENCE: 125
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
```

```
PSVFLFPPKP KDTLYISRDP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 126              moltype = AA   length = 329
FEATURE                     Location/Qualifiers
source                      1..329
                            mol_type = protein
                            organism = synthetic construct
SEQUENCE: 126
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLYISRDP EVTCVVVAVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 127              moltype = AA   length = 329
FEATURE                     Location/Qualifiers
source                      1..329
                            mol_type = protein
                            organism = synthetic construct
SEQUENCE: 127
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 128              moltype = AA   length = 329
FEATURE                     Location/Qualifiers
source                      1..329
                            mol_type = protein
                            organism = synthetic construct
SEQUENCE: 128
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELAGA   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 129              moltype = AA   length = 329
FEATURE                     Location/Qualifiers
source                      1..329
                            mol_type = protein
                            organism = synthetic construct
SEQUENCE: 129
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGA   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 130              moltype = AA   length = 329
FEATURE                     Location/Qualifiers
source                      1..329
                            mol_type = protein
                            organism = synthetic construct
SEQUENCE: 130
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPEAAGG   120
PSVFLFPPKP KDTLYISRDP EVTCVVVDVS HEDPEVKFNW YVDGVEVHNA KTKPREEQYN   180
STYRVVSVLT VLHQDWLNGK EYKCKVSNKA LGAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 131              moltype = AA   length = 329
FEATURE                     Location/Qualifiers
source                      1..329
                            mol_type = protein
                            organism = synthetic construct
SEQUENCE: 131
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
```

```
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 132              moltype = AA  length = 329
FEATURE                     Location/Qualifiers
source                      1..329
                            mol_type = protein
                            organism = synthetic construct
SEQUENCE: 132
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 133              moltype = AA  length = 329
FEATURE                     Location/Qualifiers
source                      1..329
                            mol_type = protein
                            organism = synthetic construct
SEQUENCE: 133
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 134              moltype = AA  length = 329
FEATURE                     Location/Qualifiers
source                      1..329
                            mol_type = protein
                            organism = synthetic construct
SEQUENCE: 134
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 135              moltype = AA  length = 329
FEATURE                     Location/Qualifiers
source                      1..329
                            mol_type = protein
                            organism = synthetic construct
SEQUENCE: 135
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELGG     120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 136              moltype = AA  length = 329
FEATURE                     Location/Qualifiers
source                      1..329
                            mol_type = protein
                            organism = synthetic construct
SEQUENCE: 136
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 137              moltype = AA  length = 329
FEATURE                     Location/Qualifiers
source                      1..329
                            mol_type = protein
                            organism = synthetic construct
SEQUENCE: 137
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLQ VLHVDWLNGK EYKCKVSNKA LGAPIEKTIS KAKGQPREPQ VYTLPPSRDE    240
```

```
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 138          moltype = AA  length = 329
FEATURE                 Location/Qualifiers
source                  1..329
                        mol_type = protein
                        organism = synthetic construct
SEQUENCE: 138
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRDP EVTCVVVDVS HEDPEVKFNW YVDGVEVDNA KTKPREEQYN    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 139          moltype = AA  length = 329
FEATURE                 Location/Qualifiers
source                  1..329
                        mol_type = protein
                        organism = synthetic construct
SEQUENCE: 139
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRDP EVTCVVVDVS HEDPEVKFNW YVDGVEVDNA KTKPREEQYA    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 140          moltype = AA  length = 329
FEATURE                 Location/Qualifiers
source                  1..329
                        mol_type = protein
                        organism = synthetic construct
SEQUENCE: 140
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRDP EVTCVVVAVS HEDPEVKFNW YVDGVEVDNA KTKPREEQYN    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 141          moltype = AA  length = 329
FEATURE                 Location/Qualifiers
source                  1..329
                        mol_type = protein
                        organism = synthetic construct
SEQUENCE: 141
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVDNA KTKPREEQYN    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 142          moltype = AA  length = 329
FEATURE                 Location/Qualifiers
source                  1..329
                        mol_type = protein
                        organism = synthetic construct
SEQUENCE: 142
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELAGA    120
PSVFLFPPKP KDTLMISRDP EVTCVVVDVS HEDPEVKFNW YVDGVEVDNA KTKPREEQYN    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                       329

SEQ ID NO: 143          moltype = AA  length = 329
FEATURE                 Location/Qualifiers
source                  1..329
                        mol_type = protein
                        organism = synthetic construct
SEQUENCE: 143
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA    120
```

-continued

```
PSVFLFPPKP KDTLMISRDP EVTCVVVDVS HEDPEVKFNW YVDGVEVDNA KTKPREEQYN    180
STYRVVSVLR VLHVDWLNGK EYKCKVSNKA LPAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 144            moltype = AA   length = 329
FEATURE                   Location/Qualifiers
source                    1..329
                          mol_type = protein
                          organism = synthetic construct
SEQUENCE: 144
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG    120
PSVFLFPPKP KDTLMISRDP EVTCVVVDVS HEDPEVKFNW YVDGVEVDNA KTKPREEQYN    180
STYRVVSVLR VLHVDWLNGK EYKCKVSNKA LGAPIEKTIS KAKGQPREPQ VYTLPPSRDE    240
LTKNQVSLTC LVKGFYPSDI VVEWESNGQP ENNYKTTPPV LDSDGSFFLY SKLTVDKSRW    300
QQGNVFSCSV MHEALHNHYT QKSLSLSPG                                      329

SEQ ID NO: 145            moltype = AA   length = 329
FEATURE                   Location/Qualifiers
source                    1..329
                          mol_type = protein
                          organism = synthetic construct
SEQUENCE: 145
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKDVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHRDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV LHEALHNHYT QKSLSLSPG                                      329

SEQ ID NO: 146            moltype = AA   length = 327
FEATURE                   Location/Qualifiers
source                    1..327
                          mol_type = protein
                          organism = synthetic construct
SEQUENCE: 146
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH RDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHNHYTQKS LSLSLGK                                       327

SEQ ID NO: 147            moltype = AA   length = 327
FEATURE                   Location/Qualifiers
source                    1..327
                          mol_type = protein
                          organism = synthetic construct
SEQUENCE: 147
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH RDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHNHYTQKS LSLSLGK                                       327

SEQ ID NO: 148            moltype = AA   length = 327
FEATURE                   Location/Qualifiers
source                    1..327
                          mol_type = protein
                          organism = synthetic construct
SEQUENCE: 148
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEELGGPSV    120
FLFPPKPKDT LMISRTPEVT CVVVDVSQED PEVQFNWYVD GVEVHNAKTK PREEQFNSTY    180
RVVSVLTVLH RDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVLHE ALHNHYTQKS LSLSLGK                                       327

SEQ ID NO: 149            moltype = AA   length = 324
FEATURE                   Location/Qualifiers
source                    1..324
                          mol_type = protein
                          organism = synthetic construct
SEQUENCE: 149
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
```

```
VVSVLTVVHR DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVLHEA LHNHYTQKSL SLSP                                         324

SEQ ID NO: 150            moltype = AA  length = 329
FEATURE                   Location/Qualifiers
source                    1..329
                          mol_type = protein
                          organism = synthetic construct
SEQUENCE: 150
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 151            moltype = AA  length = 329
FEATURE                   Location/Qualifiers
source                    1..329
                          mol_type = protein
                          organism = synthetic construct
SEQUENCE: 151
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVAVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 152            moltype = AA  length = 329
FEATURE                   Location/Qualifiers
source                    1..329
                          mol_type = protein
                          organism = synthetic construct
SEQUENCE: 152
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 153            moltype = AA  length = 329
FEATURE                   Location/Qualifiers
source                    1..329
                          mol_type = protein
                          organism = synthetic construct
SEQUENCE: 153
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELGA   120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 154            moltype = AA  length = 329
FEATURE                   Location/Qualifiers
source                    1..329
                          mol_type = protein
                          organism = synthetic construct
SEQUENCE: 154
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGA  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPG                                    329

SEQ ID NO: 155            moltype = AA  length = 329
FEATURE                   Location/Qualifiers
source                    1..329
                          mol_type = protein
                          organism = synthetic construct
SEQUENCE: 155
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVDVS HEDPEVKFNW YVDGVEVHNA KTKPREEQYN  180
STYRVVSVLT VLHRDWLNGK EYKCKVSNKA LGAPIEKTIS KAKGQPREPQ VYTLPPSRDE  240
```

```
LTKNQVSLTC LVKGFYPSDI AVEWESNGQP ENNYKTTPPV LDSDGSFFLY SKLTVDKSRW   300
QQGNVFSCSV LHEALHNHYT QKSLSLSPG                                     329

SEQ ID NO: 156            moltype = AA  length = 120
FEATURE                   Location/Qualifiers
source                    1..120
                          mol_type = protein
                          organism = synthetic construct
SEQUENCE: 156
QVQLVQSGAE VKKPGSSVKV SCKASGYTFT DQTIHWMRQA PGQGLEWIGY IYPRDDSPKY   60
NENFKGKVTI TADKSTSTAY MELSSLRSED TAVYYCAIPD RSGYAWFIYW GQGTLVTVSS   120

SEQ ID NO: 157            moltype = AA  length = 117
FEATURE                   Location/Qualifiers
source                    1..117
                          mol_type = protein
                          organism = synthetic construct
SEQUENCE: 157
EVQLVQSGAE VKKPGESLKI SCKGSGYSFS NYWIGWVRQM PGKGLEWMGI IDPSNSYTRY   60
SPSFQGQVTI SADKSISTAY LQWSSLKASD TAMYYCARWY YKPFDVWGQG TLVTVSS      117

SEQ ID NO: 158            moltype = AA  length = 111
FEATURE                   Location/Qualifiers
source                    1..111
                          mol_type = protein
                          organism = synthetic construct
SEQUENCE: 158
QSVLTQPPSV SGAPGQRVTI SCTGSSSNIG SGYDVHWYQQ LPGTAPKLLI YGNSKRPSGV   60
PDRFSGSKSG TSASLAITGL QSEDEADYYC ASWTDGLSLV VFGGGTKLTV L            111

SEQ ID NO: 159            moltype = AA  length = 5
FEATURE                   Location/Qualifiers
source                    1..5
                          mol_type = protein
                          organism = synthetic construct
SEQUENCE: 159
NYWIG                                                               5

SEQ ID NO: 160            moltype = AA  length = 17
FEATURE                   Location/Qualifiers
source                    1..17
                          mol_type = protein
                          organism = synthetic construct
SEQUENCE: 160
IIDPSNSYTR YSPSFQG                                                  17

SEQ ID NO: 161            moltype = AA  length = 8
FEATURE                   Location/Qualifiers
source                    1..8
                          mol_type = protein
                          organism = synthetic construct
SEQUENCE: 161
WYYKPFDV                                                            8

SEQ ID NO: 162            moltype = AA  length = 14
FEATURE                   Location/Qualifiers
source                    1..14
                          mol_type = protein
                          organism = synthetic construct
SEQUENCE: 162
TGSSSNIGSG YDVH                                                     14

SEQ ID NO: 163            moltype = AA  length = 7
FEATURE                   Location/Qualifiers
source                    1..7
                          mol_type = protein
                          organism = synthetic construct
SEQUENCE: 163
GNSKRPS                                                             7

SEQ ID NO: 164            moltype = AA  length = 11
FEATURE                   Location/Qualifiers
source                    1..11
                          mol_type = protein
                          organism = synthetic construct
SEQUENCE: 164
ASWTDGLSLV V                                                        11

SEQ ID NO: 165            moltype = AA  length = 450
```

-continued

```
FEATURE                 Location/Qualifiers
source                  1..450
                        mol_type = protein
                        organism = synthetic construct
SEQUENCE: 165
QVQLVQSGAE VKKPGSSVKV SCKASGYTFT TQTLHWMRQA PGQGLEWIGY IYPRDGSTKY   60
NENFKGKVTI TADKSTSTAY MELSSLRSED TAVYYCAIPD RSGYAWFQHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 166         moltype = AA  length = 214
FEATURE                 Location/Qualifiers
source                  1..214
                        mol_type = protein
                        organism = synthetic construct SEQUENCE: 166
DIQMTQSPSS LSASVGDRVT ITCKASRDVA IAVAWYQQKP GKVPKLLIYW ASTRHTGVPS   60
RFSGSGSRTD FTLTISSLQP EDVADYFCHQ YSSYPFTFGS GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 167         moltype = AA  length = 450
FEATURE                 Location/Qualifiers
source                  1..450
                        mol_type = protein
                        organism = synthetic construct
SEQUENCE: 167
QVQLVQSGAE VKKPGSSVKV SCKASGYTFT AQTMHWMRQA PGQGLEWIGY IYPRDGSTKY   60
NENFKGKVTI TADKSTSTAY MELSSLRSED TAVYYCAIPD RSGYAWFIVW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 168         moltype = AA  length = 214
FEATURE                 Location/Qualifiers
source                  1..214
                        mol_type = protein
                        organism = synthetic construct SEQUENCE: 168
EIVMTQSPAT LSVSPGERAT LSCKASRDVA IAVAWYQQKP GQAPRLLLFW ASTRHTGIPA   60
RFSGSGSRTE FTLTISSLQS EDFAVYYCHQ YSSYPFTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 169         moltype = AA  length = 450
FEATURE                 Location/Qualifiers
source                  1..450
                        mol_type = protein
                        organism = synthetic construct
SEQUENCE: 169
QVQLVQSGAE VKKPGSSVKV SCKASGYTFT SQTMHWMRQA PGQGLEWIGY IYPRDDYPKY   60
NDNFKGKVTI TADKSTSTAY MELSSLRSED TAVYYCAIPD RSGYAWFIHW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 170         moltype = AA  length = 214
FEATURE                 Location/Qualifiers
source                  1..214
                        mol_type = protein
                        organism = synthetic construct SEQUENCE: 170
DIQMTQSPSS LSASVGDRVT ITCKASRDVA IAVAWYQQKP GKVPKLLIYW ASTRHTGVPS   60
RFSGSGSRTD FTLTISSLQP EDVADYFCHQ YSSYPFTFGS GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 171         moltype = AA  length = 450
FEATURE                 Location/Qualifiers
```

-continued

```
source                    1..450
                          mol_type = protein
                          organism = synthetic construct
SEQUENCE: 171
EVQLLESGGG LVQPGGSLRL SCAASGYTFT DQTIHWVRQA PGKGLEWIGY IYPRDDSPKY   60
NENFKGRATL SADNSKNTAY LQMNSLRAED TAVYYCAIPD RSGYAWFIYW GQGTTVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPEAAGG  240
PSVFLFPPKP KDTLYITREP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 172          moltype = AA  length = 214
FEATURE                 Location/Qualifiers
source                  1..214
                        mol_type = protein
                        organism = synthetic construct
SEQUENCE: 172
EIVMTQSPAT LSVSPGERAT LSCKASRDVA IAVAWYQQKP GQAPRLLLFW ASTRHTGIPA   60
RFSGSGSRTE FTLTISSLQS EDFAVYYCHQ YSSYPFTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 173          moltype = AA  length = 449
FEATURE                 Location/Qualifiers
source                  1..449
                        mol_type = protein
                        organism = synthetic construct
SEQUENCE: 173
QVQLVQSGAE VKKPGSSVKV SCKASGYTFT DQTIHWMRQA PGQGLEWIGY IYPRDDSPKY   60
NENFKGKVTI TADKSTSTAY MELSSLRSED TAVYYCAIPD RSGYAWFIYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                   449

SEQ ID NO: 174          moltype = AA  length = 214
FEATURE                 Location/Qualifiers
source                  1..214
                        mol_type = protein
                        organism = synthetic construct
SEQUENCE: 174
DIQMTQSPSS LSASVGDRVT ITCKASRDVA IAVAWYQQKP GKVPKLLIYW ASTRHTGVPS   60
RFSGSGSRTD FTLTISSLQP EDVADYFCHQ YSSYPFTFGG GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214
```

IL-23 BINDING PROTEIN COMPOSITIONS AND METHODS OF USE

CROSS REFERENCE TO RELATED APPLICATIONS

This application is a continuation of International Application No. PCT/US25/14593, filed Feb. 5, 2025, which claims the benefit of and priority to U.S. Provisional Application No. 63/550,110, filed Feb. 6, 2024, U.S. Provisional Application No. 63/550,233, filed Feb. 6, 2024, U.S. Provisional Application No. 63/550,382, filed Feb. 6, 2024, U.S. Provisional Application No. 63/573,721, filed Apr. 3, 2024, U.S. Provisional Application No. 63/573,741, filed Apr. 3, 2024, U.S. Provisional Application No. 63/573,893, filed Apr. 3, 2024, U.S. Provisional Application No. 63/574,165, filed Apr. 3, 2024, U.S. Provisional Application No. 63/697,429, filed Sep. 20, 2024, and U.S. Provisional Application No. 63/706,462, filed Oct. 11, 2024, the entire contents of each of which are incorporated herein by reference.

SEQUENCE LISTING

This application contains a Sequence Listing which has been submitted electronically in XML format and is hereby incorporated by reference in its entirety. The XML copy, created on Jul. 18, 2025, is titled 220703-010912_US_SL.xml and is 191,674 bytes in size.

BACKGROUND

Interleukin-23 (IL-23) is a key inflammatory cytokine that promotes the differentiation of T helper 17 cells, leading to production of other cytokines such as interleukin-17. IL-23 plays a role in inflammatory diseases, and disorders such as inflammatory bowel disease (IBD).

IBD affects the digestive system but can also cause problems in other parts of the body. One type of IBD is Crohn's disease, which can cause symptoms anywhere in the digestive system. The other main form of IBD, ulcerative colitis, affects the large intestine (colon). IBD can be managed with a combination of medications, surgery, and lifestyle changes, but there is no known cure.

Current treatments for IBD include biologics such as IL-23 antibodies. Due to the importance of IL-23 in mediating pro-inflammatory responses, a need remains for development of additional inhibitors targeting IL-23. Additionally, dosing regimens for many currently used biologics typically include frequent dosing, requiring an injection every couple weeks (e.g., every four to eight weeks). A need remains for improved methods of treatment of IBD.

SUMMARY

The present disclosure addresses this need with the provision of IL-23 binding proteins, such as anti-IL-23 antibodies, and with methods of treating conditions such as inflammatory bowel disease (IBD), ulcerative colitis and/or Crohn's disease.

In one aspect, the disclosure provides an IL-23 binding protein comprising a heavy chain variable domain (VH) comprising complementarity-determining regions (CDRs): CDR-H1 comprising the amino acid sequence of SEQ ID NO: 3; CDR-H2 comprising the amino acid sequence of SEQ ID NO: 4; and CDR-H3 comprising the amino acid sequence of SEQ ID NO: 5 In some embodiments, the VH comprises an amino acid sequence that is at least 85% identical to that of SEQ ID NO: 1. In some embodiments, the IL-23 binding protein further comprising a light chain variable domain (VL) comprising complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8. In some embodiments, the VL comprises an amino acid sequence that is at least 85% identical to that of SEQ ID NO: 2.

In another aspect, the disclosure provides an IL-23 binding protein comprising (i) a heavy chain variable domain (VH) comprising complementarity-determining regions: CDR-H1 comprising the amino acid sequence of SEQ ID NO: 3; CDR-H2 comprising the amino acid sequence of SEQ ID NO: 4; and CDR-H3 comprising the amino acid sequence of SEQ ID NO: 5; and (ii) a light chain variable domain (VL) comprising complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8. In some embodiments, the disclosure provides an IL-23 binding protein comprising a heavy chain variable domain comprising an amino acid sequence according to SEQ ID NO: 1 and a light chain variable domain comprising an amino acid sequence according to SEQ ID NO: 2.

In some embodiments, the IL-23 binding protein is an anti-IL-23 antibody comprising a heavy chain comprising an amino acid sequence according to SEQ ID NO: 165, and a light chain comprising an amino acid sequence according to SEQ ID NO: 166.

In certain embodiments, the IL-23 binding protein is capable of inhibiting activation of STAT3 in human embryonic kidney (HEK) cells expressing IL-23Rat a relative $IC_{50}$ of less than 0.90, less than 0.80, less than 0.70, or less than 0.65 or at a relative $IC_{50}$ of from about 0.6 to about 0.65. In some embodiments, the IL-23 binding protein is capable of inhibiting phosphorylation of STAT3 in DB cells at a relative $IC_{50}$ reference of less than 0.80, less than 0.70, less than 0.60, or less than 0.58, or at a relative $IC_{50}$ of from about 0.55 to about 0.6.

In one aspect, the disclosure provides an IL-23 binding protein comprising a heavy chain variable domain (VH) comprising complementarity-determining regions: CDR-H1 comprising the amino acid sequence of SEQ ID NO: 19; CDR-H2 comprising the amino acid sequence of SEQ ID NO: 20; and CDR-H3 comprising the amino acid sequence of SEQ ID NO: 21. In some embodiments, the VH comprises an amino acid sequence that is at least 85% identical to that of SEQ ID NO: 18.

In certain embodiments, the IL-23 binding protein further comprises a light chain variable domain (VL) comprising complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8. In some embodiments, the VL comprises an amino acid sequence that is at least 85% identical to that of SEQ ID NO: 2.

In one aspect, the disclosure provides an IL-23 binding protein comprising (i) a heavy chain variable domain (VH) comprising complementarity-determining regions: CDR-H1 comprising the amino acid sequence of SEQ ID NO: 19; CDR-H2 comprising the amino acid sequence of SEQ ID NO: 20; and CDR-H3 comprising the amino acid sequence of SEQ ID NO: 21; and (ii) a light chain variable domain (VL) comprising complementarity-determining regions:

CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8.

In some embodiments, the disclosure provides an IL-23 binding protein comprising a heavy chain variable domain comprising an amino acid sequence according to SEQ ID NO: 18 and a light chain variable domain comprising an amino acid sequence according to SEQ ID NO: 2.

In some embodiments, the IL-23 binding protein is an anti-IL-23 antibody comprising a heavy chain comprising an amino acid sequence according to SEQ ID NO: 169, and a light chain comprising an amino acid sequence according to SEQ ID NO: 170.

In some embodiments, the IL-23 binding protein is capable of inhibiting activation of STAT3 in human embryonic kidney (HEK) cells expressing IL-23R at a relative $IC_{50}$ of less than 0.95, less than 0.90, or less than 0.88, or at a relative $IC_{50}$ of from about 0.85 to about 0.9. In some embodiments, the IL-23 binding protein is capable of inhibiting phosphorylation of STAT3 in DB cells at a relative $IC_{50}$ of less than 0.95, less than 0.90, or less than 0.85, or at a relative $IC_{50}$ of from about 0.75 to about 0.85.

In one aspect, the disclosure provides an IL-23 binding protein comprising (a) a heavy chain variable domain (VH) comprising (1) an amino acid sequence that is at least 85% identical to that of SEQ ID NO: 28, and (2) an asparagine at position 74 of SEQ ID NO: 28; and (b) a light chain variable domain (VL) comprising: (1) an amino acid sequence that is at least 85% identical to that of SEQ ID NO: 29, and (2) a phenylalanine at position 49 of SEQ ID NO: 29, wherein (i) the VH comprises complementarity-determining regions: CDR-H1 comprising the amino acid sequence of SEQ ID NO: 30; CDR-H2 comprising the amino acid sequence of SEQ ID NO: 31; and CDR-H3 comprising the amino acid sequence of SEQ ID NO: 32; and (ii) the VL comprises complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8. In an embodiment, the amino acid at position 27 of SEQ ID NO: 28 is not asparagine. In a further embodiment, the amino acid at position 27 of SEQ ID NO: 28 is a tyrosine. In another embodiment, the amino acid at position 74 of SEQ ID NO: 28 is not lysine. In another embodiment, the amino acid at position 49 of SEQ ID NO: 29 is not a tyrosine.

In some embodiments, the heavy chain variable domain further comprises one or more of the following: glutamic acid at position 1, leucine at position 5, glutamic acid at position 6, glycine at position 9, glycine at position 10, leucine at position 11, valine at position 12, glutamine at position 13, glycine at position 16, leucine at position 18, arginine at position 19, leucine at position 20, alanine at position 23, valine at position 37, lysine at position 43, arginine at position 67, leucine a position 70, serine at position 71, alanine at position 68, lysine at position 76, asparagine at position 77, leucine at position 81, glutamine at position 82, methionine at position 83, asparagine at position 84, alanine a position 88, or threonine at position 115 of SEQ ID NO: 28. In some embodiments, the light chain variable domain comprises one or more of the following: glutamic acid at position 1, valine at position 3, alanine at position 9, threonine at position 10, valine at position 13, proline at position 15, glutamic acid at position 17, alanine at position 19, leucine at position 21, serine at position 22, glutamine at position 42, alanine at position 43, arginine at position 45, leucine at position 48, isoleucine at position 58, alanine at position 60, glutamic acid at position 70, serine at position 80, phenylalanine at position 83, valine at position 85, tyrosine at position 87, glycine at position 100 or valine at position 104 of SEQ ID NO: 29.

In some embodiments, the VH comprises an amino acid sequence that is at least 90% identical to that of SEQ ID NO: 28, and the VL comprises an amino acid sequence that is at least 90% identical to that of SEQ ID NO: 29. In some embodiments, the VH comprises an amino acid sequence that is at least 92.5% identical to that of SEQ ID NO: 28, and the VL comprises an amino acid sequence that is at least 92.5% identical to that of SEQ ID NO: 29. In some embodiments, the VH comprises an amino acid sequence that is at least 95% identical to that of SEQ ID NO: 28, and the VL comprises an amino acid sequence that is at least 95% identical to that of SEQ ID NO: 29. In some embodiments, the VH comprises an amino acid sequence that is at least 98% identical to that of SEQ ID NO: 28, and the VL comprises an amino acid sequence that is at least 98% identical to that of SEQ ID NO: 29. In some embodiments, the disclosure provides an IL-23 binding protein comprising a VH comprising the amino acid sequence of SEQ ID NO: 28, and a VL comprising the amino acid sequence of SEQ ID NO: 29.

In some embodiments, the IL-23 binding protein is an anti-IL-23 antibody comprising a heavy chain comprising an amino acid sequence according to SEQ ID NO: 171, and a light chain comprising an amino acid sequence according to SEQ ID NO: 172.

In some embodiments, the IL-23 binding protein is capable of inhibiting activation of STAT3 in human embryonic kidney (HEK) cells expressing IL-23R at a relative $IC_{50}$ of less than 0.9, less than 0.8, less than 0.7, or at a relative $IC_{50}$ of from about 0.6 to about 0.7.

In another aspect, the disclosure provides an IL-23 binding protein comprising: (a) a heavy chain variable domain (VH) comprising (1) an amino acid sequence that is at least 85% identical to that of SEQ ID NO: 38 and (2) complementarity-determining regions: CDR-H1 comprising the amino acid sequence of SEQ ID NO: 39; CDR-H2 comprising the amino acid sequence of SEQ ID NO: 4; and CDR-H3 comprising the amino acid sequence of SEQ ID NO: 40; and (b) a light chain variable domain (VL) comprising (1) an amino acid sequence that is at least 85% identical to that of SEQ ID NO: 29; (2) a phenylalanine residue at position 49 of SEQ ID NO: 29, and (3) complementarity-determining regions: (i) CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8.

In some embodiments, the light chain variable domain further comprises one or more of the following: glutamic acid at position 1, valine at position 3, alanine at position 9, threonine at position 10, valine at position 13, proline at position 15, glutamic acid at position 17, alanine at position 19, leucine at position 21, serine at position 22, glutamine at position 42, alanine at position 43, arginine at position 45, leucine at position 48, isoleucine at position 58, alanine at position 60, glutamic acid at position 70, serine at position 80, phenylalanine at position 83, valine at position 85, tyrosine at position 87, glycine at position 100 or valine at position 104 of SEQ ID NO: 29

In some embodiments, the disclosure provides an IL-23 binding protein comprising a VH comprising the amino acid sequence of SEQ ID NO: 38, and a VL comprising the amino acid sequence of SEQ ID NO: 29.

In some embodiments, the IL-23 binding protein is an anti-IL-23 antibody comprising a heavy chain comprising an amino acid sequence according to SEQ ID NO: 167; and a light chain comprising an amino acid sequence according to SEQ ID NO: 168.

In some embodiments, the IL-23 binding protein is capable of inhibiting activation of STAT3 in human embryonic kidney (HEK) cells expressing IL-23R at a relative $IC_{50}$ of less than 0.90, less than 0.80, less than 0.70, less than 0.60, less than 0.50, or less than 0.45, or at a relative $IC_{50}$ of from about 0.35 to about 0.45.

In some embodiments, an IL-23 binding protein of the disclosure is an antibody or antigen-binding fragment thereof. In some embodiments, the IL-23 binding protein is a human antibody or antigen-binding fragment thereof. In some embodiments, the antigen binding fragment is a Fab, a F(ab')₂, a Fab', a single-chain Fv (scFv), an Fv fragment, a Fd fragment, or a diabody. In some embodiments, the antibody or antigen binding fragment thereof comprises an Fc region. In some such embodiments, the Fc region is a human IgG1, IgG2, or IgG4 Fc region. In some embodiments, the Fc region is a modified Fc region. For example, in some embodiments, the modified Fc region comprises a half-life extending modification or set of modifications. In some embodiments, the Fc region comprises amino acid modifications that result in an extended half-life are M252Y, S254T, and T256E (YTE) and/or M428L and N434S (LS).

In some embodiments, the disclosure provides an isolated nucleic acid encoding an IL-23 binding protein as provided herein. In some embodiments, the disclosure provides an expression vector comprising the isolated nucleic acid. In some embodiments, the disclosure provides a host cell comprising the isolated nucleic acid or the expression vector.

In some embodiments, the disclosure provides a composition comprising an IL-23 binding protein as provided herein and a pharmaceutically acceptable carrier.

In some embodiments, the disclosure provides a method of treating a disease or condition in a subject, comprising a step of administering to the subject an effective amount of an IL-23 binding protein or composition as provided herein. In some embodiments, the disease or condition is an inflammatory condition. In some embodiments, the disease or condition is a gastrointestinal inflammatory disease. In some embodiments, the disease or condition is inflammatory bowel disease. In some embodiments, the disease or condition is Crohn's disease. In some embodiments, the disease or condition is ulcerative colitis. In some embodiments, the method comprises administering intravenously or subcutaneously the effective amount of an IL-23 binding protein or composition as provided herein.

In one aspect, the disclosure provides a method of treating a gastrointestinal inflammatory disease in a subject in need thereof, the method comprising administering to the subject a maintenance dose of an IL-23 binding protein every 8 weeks or more for a period of time sufficient to treat or ameliorate inflammatory bowel disease. In some embodiments, the method comprises administering the maintenance dose every 3 months, every 12-13 weeks, every 6 months, every 24-26 weeks, twice a year, every 12 months, every 48-52 weeks, or once a year.

In some embodiments, the IL-23 binding protein comprising: (1) a VH comprising CDR-H1 comprising the amino acid sequence of SEQ ID NO: 3; CDR-H2 comprising the amino acid sequence of SEQ ID NO: 4; and CDR-H3 comprising the amino acid sequence of SEQ ID NO: 5; and (2) a modified Fc region that extends half-life of the IL-23 binding protein as compared to an IL-23 binding protein that does not comprise the modified Fc region. In some embodiments, the Fc region comprises amino acid modifications M252Y, S254T, and T256E (YTE) and/or M428L and N434S (LS). In some embodiments, the VH comprises an amino acid sequence that is at least 85% identical to that of SEQ ID NO: 1.

In some embodiments, the IL-23 binding protein further comprises a VL comprising CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8. In some embodiments, the VL comprises an amino acid sequence that is at least 85% identical to that of SEQ ID NO: 2.

In some embodiments, the IL-23 binding protein comprises: (1) (i) a heavy chain variable domain (VH) comprising complementarity-determining regions: CDR-H1 comprising the amino acid sequence of SEQ ID NO: 3; CDR-H2 comprising the amino acid sequence of SEQ ID NO: 4; and CDR-H3 comprising the amino acid sequence of SEQ ID NO: 5; and (ii) a light chain variable domain (VL) comprising complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8; and (2) a modified Fc region that extends half-life of the IL-23 binding protein as compared to an IL-23 binding protein that does not comprise the modified Fc region. In some embodiments, the Fc region comprises amino acid modifications M252Y, S254T, and T256E (YTE) and/or M428L and N434S (LS).

In some embodiments, the IL-23 binding protein comprises: (1) a heavy chain variable domain (VH) comprising complementarity-determining regions: (a) CDR-H1 comprising the amino acid sequence of SEQ ID NO: 19; CDR-H2 comprising the amino acid sequence of SEQ ID NO: 20; and CDR-H3 comprising the amino acid sequence of SEQ ID NO: 21; and (2) a modified Fc region that extends half-life of the IL-23 binding protein as compared to an IL-23 binding protein that does not comprise the modified Fc region. In some embodiments, the Fc region comprises amino acid modifications M252Y, S254T, and T256E (YTE) and/or M428L and N434S (LS).

In some embodiments, the VH comprises an amino acid sequence that is at least 85% identical to that of SEQ ID NO: 18.

In some embodiments, the IL-23 binding protein further comprises a VL comprising CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8.

In some embodiments, the VL comprises an amino acid sequence that is at least 85% identical to that of SEQ ID NO: 2.

In some embodiments, the IL-23 binding protein comprising: (1) (i) a VH comprising CDR-H1 comprising the amino acid sequence of SEQ ID NO: 19; CDR-H2 comprising the amino acid sequence of SEQ ID NO: 20; and CDR-H3 comprising the amino acid sequence of SEQ ID NO: 21; and (ii) a VL comprising: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8; and (2) a modified Fc region that extends half-life of the IL-23 binding protein as compared to an IL-23 binding protein that does not comprise the modified Fc region. In some embodiments, the Fc region comprises amino acid modifications M252Y, S254T, and T256E (YTE) and/or M428L and N434S (LS).

In some embodiments, the IL-23 binding protein comprising: (a) a VH comprising (1) an amino acid sequence that is at least 85% identical to that of SEQ ID NO: 28, and (2) an asparagine residue at position 74 of SEQ ID NO: 28; (b) a VL comprising: (1) an amino acid sequence that is at least 85% identical to that of SEQ ID NO: 29, and (2) a phenylalanine residue at position 49 of SEQ ID NO: 29; and (c) a modified Fc region that extends half-life of the IL-23 binding protein as compared to an IL-23 binding protein that does not comprise the modified Fc region, wherein (1) (i) the VH comprises CDR-H1 comprising the amino acid sequence of SEQ ID NO: 30; CDR-H2 comprising the amino acid sequence of SEQ ID NO: 31; and CDR-H3 comprising the amino acid sequence of SEQ ID NO: 32; and (ii) the VL comprises CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8 In some embodiments, the Fc region comprises amino acid modifications M252Y, S254T, and T256E (YTE) and/or M428L and N434S (LS). In an embodiment, the amino acid at position 27 of SEQ ID NO: 28 is not asparagine. In a further embodiment, the amino acid at position 27 of SEQ ID NO: 28 is a tyrosine. In another embodiment, the amino acid at position 74 of SEQ ID NO: 28 is not lysine. In another embodiment, the amino acid at position 49 of SEQ ID NO: 29 is not tyrosine.

In some embodiments, the IL-23 binding protein comprising: (a) VH) comprising (1) an amino acid sequence that is at least 85% identical to that of SEQ ID NO: 38 and (2) complementarity-determining regions: CDR-H1 comprising the amino acid sequence of SEQ ID NO: 39; CDR-H2 comprising the amino acid sequence of SEQ ID NO: 4; and CDR-H3 comprising the amino acid sequence of SEQ ID NO: 40; (b) a light chain variable domain (VL) comprising (1) an amino acid sequence that is at least 85% identical to that of SEQ ID NO: 29, (2) a phenylalanine residue at position 49 of SEQ ID NO: 29, and (3) complementarity-determining regions: CDR-L1 comprising the amino acid sequence of SEQ ID NO: 6; CDR-L2 comprising the amino acid sequence of SEQ ID NO: 7; and CDR-L3 comprising the amino acid sequence of SEQ ID NO: 8; and (c) a modified Fc region that extends half-life of the IL-23 binding protein as compared to an IL-23 binding protein that does not comprise the modified Fc region. In some embodiments, the Fc region comprises amino acid modifications M252Y, S254T, and T256E (YTE) and/or M428L and N434S (LS).

In certain embodiments, the maintenance dose of IL-23 the binding protein is at least about 150 mg, about 300 mg, about 600 mg, about 900 mg, or about 1200 mg. In some embodiments, prior to the step of administering maintenance doses, the subject has received an induction dose or doses of the IL-23 binding protein. In some embodiments, the induction dose of the IL-23 binding protein contains about twice the amount of IL-23 binding protein as the maintenance dose, and the induction dose is administered one, two, or three times. In some embodiments, the induction dose of the IL-23 binding protein contains two partial doses, each partial dose having the same amount of the IL-23 binding protein as the maintenance dose, and each two partial doses administered four weeks apart from each other. In some embodiments, the method comprises administering to the subject an induction dose as a single dose, two doses or three doses, before the administration of a first maintenance dose, and administering a maintenance dose no more frequently than every 3 months or every 12-13 weeks, wherein the induction dose contains about twice the amount of IL-23 binding protein as the maintenance dose. In some embodiments, the induction dose is administered as two doses four weeks apart.

In certain embodiments, the Fc region or modified Fc region is a human IgG1 immunoglobulin region. In some embodiments, the IL-23 binding protein is a humanized IL-23 binding protein. In some embodiments, the step of administering comprises systemic administration of the IL-23 binding protein. In some embodiments, the systemic administration comprises subcutaneous administration of the IL-23 binding protein. In some embodiments, the systemic administration comprises intravenous administration of the IL-23 binding protein. In some embodiments, the subject is a mammal. In certain embodiments, the subject is a primate. In certain embodiments, the subject is a human.

In another aspect, the disclosure provides the IL-23 binding protein or composition as provided herein for use in treatment of a disease of condition. In another aspect, the disclosure provides use of the IL-23 binding protein or composition as provided herein in a method of treating a disease or condition. In another aspect, the disclosure provides use of the IL-23 binding protein or composition as provided herein in the manufacture of a medicament for treating a disease or condition. In some embodiments, the disease or condition is an inflammatory disease or condition. In some embodiments, the disease or condition is gastrointestinal inflammatory disease. In some embodiments, the disease or condition is inflammatory bowel disease. In some embodiments, the disease or condition is Crohn's disease. In some embodiments, the disease or condition is ulcerative colitis.

DETAILED DESCRIPTION

Definitions

Figure 1:
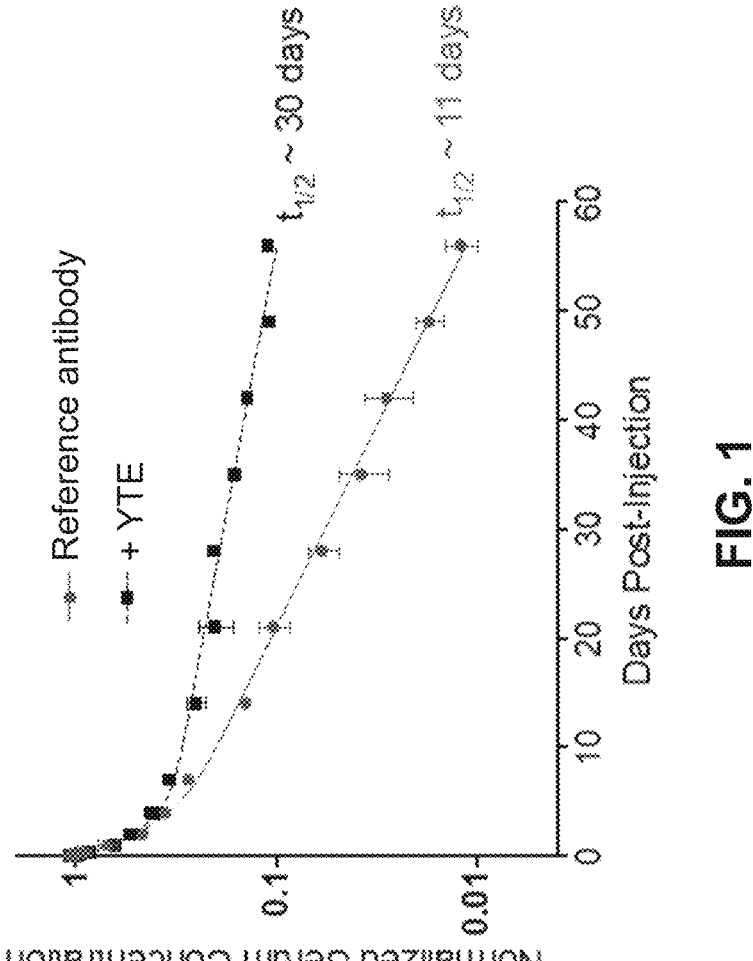
FIG. 1 is a graph of normalized serum concentration (y-axis) plotted against days post-injection (x-axis) in cynomolgus monkeys intravenously administered a single bolus dose (5 mg/kg) of an IL-23p19 binding protein with ("+YTE") or without ("reference antibody") Fc YTE mutations (Reference Antibody 1). See Example 7.

As used herein, the terms "about," "approximately," and "comparable to," when used herein in reference to a value, refer to a value that is similar to the referenced value in the context of that referenced value. In general, those skilled in the art, familiar with the context, will appreciate the relevant degree of variance encompassed by "about," "approximately," and "comparable to" in that context. For example, in some embodiments, the terms "about," "approximately," and "comparable to" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

As used herein, the terms "antagonistic," "neutralizing" or "blocking," when used in reference to an antibody or antigen-binding fragment thereof, is intended to refer to an antibody or fragment thereof whose binding to its target results in inhibition of at least some of the biological activity of the target.

As used herein, "antibody" refers to a polypeptide whose amino acid sequence includes immunoglobulins and fragments thereof which specifically bind to a designated antigen, or fragments thereof. Antibodies in accordance with the present invention may be of any type (e.g., IgA, IgD, IgE, IgG, or IgM) or subtype (e.g., IgA1, IgA2, IgG1, IgG2, IgG3, or IgG4). Those of ordinary skill in the art will appreciate that a characteristic sequence or portion of an antibody may include amino acids found in one or more regions of an antibody (e.g., variable region, hypervariable region, constant region, heavy chain, light chain, and combinations thereof). Moreover, those of ordinary skill in the art will appreciate that a characteristic sequence or portion of an antibody may include one or more polypeptide chains, and may include sequence elements found in the same polypeptide chain or in different polypeptide chains.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

An "antigen-binding fragment" of an antibody, or "antibody fragment" comprises a portion of an intact antibody, which portion is still capable of antigen binding. In some embodiments, the antibody has a function in addition to that of antigen-binding, and an antigen-binding fragment retains that function. Typically, an antigen-binding fragment comprises the variable region of the antibody. Papain digestion of antibodies produce two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and that is still capable of cross-linking antigen. Fab' fragments differ from Fab fragments by having a few additional residues at the carboxy terminus of the $C_H1$ domain, including one or more cysteines from the antibody hinge region. Fab'-SH designates an Fab' in which the cysteine residue(s) of the constant domains bear a free thiol group. F(ab')$_2$ antibody fragments originally were produced as pairs of Fab' fragments having hinge cysteines between them. Other chemical couplings of antibody fragments are also known.

As used herein, the term "chimeric antibody" refers to an antibody that has a portion of its heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass.

A "complementarity determining region" (abbreviated "CDR") is a region of hypervariability interspersed within regions that are more conserved, termed "framework regions" (abbreviated "FR"). The FR of a variable region generally consists of four FRs: FR1, FR2, FR3, and FR4. For example, the VH and VL CDR and FR sequences generally appear in the following sequence: FR1-CDR1-FR2-CDR2-FR3-CDR3-FR4. In some embodiments, the sequences of the framework regions are identical to the framework regions in human germline sequences. In some embodiments, the sequences of the framework regions are modified with respect to the human germline sequence.

As used herein, the phrase "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), may be performed.

As used herein, the expression "control sequences" refers to DNA sequences necessary or advantageous for the expression of an operably linked coding sequence in a particular host organism. Control sequences that are typically suitable for prokaryotes, for example, include a promoter, optionally an operator sequence, and a ribosome binding site. Eukaryotic cells are known to utilize promoters, polyadenylation signals, and enhancers.

As used herein, antibody "effector functions" refer to those biological activities attributable to the Fc region (a native sequence Fc region or amino acid sequence variant Fc region) of an antibody, and which typically vary with the antibody isotype. Examples of antibody effector functions include, but are not limited to, C1q binding and complement dependent cytotoxicity, Fc receptor binding; antibody-dependent cell-mediated cytotoxicity (ADCC); phagocytosis, down regulation of cell surface receptors (e.g. B cell receptor), and B cell activation.

As used herein, the term "epitope" is an antigenic determinant that interacts with a specific antigen binding site in the variable region of an antibody molecule, known as the paratope, and which is comprised of the six complementary-determining regions of the antibody. A single antigen may have more than one epitope. Epitopes may be conformational or linear. A conformational epitope is comprised of spatially juxtaposed amino acids from different segments of a linear polypeptide chain. A linear epitope is comprised of adjacent amino acid residues in a polypeptide chain.

An Fc fragment comprises the carboxy-terminal portions of both heavy chains held together by disulfides. The effector functions of antibodies are determined by sequences in the Fc region, the region which is also recognized by Fc receptors (FcR) found on certain types of cells.

As used herein, the term "humanized," when used in reference to an antibody, refers to a form of a non-human (e.g., murine) antibody that is chimeric. A "humanized antibody" contains minimal sequences derived from non-human immunoglobulin. Typically, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having a desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the framework regions are those of a human immunoglobulin sequence although the framework regions may include one or more amino acid substitutions that improve binding affinity. In some embodiments, no more than six amino acid substitutions in the heavy chain and no more than three amino acid substitutions are used in the light chain in the framework region. The humanized antibody optionally also will comprise at least a portion of an immunoglobulin constant region (Fc), typically that of a human immunoglobulin.

As used herein, an "isolated" nucleic acid molecule is a nucleic acid molecule that is identified and separated from at least one contaminant molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as they exist in natural cells.

As used herein, the term "monoclonal antibody" refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies may be made by a hybridoma method, such as that first described by Kohler et al., Nature 256:495 (1975), or may be made by recombinant DNA methods (see, e.g., U.S. Pat. No. 4,816,567). "Monoclonal antibodies" may also be isolated from phage antibody libraries, e.g., using techniques described in Clackson et al., Nature 352:624-628 (1991) and Marks et al., J. Mol. Biol. 222:581-597 (1991).

As used herein, a nucleic acid is "operably linked" when it is placed into a functional relationship with another nucleic acid sequence. For example, DNA for a presequence or secretory leader is "operably linked" to DNA for a polypeptide if it is expressed as a preprotein that participates in the secretion of the polypeptide; a promoter or enhancer is "operably linked" to a coding sequence if it affects the transcription of the sequence; or a ribosome binding site is "operably linked" to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking may be accomplished, e.g., by ligation at convenient restriction sites. If such sites do not exist, synthetic oligonucleotide adaptors or linkers may be used in accordance with conventional practice.

As used herein, "polypeptide," which may be used interchangeably with "protein," refers to a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides can include one or more "non-natural" amino acids or other entities that nonetheless are capable of integrating into a polypeptide chain. In some embodiments, a polypeptide may be glycosylated, e.g., a polypeptide may contain one or more covalently linked sugar moieties. In some embodiments, a single "polypeptide" (e.g., an antibody polypeptide) may comprise two or more individual polypeptide chains, which may in some cases be linked to one another, for example by one or more disulfide bonds or other means.

As used herein, the phrase "reference level" generally refers to a level considered "normal" for comparison purposes, e.g., a level of an appropriate control. For example, in the context of half-life (e.g. serum half-life) of a protein (e.g., a binding protein) a reference level may refer to the half-life of a "reference binding protein" which may be, e.g., an immunoglobulin of the same class (e.g., IgG1, IgG2, or IgG4) having a wild-type Fc region or an Fc region lacking a half-life extending mutation. In some embodiments, the reference binding protein comprises the same complementarity-determining regions as those of the binding protein of interest (e.g., an IL-23 binding protein as described herein). In some embodiments, the reference binding protein comprises the same variable regions (e.g., heavy chain and/or light chain variable region) as those of the binding protein of interest (e.g., an IL-23 binding protein as described herein.)

As used herein, the term "relative $IC_{50}$" refers to an $IC_{50}$ value calculated relative to the $IC_{50}$ of a suitable reference antibody (with the reference antibody's $IC_{50}$ value being normalize to 1.000). An $IC_{50}$ of less than 1.000 indicates increased potency compared to the reference antibody. In some embodiments, the reference antibody is an IL-23 antibody which is capable of binding to an epitope on the p19 subunit of IL-23. In some embodiments, the reference antibody is an IL-23p19 antibody comprising a heavy chain variable domain comprising the amino acid sequence of SEQ ID NO: 156 and a light chain variable domain comprising the amino acid sequence of SEQ ID NO: 2.

As used herein, the phrases "therapeutically effective amount" and "effective amount" are used interchangeably and refer to an amount effective, at dosages and for periods of time necessary, to achieve a desired therapeutic result. A therapeutically effective amount may vary according to factors such as the type of disease (e.g., disease state, age, sex, and/or weight of the individual, and the ability of an antibody (or pharmaceutical composition thereof) to elicit a desired response in the individual. An effective amount may also be an amount for which any toxic or detrimental effects of the antibody or pharmaceutical composition thereof are outweighed by therapeutically beneficial effects.

As used herein, to "treat" a condition or "treatment" of the condition (e.g., the conditions described herein) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Methods of Treatment

Provided herein, in certain embodiments, are methods of treating a gastrointestinal inflammatory disease in a patient in need thereof. As used herein, the term "gastrointestinal inflammatory disease" refers to a disease of the gastrointestinal tract that involves inflammatory pathways. For example, the gastrointestinal inflammatory disease includes, but is not limited to, inflammatory bowel disease, ulcerative colitis (with or without exposure to anti-tumor necrosis factor (anti-TNF), Crohn's disease (including fistulizing Crohn's Disease), chronic pouchitis, collagenous gastritis, microscopic or collagenous colitis, colitis (including immune mediated colitis), sclerosing cholangitis (including in subjects with underlying inflammatory bowel disease, celiac enteritis, ileitis. In other aspects of the disclosure, provided herein are methods of treating Intestinal Acute Graft Versus Host Disease (aGVHD) (e.g., in subjects undergoing allogeneic hematopoietic stem cell transplantation (Allo-HSCT)), steroid-refractory acute intestinal graft-versus-host disease (GvHD) (e.g. in subjects who have undergone Allo-HSCT), Type 1 diabetes (TID) (e.g., with or without anti-TNF pre-treatment), immune checkpoint inhibitor-related colitis in subjects with genitourinary cancer or melanoma.

In some embodiments, the disease is a gastrointestinal inflammatory disease. In some embodiments, the disease is an inflammatory bowel disease. In some embodiments, the inflammatory bowel disease is Crohn's disease. In some embodiments, the inflammatory bowel disease is ulcerative colitis.

In certain embodiments, provided are methods of treatment which generally comprise a step of administering a therapeutically effective amount of an IL-23 binding protein (or pharmaceutical composition thereof) of the present disclosure to a mammalian subject (e.g., a human subject) in need thereof.

In some embodiments, the subject has or is at risk of having an inflammatory bowel disease. In some embodiments, the inflammatory bowel disease is Crohn's disease or ulcerative colitis. In some embodiments, the inflammatory bowel disease is ulcerative colitis. In some embodiments, the inflammatory bowel disease is Crohn's disease.

In some embodiments, the subject has or is at risk of having an inflammatory disease or condition.

Therapeutically effective amounts of an IL-23 binding protein (or pharmaceutical composition thereof) may be administered via a single dose or via multiple doses (e.g., at least two, at least three, at least four, at least five, at least six, at least seven, at least eight, at least nine, or at least ten doses). When administered via multiple doses, any of a variety of suitable therapeutic regimens may be used, including administration of an IL-23 binding protein (or pharmaceutical composition thereof) at regular intervals (e.g., once every other day, once every three days, once every four days, once every five days, thrice weekly, twice weekly, once a week, once every two weeks, once every three weeks, etc.).

The dosage regimen of an IL-23 binding protein (or pharmaceutical composition thereof) (e.g., amounts of each therapeutic, relative timing of therapies, etc.) that is effective in methods of treatment may depend on the severity of the disease or condition and the weight and general state of the subject. For example, the therapeutically effective amount of a particular composition comprising a therapeutic agent (e.g., an IL-23 binding protein of the present disclosure) applied to mammals (e.g., humans) can be determined by the ordinarily-skilled artisan with consideration of individual differences in age, weight, and the condition of the mammal.

Also contemplated herein are, in certain embodiments, methods of treating gastrointestinal inflammatory disease, inflammatory bowel disease, ulcerative colitis, and/or Crohn's disease in a subject in need thereof, the method comprising a step of administering to the subject a dose of an IL-23 binding protein (such as an IL-23 binding protein as described herein) at regular intervals for a period of time sufficient to treat or ameliorate the gastrointestinal inflammatory disease, inflammatory bowel disease, ulcerative colitis, and/or Crohn's disease.

Regular Intervals of Administration of an IL-23 Binding Protein

By "regular interval," it is meant that the intervals between doses of an IL-23 binding protein (or pharmaceutical composition thereof) (e.g., maintenance doses) are at least substantially the same but need not be exactly the same, e.g., the durations between intervals may be within 10%, within 9%, within 8%, within 7%, within 6%, within 5%, within 4%, within 3%, within 2%, or within 1% of each other.

In some embodiments, the regular interval between maintenance doses of an IL-23 binding protein (or pharmaceutical composition thereof) is 8 weeks or more, e.g. greater than 8 weeks, greater than 12 weeks, greater than 16 weeks, greater than 20 weeks, or greater than 24 weeks. For example, in some embodiments, the regular interval is about 26 weeks.

In some embodiments, the regular interval is greater than 26 weeks, greater than 30 weeks, greater than 34 weeks, greater than 38 weeks, greater than 42 weeks, or greater than 48 weeks. For example, in some embodiments, the regular interval is about 52 weeks.

In some embodiments, the regular interval is greater than two months, greater than three months, greater than four months, or greater than five months. For example, in some embodiments, the regular interval is about three months. In some embodiments, the regular interval is about six months.

In some embodiments, the regular interval is about twice a year or about once a year.

In some embodiments, the regular interval is about 12 weeks to about 52 weeks, about 12 weeks to about 50 weeks, about 12 weeks to about 48 weeks, about 12 weeks to about 46 weeks, about 12 weeks to about 44 weeks, about 12 weeks to about 42 weeks, about 12 weeks to about 40 weeks, about 12 weeks to about 38 weeks, about 12 weeks to about 36 weeks, about 12 weeks to about 34 weeks, about 12 weeks to about 32 weeks, about 12 weeks to about 30 weeks, about 12 weeks to about 28 weeks, about 12 weeks to about 26 weeks, about 12 weeks to about 24 weeks, about 12 weeks to about 22 weeks, about 12 weeks to about 18 weeks, or about 12 weeks to about 14 weeks In some embodiments, the regular interval is about 16 weeks to about 52 weeks, about 16 weeks to about 50 weeks, about 16 weeks to about 48 weeks, about 16 weeks to about 46 weeks, about 16 weeks to about 44 weeks, about 16 weeks to about 42 weeks, about 16 weeks to about 40 weeks, about 16 weeks to about 38 weeks, about 16 weeks to about 36 weeks, about 16 weeks to about 34 weeks, about 16 weeks to about 32 weeks, about 16 weeks to about 30 weeks, about 16 weeks to about 28 weeks, about 16 weeks to about 26 weeks, about 16 weeks to about 24 weeks, about 16 weeks to about 22 weeks, or about 16 weeks to about 18 weeks.

In some embodiments, the regular interval is about 20 weeks to about 52 weeks, about 20 weeks to about 50 weeks, about 20 weeks to about 48 weeks, about 20 weeks to about 46 weeks, about 20 weeks to about 44 weeks, about 20 weeks to about 42 weeks, about 20 weeks to about 40 weeks, about 20 weeks to about 38 weeks, about 20 weeks to about 36 weeks, about 20 weeks to about 34 weeks, about 20 weeks to about 32 weeks, about 20 weeks to about 30 weeks, about 20 weeks to about 28 weeks, about 20 weeks to about 26 weeks, about 20 weeks to about 24 weeks, or about 20 weeks to about 22 weeks.

In some embodiments, the regular interval is about 24 weeks to about 52 weeks, about 24 weeks to about 50 weeks, about 24 weeks to about 48 weeks, about 24 weeks to about 46 weeks, about 24 weeks to about 44 weeks, about 24 weeks to about 42 weeks, about 24 weeks to about 40 weeks, about 24 weeks to about 38 weeks, about 24 weeks to about 36 weeks, about 24 weeks to about 34 weeks, about 24 weeks to about 32 weeks, about 24 weeks to about 30 weeks, about 24 weeks to about 28 weeks, or about 24 weeks to about 26 weeks.

In some embodiments, the regular interval is about 26 weeks to about 52 weeks, about 26 weeks to about 50 weeks, about 26 weeks to about 48 weeks, about 26 weeks to about 46 weeks, about 26 weeks to about 44 weeks, about 26 weeks to about 42 weeks, about 26 weeks to about 40 weeks, about 26 weeks to about 38 weeks, about 26 weeks to about 36 weeks, about 26 weeks to about 34 weeks, about 26 weeks to about 32 weeks, about 26 weeks to about 30 weeks, or about 26 weeks to about 28 weeks.

In some embodiments, the regular interval is about 28 weeks to about 52 weeks, about 28 weeks to about 50 weeks, about 28 weeks to about 48 weeks, about 28 weeks to about 46 weeks, about 28 weeks to about 44 weeks, about 28 weeks to about 42 weeks, about 28 weeks to about 40 weeks, about 28 weeks to about 38 weeks, about 28 weeks to about 36 weeks, about 28 weeks to about 34 weeks, about 28 weeks to about 32 weeks, or about 28 weeks to about 30 weeks.

In some embodiments, the regular interval is about 30 weeks to about 52 weeks, about 30 weeks to about 50 weeks, about 30 weeks to about 48 weeks, about 30 weeks to about 46 weeks, about 30 weeks to about 44 weeks, about 30 weeks to about 42 weeks, about 30 weeks to about 40 weeks, about 30 weeks to about 38 weeks, about 30 weeks to about 36 weeks, about 30 weeks to about 34 weeks, or about 30 weeks to about 32 weeks.

In some embodiments, the regular interval is about 32 weeks to about 52 weeks, about 32 weeks to about 50 weeks, about 32 weeks to about 48 weeks, about 32 weeks to about 46 weeks, about 32 weeks to about 44 weeks, about 32 weeks to about 42 weeks, about 32 weeks to about 40 weeks, about 32 weeks to about 38 weeks, about 32 weeks to about 36 weeks, or about 32 weeks to about 34 weeks.

In some embodiments, the regular interval is about 34 weeks to about 52 weeks, about 34 weeks to about 50 weeks, about 34 weeks to about 48 weeks, about 34 weeks to about 46 weeks, about 34 weeks to about 44 weeks, about 34 weeks to about 42 weeks, about 34 weeks to about 40 weeks, about 34 weeks to about 38 weeks, or about 34 weeks to about 36 weeks.

In some embodiments, the regular interval is about 36 weeks to about 52 weeks, about 36 weeks to about 50 weeks, about 36 weeks to about 48 weeks, about 36 weeks to about 46 weeks, about 36 weeks to about 44 weeks, about 36 weeks to about 42 weeks, about 36 weeks to about 40 weeks, or about 36 weeks to about 38 weeks.

In some embodiments, the regular interval is about 38 weeks to about 52 weeks, about 38 weeks to about 50 weeks, about 38 weeks to about 48 weeks, about 38 weeks to about 46 weeks, about 38 weeks to about 44 weeks, about 38 weeks to about 42 weeks, about 38 weeks to about 40 weeks, or about 38 weeks to about 38 weeks.

In some embodiments, the regular interval is about 40 weeks to about 52 weeks, about 40 weeks to about 50 weeks, about 40 weeks to about 48 weeks, about 40 weeks to about 46 weeks, about 40 weeks to about 44 weeks, or about 40 weeks to about 42 weeks.

In some embodiments, the regular interval is about 42 weeks to about 52 weeks, about 42 weeks to about 50 weeks, about 42 weeks to about 48 weeks, about 42 weeks to about 46 weeks, or about 42 weeks to about 44 weeks.

In some embodiments, the regular interval is about 44 weeks to about 52 weeks, about 44 weeks to about 50 weeks, about 44 weeks to about 48 weeks, or about 44 weeks to about 46 weeks.

In some embodiments, the regular interval is about 46 weeks to about 52 weeks, about 46 weeks to about 50 weeks, or about 46 weeks to about 48 weeks.

In some embodiments, the regular interval is about 48 weeks to about 52 weeks or about 48 weeks to about 50 weeks.

In some embodiments, the regular interval is about 50 weeks to about 52 weeks.

In some embodiments, the regular interval is about three months to about twelve months, about three months to about eleven and a half months, about three months to about eleven months, about three months to about ten and a half months, about three months to about ten months, about three months to about nine and a half months, about three months to about nine months, about three months to about eight and a half months, about three months to about eight months, about three months to about seven and a half months, about three months to about seven months, about three months to about six and a half months, about three months to about six months, about three months to about five and a half months, about three months to about five months, about three months to about four and half months, about three months to about four months, or about three months to about three and half months.

In some embodiments, the regular interval is about three and a half months to about twelve months, about three and a half months to about eleven and a half months, about three and a half months to about eleven months, about three and a half months to about ten and a half months, about three and a half months to about ten months, about three and a half months to about nine and a half months, about three and a half months to about nine months, about three and a half months to about eight and a half months, about three and a half months to about eight months, about three and a half months to about seven and a half months, about three and a half months to about seven months, about three and a half months to about six and a half months, about three and a half months to about six months, about three and a half months to about five and a half months, about three and a half months to about five months, about three and a half months to about four and half months, or about three and a half months to about four months.

In some embodiments, the regular interval is about four months to about twelve months, about four months to about eleven and a half months, about four months to about eleven months, about four months to about ten and a half months, about four months to about ten months, about four months to about nine and a half months, about four months to about nine months, about four months to about eight and a half months, about four months to about eight months, about four months to about seven and a half months, about four months to about seven months, about four months to about six and a half months, about four months to about six months, about four months to about five and a half months, about four months to about five months, or about four months to about four and half months.

In some embodiments, the regular interval is about four and a half months to about twelve months, about four and a half months to about eleven and a half months, about four and a half months to about eleven months, about four and a half months to about ten and a half months, about four and a half months to about ten months, about four and a half months to about nine and a half months, about four and a half months to about nine months, about four and a half months to about eight and a half months, about four and a half months to about eight months, about four and a half months to about seven and a half months, about four and a half months to about seven months, about four and a half months to about six and a half months, about four and a half months to about six months, about four and a half months to about five and a half months, or about four and a half months to about five months.

In some embodiments, the regular interval is about five months to about twelve months, about five months to about eleven and a half months, about five months to about eleven months, about five months to about ten and a half months, about five months to about ten months, about five months to about nine and a half months, about five months to about nine months, about five months to about eight and a half months, about five months to about eight months, about five months to about seven and a half months, about five months to about seven months, about five months to about six and a half months, about five months to about six months, or about five months to about five and a half months.

In some embodiments, the regular interval is about five and a half months to about twelve months, about five and a half months to about eleven and a half months, about five and a half months to about eleven months, about five and a half months to about ten and a half months, about five and a half months to about ten months, about five and a half months to about nine and a half months, about five and a half months to about nine months, about five and a half months to about eight and a half months, about five and a half months to about eight months, about five and a half months to about seven and a half months, about five and a half months to about seven months, about five and a half months to about six and a half months, or about five and a half months to about six months.

In some embodiments, the regular interval is about six months to about twelve months, about six months to about eleven and a half months, about six months to about eleven months, about six months to about ten and a half months, about six months to about ten months, about six months to about nine and a half months, about six months to about nine months, about six months to about eight and a half months, about six months to about eight months, about six months to about seven and a half months, about six months to about seven months, or about six months to about six and a half months.

In some embodiments, the regular interval is about six and a half months to about twelve months, about six and a half months to about eleven and a half months, about six and a half months to about eleven months, about six and a half months to about ten and a half months, about six and a half months to about ten months, about six and a half months to about nine and a half months, about six and a half months to about nine months, about six and a half months to about eight and a half months, about six and a half months to about eight months, about six and a half months to about seven and a half months, or about six and a half months to about seven months.

In some embodiments, the regular interval is about seven months to about twelve months, about seven months to about eleven and a half months, about seven months to about eleven months, about seven months to about ten and a half months, about seven months to about ten months, about seven months to about nine and a half months, about seven months to about nine months, about seven months to about eight and a half months, about seven months to about eight months, or about seven months to about seven and a half months.

In some embodiments, the regular interval is about seven and a half months to about twelve months, about seven and a half months to about eleven and a half months, about seven and a half months to about eleven months, about seven and a half months to about ten and a half months, about seven and a half months to about ten months, about seven and a half months to about nine and a half months, about seven and a half months to about nine months, about seven and a half months to about eight and a half months, or about seven and a half months to about eight months.

In some embodiments, the regular interval is about eight months to about twelve months, about eight months to about eleven and a half months, about eight months to about eleven months, about eight months to about ten and a half months, about eight months to about ten months, about eight months to about nine and a half months, about eight months to about nine months, or about eight months to about eight and a half months.

In some embodiments, the regular interval is about eight and a half months to about twelve months, about eight and a half months to about eleven and a half months, about eight and a half months to about eleven months, about eight and a half months to about ten and a half months, about eight and a half months to about ten months, about eight and a half months to about nine and a half months, or about eight and a half months to about nine months.

In some embodiments, the regular interval is about nine months to about twelve months, about nine months to about eleven and a half months, about nine months to about eleven months, about nine months to about ten and a half months, about nine months to about ten months, or about nine months to about nine and a half months.

In some embodiments, the regular interval is about nine and a half months to about twelve months, about nine and a half months to about eleven and a half months, about nine and a half months to about eleven months, about nine and a half months to about ten and a half months, or about nine and a half months to about ten months.

In some embodiments, the regular interval is about ten months to about twelve months, about ten months to about eleven and a half months, about ten months to about eleven months, or about ten months to about ten and a half months.

In some embodiments, the regular interval is about ten and a half months to about twelve months, about ten and a half months to about eleven and a half months, or about ten and a half months to about eleven months.

In some embodiments, the regular interval is about eleven months to about twelve months or about eleven months to about eleven and a half months.

In some embodiments, the regular interval is about eleven and a half months to about twelve months.

Dose Amounts

In some embodiments, each maintenance dose of the IL-23 binding protein is greater than 75 mg, greater than 100 mg, or greater than 125 mg. For example, in some embodiments, the maintenance dose is about 150 mg.

In some embodiments, each maintenance dose of the IL-23 binding protein is greater than 150 mg, greater than 200 mg, or greater than 250 mg. For example, in some embodiments, the maintenance dose is about 300 mg.

In some embodiments, each maintenance dose of the IL-23 binding protein is greater than 300 mg, greater than 400 mg, or greater than 500 mg. For example, in some embodiments, the maintenance dose is about 600 mg.

In some embodiments, each maintenance dose of the IL-23 binding protein is greater than 600 mg, greater than 700 mg, or greater than 800 mg. For example, in some embodiments, the maintenance dose is about 900 mg.

In some embodiments, each maintenance dose of the IL-23 binding protein is about 75 mg to about 1 g, about 75 mg to about 950 mg, about 75 mg to about 900 mg, about 75 mg to about 850 mg, about 75 mg to about 800 mg, about 75 mg to about 750 mg, about 75 mg to about 700 mg, about 75 mg to about 650 mg, about 75 mg to about 600 mg, about 75 mg to about 550 mg, about 75 mg to about 450 mg, about 75 mg to about 400 mg, about 75 mg to about 350 mg, about 75 mg to about 300 mg, about 75 mg to about 250 mg, about 75 mg to about 200 mg, or about 75 mg to about 150 mg.

In some embodiments, each maintenance dose of the IL-23 binding protein is about 150 mg to about 1 g, about 150 mg to about 950 mg, about 150 mg to about 900 mg, about 150 mg to about 850 mg, about 150 mg to about 800 mg, about 150 mg to about 750 mg, about 150 mg to about 700 mg, about 150 mg to about 650 mg, about 150 mg to about 600 mg, about 150 mg to about 550 mg, about 150 mg to about 450 mg, about 150 mg to about 400 mg, about 150 mg to about 350 mg, about 150 mg to about 300 mg, about 150 mg to about 250 mg, or about 150 mg to about 200 mg.

In some embodiments, each maintenance dose of the IL-23 binding protein is about 200 mg to about 1 g, about 200 mg to about 950 mg, about 200 mg to about 900 mg, about 200 mg to about 850 mg, about 200 mg to about 800 mg, about 200 mg to about 750 mg, about 200 mg to about 700 mg, about 200 mg to about 650 mg, about 200 mg to about 600 mg, about 200 mg to about 550 mg, about 200 mg to about 450 mg, about 200 mg to about 400 mg, about 200 mg to about 350 mg, about 200 mg to about 300 mg, or about 200 mg to about 250 mg.

In some embodiments, each maintenance dose of the IL-23 binding protein is about 250 mg to about 1 g, about 250 mg to about 950 mg, about 250 mg to about 900 mg, about 250 mg to about 850 mg, about 250 mg to about 800 mg, about 250 mg to about 750 mg, about 250 mg to about 700 mg, about 250 mg to about 650 mg, about 250 mg to about 600 mg, about 250 mg to about 550 mg, about 250 mg to about 450 mg, about 250 mg to about 400 mg, about 250 mg to about 350 mg, or about 250 mg to about 300 mg.

In some embodiments, each maintenance dose of the IL-23 binding protein is about 300 mg to about 1 g, about 300 mg to about 950 mg, about 300 mg to about 900 mg, about 300 mg to about 850 mg, about 300 mg to about 800 mg, about 300 mg to about 750 mg, about 300 mg to about 700 mg, about 300 mg to about 650 mg, about 300 mg to about 600 mg, about 300 mg to about 550 mg, about 300 mg to about 450 mg, about 300 mg to about 400 mg, or about 300 mg to about 350 mg.

In some embodiments, each maintenance dose of the IL-23 binding protein is about 350 mg to about 1 g, about 350 mg to about 950 mg, about 350 mg to about 900 mg, about 350 mg to about 850 mg, about 350 mg to about 800 mg, about 350 mg to about 750 mg, about 350 mg to about 700 mg, about 350 mg to about 650 mg, about 350 mg to about 600 mg, about 350 mg to about 550 mg, about 350 mg to about 450 mg, or about 350 mg to about 400 mg.

In some embodiments, each maintenance dose of the IL-23 binding protein is about 400 mg to about 1 g, about 400 mg to about 950 mg, about 400 mg to about 900 mg, about 400 mg to about 850 mg, about 400 mg to about 800 mg, about 400 mg to about 750 mg, about 400 mg to about 700 mg, about 400 mg to about 650 mg, about 400 mg to about 600 mg, about 400 mg to about 550 mg, or about 400 mg to about 450 mg.

In some embodiments, each maintenance dose of the IL-23 binding protein is about 450 mg to about 1 g, about 450 mg to about 950 mg, about 450 mg to about 900 mg, about 450 mg to about 850 mg, about 450 mg to about 800 mg, about 450 mg to about 750 mg, about 450 mg to about 700 mg, about 450 mg to about 650 mg, about 450 mg to about 600 mg, about 450 mg to about 550 mg, or about 450 mg to about 500 mg.

In some embodiments, each maintenance dose of the IL-23 binding protein is about 500 mg to about 1 g, about 500 mg to about 950 mg, about 500 mg to about 900 mg, about 500 mg to about 850 mg, about 500 mg to about 800 mg, about 500 mg to about 750 mg, about 500 mg to about 700 mg, about 500 mg to about 650 mg, about 500 mg to about 600 mg, or about 500 mg to about 550 mg.

In some embodiments, each maintenance dose of the IL-23 binding protein is about 550 mg to about 1 g, about 550 mg to about 950 mg, about 550 mg to about 900 mg, about 550 mg to about 850 mg, about 550 mg to about 800 mg, about 550 mg to about 750 mg, about 550 mg to about 700 mg, about 550 mg to about 650 mg, or about 550 mg to about 600 mg.

In some embodiments, each maintenance dose of the IL-23 binding protein is about 600 mg to about 1 g, about 600 mg to about 950 mg, about 600 mg to about 900 mg, about 600 mg to about 850 mg, about 600 mg to about 800 mg, about 600 mg to about 750 mg, about 600 mg to about 700 mg, or about 600 mg to about 650 mg.

In some embodiments, each maintenance dose of the IL-23 binding protein is about 650 mg to about 1 g, about 650 mg to about 950 mg, about 650 mg to about 900 mg, about 650 mg to about 850 mg, about 650 mg to about 800 mg, about 650 mg to about 750 mg, or about 650 mg to about 700 mg.

In some embodiments, each maintenance dose of the IL-23 binding protein is about 700 mg to about 1 g, about 700 mg to about 950 mg, about 700 mg to about 900 mg, about 700 mg to about 850 mg, about 700 mg to about 800 mg, or about 700 mg to about 750 mg.

In some embodiments, each maintenance dose of the IL-23 binding protein is about 750 mg to about 1 g, about 750 mg to about 950 mg, about 750 mg to about 900 mg, about 750 mg to about 850 mg, or about 750 mg to about 800 mg.

In some embodiments, each maintenance dose of the IL-23 binding protein is about 800 mg to about 1 g, about 800 mg to about 950 mg, about 800 mg to about 900 mg, or about 800 mg to about 850 mg.

In some embodiments, each maintenance dose of the IL-23 binding protein is about 850 mg to about 1 g, about 850 mg to about 950 mg, or about 850 mg to about 900 mg.

In some embodiments, each maintenance dose of the IL-23 binding protein is about 900 mg to about 1 g or about 900 mg to about 950 mg.

In some embodiments, each maintenance dose of the IL-23 binding protein is about 950 mg to about 1 g.

Actual dosage levels of the active ingredients in the pharmaceutical compositions of this disclosure may be in whatever amount as to obtain an amount of the active ingredient which is effective to achieve the desired therapeutic response for a particular patient, composition, and mode of administration, without being toxic to the patient.

The specific dose can be a uniform dose in the amounts mentioned herein. Alternatively, a patient's dose can be tailored to the approximate body weight or surface area of the patient. Other factors in determining the appropriate dosage can include the disease or condition to be treated or prevented, the severity of the disease, the route of administration, and the age, sex, and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica Chimica Acta* 308: 43-53, 2001; Steimer et al., *Clinica Chimica Acta* 308:33-41, 2001).

Induction Doses

In certain embodiments, e.g., the subject has received an induction dose of the IL-23 binding protein prior to the administering a first maintenance dose. In some embodiments, a single or more than one induction dose is administered, followed by maintenance doses. An induction dose can be administered intravenously or subcutaneously. The induction dose may be higher than a maintenance dose or more frequent than a maintenance dose, e.g., in case potentially by a factor of 2. The induction dose can be administered at once (e.g., in one day) or split into multiple (e.g., two) doses administered in parts a time period apart. In some embodiments, the amount of the induction dose is the same as the amount of each maintenance dose and is administered at once. In some embodiments, the amount of the induction dose is a multiple of the amount of the maintenance dose and is administered in parts, each part of the induction dose having the same amount of IL-23 binding protein as the amount in each maintenance dose. In embodiments in which the induction dose is administered in parts, the interval between each part may be, e.g., at least one week, at least two weeks, at least three weeks, or at least four weeks. In some embodiments, the induction dose is administered in parts, with an interval of about four weeks between each part.

Subjects

In certain embodiments, the subject to whom IL-23 binding proteins are administered in accordance with the present disclosure is a mammal, such as a primate. In some embodiments, the subject is human.

In some embodiments, the subject may be suffering from, exhibits at least one symptom of, is diagnosed with, and/or is identified as at risk of gastrointestinal inflammatory disease. In some embodiments, the subject may be suffering from, exhibits at least one symptom of, is diagnosed with, and/or is identified as at risk of inflammatory bowel disease, such as Crohn's disease and/or ulcerative colitis. Crohn's disease, for example, can be a chronic, long-term disease that causes inflammation in a subject's GI tract, and can affect any part of the GI tract from mouth to anus. Crohn's disease can be considered belong to a larger group of conditions related to inflammatory bowel disease or IBD. IBD affects the digestive system but can also cause problems in other parts of the body. Ulcerative colitis, another form of IBD, affects the large intestine (colon).

Routes of Administration

In certain embodiments, the step of administering comprises systemic administration. In certain embodiments, systemic administration comprises parenteral administration, e.g., intravenous administration, intraarterial administration, intraperitoneal administration, subcutaneous administration, or intradermal administration. In some embodiments, systemic administration comprises enteric administration, e.g., trans-gastroenteric administration or oral administration.

In some embodiments, the step of administering comprises intravenous administration. In some embodiments, the step of administering comprises subcutaneous administration.

Outcomes

In many embodiments, methods disclosed herein result in a measurable improvement in the subject, e.g., in amelioration or resolution of symptoms. For example, such improvement may include an improvement in a clinical score or a score from a survey or questionnaire associated with, or suitable for assessing, inflammatory bowel disease (e.g., ulcerative colitis and/or Crohn's disease).

II-23 Binding Proteins

In one aspect, provided proteins are capable of binding to IL-23 ("IL-23 binding proteins"). In some embodiments, provided binding proteins are capable of binding to an epitope of human IL-23, e.g., an epitope on the p19 subunit of IL-23 (IL-23A).

In some embodiments, the binding proteins are antibodies or fragments thereof. In some embodiments, the antibodies or fragments thereof are monoclonal antibodies or fragments thereof. In some embodiments, the antibodies or fragments thereof are chimeric antibodies or fragments thereof. In some embodiments, the antibodies or fragments thereof are humanized antibodies or fragments thereof. In some embodiments, the antibodies or antigen-binding fragments are human antibodies.

Antigen-binding fragments may be, e.g., an scFv, an Fab, an scFab (single-chain Fab). As used herein, the term "scFv" is used in accordance with its common usage in the art to refer to a single chain in which the $V_H$ domain and the $V_L$ domain from an antibody are joined, typically via a linker. As used herein, the term "Fab fragment" is used in accordance with its common usage in the art. Fab fragments typically comprise an entire light chain ($V_L$ and $C_L1$ domains), the variable region domain of the heavy chain (VH), and the first constant domain of one heavy chain ($C_H1$).

In some embodiments, IL-23 binding proteins comprise a heavy chain variable domain comprises complementarity determining regions CDR-H1, CDR-H2, and CDR-H3 with sequences as shown in a table selected from Tables 1A-1D. In some embodiments, IL-23 binding proteins further comprise a light chain variable domain comprising complementarity determining regions CDR-L1, CDR-L2, and CDR-L3 with sequences as shown in the same table of Tables 1A-1D.

In some embodiments, IL-23 binding proteins comprise a heavy chain variable domain comprises complementarity determining regions CDR-H1, CDR-H2, and CDR-H3 with sequences as shown in Table 1A. In some embodiments, IL-23 binding proteins further comprise a light chain variable domain comprising complementarity determining regions CDR-L1, CDR-L2, and CDR-L3 with sequences as shown in the same table of Table 1A. In some embodiments, IL-23 binding proteins comprise a heavy chain variable domain comprises complementarity determining regions CDR-H1 having an amino acid sequence with one or two substitutions as compared to the amino acid sequence of the CDR-H1 shown in Table 1A, CDR-H2 having an amino acid sequence with one or two substitutions as compared to the amino acid sequence of the CDR-H2 shown in Table 1A, and CDR-H3 having an amino acid sequence with one or two substitutions as compared to the amino acid sequence of CDR-H3 shown in Table 1A. In some embodiments, IL-23 binding proteins comprise a heavy chain variable domain comprises complementarity determining regions CDR-H1, CDR-H2, and CDR-H3 with sequences as shown in Table 1B. In some embodiments, IL-23 binding proteins comprise a heavy chain variable domain comprises complementarity determining regions CDR-H1 having an amino acid sequence with one or two substitutions as compared to the amino acid sequence of the CDR-H1 shown in Table 1B, CDR-H2 having an amino acid sequence with one or two substitutions as compared to the amino acid sequence of the CDR-H2 shown in Table 1B, and CDR-H3 having an amino acid sequence with one or two substitutions as compared to the amino acid sequence of CDR-H3 shown in Table 1B. In some embodiments, IL-23 binding proteins comprise a heavy chain variable domain comprises complementarity determining regions CDR-H1, CDR-H2, and CDR-H3 with sequences as shown in Table 1C. In some embodiments, IL-23 binding proteins comprise a heavy chain variable domain comprises complementarity determining regions CDR-H1 having an amino acid sequence with one or two substitutions as compared to the amino acid sequence of the CDR-H1 shown in Table 1C, CDR-H2 having an amino acid sequence with one or two substitutions as compared to the amino acid sequence of the CDR-H2 shown in Table 1C, and CDR-H3 having an amino acid sequence with one or two substitutions as compared to the amino acid sequence of CDR-H3 shown in Table 1C. In some embodiments, IL-23 binding proteins comprise a heavy chain variable domain comprises complementarity determining regions CDR-H1, CDR-H2, and CDR-H3 with sequences as shown in Table ID. In some embodiments, IL-23 binding proteins comprise a heavy chain variable domain comprises complementarity determining regions CDR-H1 having an amino acid sequence with one or two substitutions as compared to the amino acid sequence of the CDR-H1 shown in Table ID, CDR-H2 having an amino acid sequence with one or two substitutions as compared to the amino acid sequence of the CDR-H2 shown in Table 1D, and CDR-H3 having an amino acid sequence with one or two substitutions as compared to the amino acid sequence of CDR-H3 shown in Table 1D. In some embodiments, IL-23 binding proteins comprise a light chain variable domain comprises complementarity determining regions CDR-L1, CDR-L2, and CDR-L3 with sequences as shown in Table 1A. In some embodiments, IL-23 binding proteins comprise a light chain variable domain comprises complementarity determining regions CDR-L1 having an amino acid sequence with one or two substitutions as compared to the amino acid sequence of the CDR-L1 shown in Table 1A, CDR-L2 having an amino acid sequence with one or two substitutions as compared to the amino acid sequence of the CDR-L2 shown in Table 1A, and CDR-L3 having an amino acid sequence with one or two substitutions as compared to the amino acid sequence of CDR-L3 shown in Table 1A. In some embodiments, IL-23 binding proteins comprise a light chain variable domain comprises complementarity determining regions CDR-L1, CDR-L2, and CDR-L3 with sequences as shown in Table 1B. In some embodiments, IL-23 binding proteins comprise a light chain variable domain comprises complementarity determining regions CDR-L1 having an amino acid sequence with one or two substitutions as compared to the amino acid sequence of the CDR-L1 shown in Table 1B, CDR-L2 having an amino acid sequence with one or two substitutions as compared to the amino acid sequence of the CDR-L2 shown in Table 1B, and CDR-L3 having an amino acid sequence with one or two substitutions as compared to the amino acid sequence of CDR-L3 shown in Table 1B. In some embodiments, IL-23 binding proteins comprise a light chain variable domain comprises complementarity determining regions CDR-L1, CDR-L2, and CDR-L3 with sequences as shown in Table IC. In some embodiments, IL-23 binding proteins comprise a light chain variable domain comprises complementarity determining regions CDR-L1 having an amino acid sequence with one or two substitutions as compared to the amino acid sequence of the CDR-L1 shown in Table 1C, CDR-L2 having an amino acid sequence with one or two substitutions as compared to the amino acid sequence of the CDR-L2 shown in Table 1C, and CDR-L3 having an amino acid sequence with one or two substitutions as compared to the amino acid sequence of CDR-L3 shown in Table IC. In some embodiments, IL-23 binding proteins comprise a light chain variable domain comprises complementarity determining regions CDR-L1, CDR-L2, and CDR-L3 with sequences as shown in Table 1D. In some embodiments, IL-23 binding proteins comprise a light chain variable domain comprises complementarity determining regions CDR-L1 having an amino acid sequence with one or two substitutions as compared to the amino acid sequence of the CDR-L1 shown in Table 1D, CDR-L2 having an amino acid sequence with one or two substitutions as compared to the amino acid sequence of the CDR-L2 shown in Table 1D, and CDR-L3 having an amino acid sequence with one or two substitutions as compared to the amino acid sequence of CDR-L3 shown in Table 1D.

In some embodiments, IL-23 binding proteins comprise a heavy chain variable domain with heavy chain variable sequences as shown in a table selected from Tables 1A-1D. In some embodiments, IL-23 binding proteins comprise a heavy chain variable domain which is a variant of the heavy chain variable sequence shown in a table selected from Tables 1A-1D, in that the heavy chain variable domain has (1) CDR-H1, CDR-H2, and CDR-H3 with sequences as shown in a table selected from Tables 1A-1D and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence shown in the same table of Tables 1A-1D. In some embodiments, IL-23 binding proteins comprise a heavy chain variable domain with heavy chain variable sequences as shown in Table 1A. In some embodiments, IL-23 binding proteins comprise a heavy chain variable domain which is a variant of the heavy chain variable sequence shown in Table 1A, in that the heavy chain variable domain has (1) CDR-H1, CDR-H2, and CDR-H3 with sequences as shown in Table 1A and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence in Table 1A. In some embodiments, IL-23 binding proteins comprise a heavy chain variable domain with heavy chain variable sequences as shown in Table 1B. In some embodiments, IL-23 binding proteins comprise a heavy chain variable domain which is a variant of the heavy chain variable sequence shown in Table 1B, in that the heavy chain variable domain has (1) CDR-H1, CDR-H2, and CDR-H3 with sequences as shown in Table 1B and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence in Table 1B. In some embodiments, IL-23 binding proteins comprise a heavy chain variable domain with heavy chain variable sequences as shown in Table 1C. In some embodiments, IL-23 binding proteins comprise a heavy chain variable domain which is a variant of the heavy chain variable sequence shown in Table 1C, in that the heavy chain variable domain has (1) CDR-H1, CDR-H2, and CDR-H3 with sequences as shown in Table 1C and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence in Table 1C. In some embodiments, IL-23 binding proteins comprise a heavy chain variable domain with heavy chain variable sequences as shown in Table 1D. In some embodiments, IL-23 binding proteins comprise a heavy chain variable domain which is a variant of the heavy chain variable sequence shown in Table 1D, in that the heavy chain variable domain has (1) CDR-H1, CDR-H2, and CDR-H3 with sequences as shown in Table 1D and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the heavy chain variable domain sequence in Table 1D.

In some embodiments, IL-23 binding proteins comprise a heavy chain variable domain as described herein and further comprise a light chain variable region which has (1) CDR-L1, CDR-L2, and CDR-L3 with sequences as shown in a table selected from Tables 1A-1D and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in the same table of Tables 1A-1D. In some embodiments, IL-23 binding proteins comprise a heavy chain variable domain as described in Table 1A and further comprise a light chain variable region which has (1) CDR-L1, CDR-L2, and CDR-L3 with sequences as shown in Table 1A, and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in Table 1A. In some embodiments, IL-23 binding proteins comprise a heavy chain variable domain as described in Table 1B and further comprise a light chain variable region which has (1) CDR-L1, CDR-L2, and CDR-L3 with sequences as shown in Table 1B, and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in Table 1B. In some embodiments, IL-23 binding proteins comprise a heavy chain variable domain as described in Table 1C and further comprise a light chain variable region which has (1) CDR-L1, CDR-L2, and CDR-L3 with sequences as shown in Table 1C, and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in Table 1C. In some embodiments, IL-23 binding proteins comprise a heavy chain variable domain as described in Table 1D and further comprise a light chain variable region which has (1) CDR-L1, CDR-L2, and CDR-L3 with sequences as shown in Table 1D, and (2) an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence shown in Table 1D.

TABLE 1A

Exemplary heavy chain variable domain, light chain variable domain, and complementarity-determining region sequences of IL-23 binding proteins

| IL-23 binding protein | Heavy chain variable domain | Light chain variable domain |
|---|---|---|
| Clone MAb001 | QVQLVQSGAEVKKPGSSVKVSCKASG YTFTTQTLHWMRQAPGQGLEWIGYIY PRDGSTKYNENFKGKVTITADKSTST AYMELSSLRSEDTAVYYCAIPDRSGY AWFQHWGQGTLVTVSS (SEQ ID NO: 1) Kabat CDRs | DIQMTQSPSSLSASVGDRVTITCKAS RDVAIAVAWYQQKPGKVPKLLIYWAS TRHTGVPSRFSGSGSRTDFTLTISSL QPEDVADYFCHQYSSYPFTFGSGTKL EIK (SEQ ID NO: 2) Kabat CDRs |
| | CDR-H1: TQTLH (SEQ ID NO: 3) CDR-H2: YIYPRDGSTKYNENFKG (SEQ ID NO: 4) CDR-H3: PDRSGYAWFQH (SEQ ID NO: 5) IMGT CDRs | CDR-L1: KASRDVAIAVA (SEQ ID NO: 6) CDR-L2: WASTRHT (SEQ ID NO: 7) CDR-L3: HQYSSYPFT (SEQ ID NO: 8) IMGT CDRs |
| | CDR-H1: GYTFTTQT (SEQ ID NO: 9) CDR-H2: IYPRDGST (SEQ ID NO: 10) CDR-H3: AIPDRSGYAWFQH (SEQ ID NO: 11) Chothia CDRs | CDR-L1: RDVAIA (SEQ ID NO: 12) CDR-L2: WAS CDR-L3: HQYSSYPFT (SEQ ID NO: 8) Chothia CDRs |
| | CDR-H1: GYTFTTQ (SEQ ID NO: 13) CDR-H2: YPRDGS (SEQ ID NO: 14) CDR-H3: DRSGYAWFQ (SEQ ID NO: 15) | CDR-L1: SRDVAIA (SEQ ID NO: 16) CDR-L2: WAS CDR-L3: YSSYPF (SEQ ID NO: 17) |

TABLE 1B

Exemplary heavy chain variable domain, light chain variable domain, and
complementarity-determining region sequences of IL-23 binding proteins

| IL-23 binding protein | Heavy chain variable domain | Light chain variable domain |
|---|---|---|
| Clone MAb003 | QVQLVQSGAEVKKPGSSVKVSCKASG YTFTSQTMHWMRQAPGQGLEWIGYIY PRDDYPKYNDNFKGKVTITADKSTST AYMELSSLRSEDTAVYYCAIPDRSGY AWF IHWGQGTLVTVSS (SEQ ID NO: 18) Kabat CDRs | DIQMTQSPSSLSASVGDRVTITCKAS RDVAIAVAWYQQKPGKVPKLLIYWAS TRHTGVPSRFSGSGSRTDFTLTISSL QPEDVADYFCHQYSSYPFTFGSGTKL EIK (SEQ ID NO: 2) Kabat CDRs |
| | CDR-H1: SQTMH (SEQ ID NO: 19) CDR-H2: YIYPRDDYPKYNDNFKG (SEQ ID NO: 20) CDR-H3: PDRSGYAWFIH (SEQ ID NO: 21) IMGT CDRs | CDR-L1: KASRDVAIAVA (SEQ ID NO: 6) CDR-L2: WASTRHT (SEQ ID NO: 7) CDR-L3: HQYSSYPFT (SEQ ID NO: 8) IMGT CDRs |
| | CDR-H1: GYTFTSQT (SEQ ID NO: 22) CDR-H2: IYPRDDYP (SEQ ID NO: 23) CDR-H3: AIPDRSGYAWFIH (SEQ ID NO: 24) Chothia CDRs | CDR-L1: RDVAIA (SEQ ID NO: 12) CDR-L2: WAS CDR-L3: HQYSSYPFT (SEQ ID NO: 8) Chothia CDRs |
| | CDR-H1: GYTFTSQ (SEQ ID NO: 25) CDR-H2: YPRDDY (SEQ ID NO: 26) CDR-H3: DRSGYAWFI (SEQ ID NO: 27) | CDR-L1: SRDVAIA (SEQ ID NO: 16) CDR-L2: WAS CDR-L3: YSSYPF (SEQ ID NO: 17) |

TABLE 1C

Exemplary heavy chain variable domain, light chain variable domain, and
complementarity-determining region sequences of IL-23 binding proteins

| IL-23 binding protein | Heavy chain variable domain | Light chain variable domain |
|---|---|---|
| Clone MAb002 | EVQLLESGGGLVQPGGSLRLSCAASG YTFTDQTIHWVRQAPGKGLEWIGYIY PRDDSPKYNENFKGRATLSADNSKNT AYLQMNSLRAEDTAVYYCAIPDRSGY AWFIYWGQGTTVTVSS (SEQ ID NO: 28) Kabat CDRs | EIVMTQSPATLSVSPGERATLSCKAS RDVAIAVAWYQQKPGQAPRLLLFWAS TRHTGIPARFSGSGSRTEFTLTISSL QSEDFAVYYCHQYSSYPFTFGGGTKV EIK (SEQ ID NO: 29) Kabat CDRs |
| | CDR-H1: DQTIH (SEQ ID NO: 30) CDR-H2: YIYPRDDSPKYNENFKG (SEQ ID NO: 31) CDR-H3: PDRSGYAWFIY (SEQ ID NO: 32) IMGT CDRs | CDR-L1: KASRDVAIAVA (SEQ ID NO: 6) CDR-L2: WASTRHT (SEQ ID NO: 7) CDR-L3: HQYSSYPFT (SEQ ID NO: 8) IMGT CDRs |
| | CDR-H1: GYTFTDQT (SEQ ID NO: 33) CDR-H2: IYPRDDSP (SEQ ID NO: 34) CDR-H3: AIPDRSGYAWFIY (SEQ ID NO: 35) | CDR-L1: RDVAIA (SEQ ID NO: 12) CDR-L2: WAS CDR-L3: HQYSSYPFT (SEQ ID NO: 8) |

TABLE 1C-continued

Exemplary heavy chain variable domain, light chain variable domain, and complementarity-determining region sequences of IL-23 binding proteins

| IL-23 binding protein | Heavy chain variable domain | Light chain variable domain |
|---|---|---|
| | Chothia CDRs | Chothia CDRs |
| | CDR-H1: GYTFTDQ (SEQ ID NO: 36) CDR-H2: YPRDDS (SEQ ID NO: 37) CDR-H3: DRSGYAWFI (SEQ ID NO: 27) | CDR-L1: SRDVAIA (SEQ ID NO: 16) CDR-L2: WAS CDR-L3: YSSYPF (SEQ ID NO: 17) |

TABLE 1D

Exemplary heavy chain variable domain, light chain variable domain, and complementarity-determining region sequences of IL-23 binding proteins

| IL-23 binding protein | Heavy chain variable domain | Light chain variable domain |
|---|---|---|
| Clone MAb004 | QVQLVQSGAEVKKPGSSVKVSCKASG YTFTAQTMHWMRQAPGQGLEWIGYIY PRDGSTKYNENFKGKVTITADKSTST AYMELSSLRSEDTAVYYCAIPDRSGY AWFIVWGQGTLVTVSS (SEQ ID NO: 38) | EIVMTQSPATLSVSPGERATLSCKAS RDVAIAVAWYQQKPGQAPRLLLFWAS TRHTGIPARFSGSGSRTEFTLTISSL QSEDFAVYYCHQYSSYPFTFGGGTKV EIK (SEQ ID NO: 29) |
| | Kabat CDRs | Kabat CDRs |
| | CDR-H1: AQTMH (SEQ ID NO: 39) CDR-H2: YIYPRDGSTKYNENFKG (SEQ ID NO: 4) CDR-H3: PDRSGYAWFIV (SEQ ID NO: 40) | CDR-L1: KASRDVAIAVA (SEQ ID NO: 6) CDR-L2: WASTRHT (SEQ ID NO: 7) CDR-L3: HQYSSYPFT (SEQ ID NO: 8) |
| | IMGT CDRs | IMGT CDRs |
| | CDR-H1: GYTFTAQT (SEQ ID NO: 41) CDR-H2: IYPRDGST (SEQ ID NO: 10) CDR-H3: AIPDRSGYAWFIV (SEQ ID NO: 42) | CDR-L1: RDVAIA (SEQ ID NO: 12) CDR-L2: WAS CDR-L3: HQYSSYPFT (SEQ ID NO: 8) |
| | Chothia CDRs | Chothia CDRs |
| | CDR-H1: GYTFTAQ (SEQ ID NO: 43) CDR-H2: YPRDGS (SEQ ID NO: 14) CDR-H3: DRSGYAWFI (SEQ ID NO: 27) | CDR-L1: SRDVAIA (SEQ ID NO: 16) CDR-L2: WAS CDR-L3: YSSYPF (SEQ ID NO: 17) |

50

In some embodiments, IL-23 binding proteins comprise a heavy chain and a light chain as shown in Table 1.1A-Table 1.1D.

TABLE 1.1 A

Exemplary heavy and light chain amino acid sequences of IL-23 binding proteins

| IL-23 binding protein | Heavy chain | Light chain |
|---|---|---|
| Clone MAb001 | QVQLVQSGAEVKKPGSSVKVSCK ASGYTFTTQTLHWMRQAPGQGLE WIGYIYPRDGSTKYNENFKGKVTI TADKSTSTAYMELSSLRSEDTAVY YCAIPDRSGYAWFQHWGQGTLVT VSSASTKGPSVFPLAPSSKSTSGGT | DIQMTQSPSSLSASVGDRVTITCK ASRDVAIAVAWYQQKPGKVPKLL IYWASTRHTGVPSRFSGSGSRTDF TLTISSLQPEDVADYFCHQYSSYPF TFGSGTKLEIKRTVAAPSVFIFPPS DEQLKSGTASVVCLLNNFYPREA |

TABLE 1.1 A-continued

Exemplary heavy and light chain amino acid sequences of IL-23 binding
proteins

| IL-23 binding protein | Heavy chain | Light chain |
| --- | --- | --- |
| | AALGCLVKDYFPEPVTVSWNSGA LTSGVHTFPAVLQSSGLYSLSSVV TVPSSSLGTQTYICNVNHKPSNTK VDKKVEPKSCDKTHTCPPCPAPEA AGGPSVFLFPPKPKDTLYITREPEV TCVVVDVSHEDPEVKFNWYVDG VEVHNAKTKPREEQYNSTYRVVS VLTVLHQDWLNGKEYKCKVSNK ALPAPIEKTISKAKGQPREPQVYTL PPSRDELTKNQVSLTCLVKGFYPS DIAVEWESNGQPENNYKTTPPVL DSDGSFFLYSKLTVDKSRWQQGN VFSCSVMHEALHNHYTQKSLSLSP GK (SEQ ID NO: 165) | KVQWKVDNALQSGNSQESVTEQ DSKDSTYSLSSTLTLSKADYEKHK VYACEVTHQGLSSPVTKSFNRGEC (SEQ ID NO: 166) |

TABLE 1.1 B

Exemplary heavy and light chain amino acid sequences of IL-23 binding
proteins

| IL-23 binding protein | Heavy chain | Light chain |
| --- | --- | --- |
| Clone MAb003 | QVQLVQSGAEVKKPGSSVKVSCK ASGYTFTSQTMHWMRQAPGQGL EWIGYIYPRDDYPKYNDNFKGKV TITADKSTSTAYMELSSLRSEDTA VYYCAIPDRSGYAWFIHWGQGTL VTVSSASTKGPSVFPLAPSSKSTSG GTAALGCLVKDYFPEPVTVSWNS GALTSGVHTFPAVLQSSGLYSLSS VVTVPSSSLGTQTYICNVNHKPSN TKVDKKVEPKSCDKTHTCPPCPAP EAAGGPSVFLFPPKPKDTLYITREP EVTCVVVDVSHEDPEVKFNWYV DGVEVHNAKTKPREEQYNSTYRV VSVLTVLHQDWLNGKEYKCKVS NKALPAPIEKTISKAKGQPREPQV YTLPPSRDELTKNQVSLTCLVKGF YPSDIAVEWESNGQPENNYKTTPP VLDSDGSFFLYSKLTVDKSRWQQ GNVFSCSVMHEALHNHYTQKSLS LSPGK (SEQ ID NO: 169) | DIQMTQSPSSLSASVGDRVTITCK ASRDVAIAVAWYQQKPGKVPKLL IYWASTRHTGVPSRFSGSGSRTDF TLTISSLQPEDVADYFCHQYSSYPF TFGSGTKLEIKRTVAAPSVFIFPPS DEQLKSGTASVVCLLNNFYPREA KVQWKVDNALQSGNSQESVTEQ DSKDSTYSLSSTLTLSKADYEKHK VYACEVTHQGLSSPVTKSFNRGEC (SEQ ID NO: 170) |

TABLE 1.1 C

Exemplary heavy and light chain amino acid sequences of IL-23 binding
proteins

| IL-23 binding protein | Heavy chain | Light chain |
| --- | --- | --- |
| Clone MAb002 | EVQLLESGGGLVQPGGSLRLSCAA SGYTFTDQTIHWVRQAPGKGLEW IGYIYPRDDSPKYNENFKGRATLS ADNSKNTAYLQMNSLRAEDTAV YYCAIPDRSGYAWFIYWGQGTTV TVSSASTKGPSVFPLAPSSKSTSGG TAALGCLVKDYFPEPVTVSWNSG ALTSGVHTFPAVLQSSGLYSLSSV VTVPSSSLGTQTYICNVNHKPSNT KVDKKVEPKSCDKTHTCPPCPAPE AAGGPSVFLFPPKPKDTLYITREPE VTCVVVDVSHEDPEVKFNWYVD | EIVMTQSPATLSVSPGERATLSCK ASRDVAIAVAWYQQKPGQAPRLL LFWASTRHTGIPARFSGSGSRTEFT LTISSLQSEDFAVYYCHQYSSYPFT FGGGTKVEIKRTVAAPSVFIFPPSD EQLKSGTASVVCLLNNFYPREAK VQWKVDNALQSGNSQESVTEQDS KDSTYSLSSTLTLSKADYEKHKVY ACEVTHQGLSSPVTKSFNRGEC (SEQ ID NO: 172) |

TABLE 1.1 C-continued

Exemplary heavy and light chain amino acid sequences of IL-23 binding
proteins

| IL-23 binding protein | Heavy chain | Light chain |
|---|---|---|
| | GVEVHNAKTKPREEQYNSTYRVV SVLTVLHQDWLNGKEYKCKVSN KALPAPIEKTISKAKGQPREPQVY TLPPSRDELTKNQVSLTCLVKGFY PSDIAVEWESNGQPENNYKTTPPV LDSDGSFFLYSKLTVDKSRWQQG NVFSCSVMHEALHNHYTQKSLSL SPGK (SEQ ID NO: 171) | |

TABLE 1.1 D

Exemplary heavy and light chain amino acid sequences of IL-23 binding
proteins

| IL-23 binding protein | Heavy chain | Light chain |
|---|---|---|
| Clone MAb004 | FPLAPSSKSTSGGTAALGCLVKDY FPEPVTVSWNSGALTSGVHTFPAV LQSSGLYSLSSVVTVPSSSLGTQTY ICNVNHKPSNTKVDKKVEPKSCD KTHTCPPCPAPEAAGGPSVFLPPP KPKDTLYITREPEVTCVVVDVSHE DPEVKFNWYVDGVEVHNAKTKP REEQYNSTYRVVSVLTVLHQDWL NGKEYKCKVSNKALPAPIEKTISK AKGQPREPQVYTLPPSRDELTKNQ VSLTCLVKGFYPSDIAVEWESNGQ PENNYKTTPPVLDSDGSFFLYSKL TVDKSRWQQGNVFSCSVMHEAL HNHYTQKSLSLSPGK (SEQ ID NO: 167) | EIVMTQSPATLSVSPGERATLSCK ASRDVAIAVAWYQQKPGQAPRLL LFWASTRHTGIPARFSGSGSRTEFT LTISSLQSEDFAVYYCHQYSSYPFT FGGGTKVEIKRTVAAPSVFIFPPSD EQLKSGTASVVCLLNNFYPREAK VQWKVDNALQSGNSQESVTEQDS KDSTYSLSSTLTLSKADYEKHKVY ACEVTHQGLSSPVTKSFNRGEC (SEQ ID NO: 168) |

In some embodiments, IL-23 binding proteins comprise a heavy chain as shown in Table 1.1A and a light chain as shown in Table 1.1A. In some embodiments, IL-23 binding proteins comprise (1) CDR-H1, CDR-H2, and CDR-H3 sequences as shown in Table 1A, and (2) a heavy chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1A. In some embodiments, IL-23 binding proteins comprise (1) CDR-L1, CDR-L2, and CDR-L3 sequences as shown in Table 1A, and (2) a light chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1A.

In some embodiments, IL-23 binding proteins comprise a heavy chain as shown in Table 1.1B and a light chain as shown in Table 1.1B. In some embodiments, IL-23 binding proteins comprise (1) CDR-H1, CDR-H2, and CDR-H3 sequences as shown in Table 1B, and (2) a heavy chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1B. In some embodiments, IL-23 binding proteins comprise (1) CDR-L1, CDR-L2, and CDR-L3 sequences as shown in Table 1A, and (2) a light chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1B.

In some embodiments, IL-23 binding proteins comprise a heavy chain as shown in Table 1.1C and a light chain as shown in Table 1.1C. In some embodiments, IL-23 binding proteins comprise a heavy chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1C, CDR-H1, CDR-H2, and CDR-H3 with sequences as shown in Table 1C, an amino acid sequence that is at least 85% identical to the amino acid sequence of the heavy chain variable domain sequence in Table 1C and asparagine at position 74 of the heavy chain variable domain sequence. In some embodiments, IL-23 binding proteins comprise a light chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1C, CDR-L1, CDR-L2, and CDR-L3 with sequences as shown in Table IC and an amino acid sequence that is at least 85% identical to the amino acid sequence of the light chain variable domain sequence in Table 1C and phenylalanine at position 49 of the light chain variable domain sequence. In an embodiment, the amino acid at position 27 of the heavy chain variable domain in Table 1C is not asparagine. In a further embodiment, the amino acid at position 27 of the heavy chain variable domain in Table 1C is a tyrosine. In another embodiment, the amino acid at position 74 the heavy chain variable domain in Table 1C is not lysine. In another embodiment, the amino acid at position 49 of the light chain variable domain in Table 1C is not tyrosine.

In some embodiments, IL-23 binding proteins comprise a heavy chain as shown in Table 1.1D and a light chain as shown in Table 1.1D. In some embodiments, IL-23 binding proteins comprise (1) CDR-H1, CDR-H2, and CDR-H3 sequences as shown in Table 1B, and (2) a heavy chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1D. In some embodiments, IL-23 binding proteins comprise a light chain having an amino acid sequence that is at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to the amino acid sequence of the heavy chain shown in Table 1.1D, CDR-L1, CDR-L2, and CDR-L3 with sequences as shown in Table IC and an amino acid sequence that is at least 85%, at least 87.5%, at least 90%, at least 91%, at least 92%, at least 93%, at least 94%, at least 95%, at least 96%, at least 97%, at least 98%, or at least 99% identical to the amino acid sequence of the light chain variable domain sequence in Table ID.

In some embodiments, the IL-23 binding protein comprises: a heavy chain variable domain (VH) comprising (1) an amino acid sequence that is at least 85% identical to amino acid sequence of SEQ ID NO: 28, (2) asparagine at position 74 of SEQ ID NO: 28; and (3) one or more of glutamic acid at position 1, leucine at position 5, glutamic acid at position 6, glycine at position 9, glycine at position 10, leucine at position 11, valine at position 12, glutamine at position 13, glycine at position 16, leucine at position 18, arginine at position 19, leucine at position 20, alanine at position 23, valine at position 37, lysine at position 43, arginine at position 67, leucine a position 70, serine at position 71, alanine at position 68, lysine at position 76, asparagine at position 77, leucine at position 81, glutamine at position 82, methionine at position 83, asparagine at position 84, alanine a position 88, or threonine at position 115 of SEQ ID NO: 28, (4) complementarity-determining regions: CDR-H1 comprising the amino acid sequence of SEQ ID NO: 30; CDR-H2 comprising the amino acid sequence of SEQ ID NO: 31; and CDR-H3 comprising the amino acid sequence of SEQ ID NO: 32. In some embodiments, the II-23 protein further comprises (b) a light chain variable domain (VL) comprising: (1) an amino acid sequence that is at least 85% identical to amino acid sequence of SEQ ID NO: 29, and (2) one or more of glutamic acid at position 1, valine at position 3, alanine at position 9, threonine at position 10, valine at position 13, proline at position 15, glutamic acid at position 17, alanine at position 19, leucine at position 21, serine at position 22, glutamine at position 42, alanine at position 43, arginine at position 45, leucine at position 48, phenylalanine at position 49 isoleucine at position 58, alanine at position 60, glutamic acid at position 70, serine at position 80, phenylalanine at position 83, valine at position 85, tyrosine at position 87, glycine at position 100 or valine at position 104 of SEQ ID NO: 29, (3) complementarity-determining regions: CDR-L1 comprising the amino acid sequence of SEQ ID NO: 6; CDR-L2 comprising the amino acid sequence of SEQ ID NO: 7; an CDR-L3 comprising the amino acid sequence of SEQ ID NO: 8.

Fc Regions

IL-23 binding proteins suitable for use in accordance with the present disclosure typically comprise an Fc region, which typically comprises one or more Fc chains. An IgG Fc chain typically contains two constant heavy domains (CH2 and CH3) and a hinge region connected to the CH2 domain. Typical Fc regions comprise two Fc chains which dimerize with one another; however, an Fc region may have a single chain or more than two Fc chains, e.g., as may be present in some antibody formats. In certain embodiments, an Fc region may have one or more modifications (e.g., changes such as deletions, additions, or substitutions to one or more amino acid residues), such as provided herein (see, e.g., Table 2). In some such embodiments, a modification changes a function of an Fc region (e.g., by changing binding affinity to an Fc receptor, etc.).

In some embodiments, IL-23 binding proteins comprise an IgG1 Fc region (e.g., human IgG1 Fc region), that is, except for having particular residue(s) at certain positions as noted herein, the Fc region has an amino acid sequence that is substantially similar to that of the Fc region within a wild type IgG1 Fc. In some embodiments, the wild type IgG1 Fc is a human IgG1 Fc, in which each Fc chain has an amino acid sequence of SEQ ID NO: 44. In some embodiments, IL-23 binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG1 Fc.

In some embodiments, IL-23 binding proteins comprise an IgG2 Fc region (e.g., human IgG2 Fc region), that is, except for having particular residue(s) at certain positions as noted herein, the Fc region has an amino acid sequence that is substantially similar to that of the Fc region within a wild type IgG2 Fc. In some embodiments, the wild type IgG2 Fc is a human IgG2 Fc, in which each Fc chain has an amino acid sequence of SEQ ID NO: 45. In some embodiments, IL-23 binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG2 Fc.

In some embodiments, IL-23 binding proteins comprise an IgG4 Fc region (e.g., human IgG4 Fc region), that is, except for having particular residue(s) at certain positions as noted herein, the Fc region has an amino acid sequence that is substantially similar to that of the Fc region within a wild type IgG4 Fc. In some embodiments, the wild type IgG4 Fc is a human IgG4 Fc, in which each Fc chain has an amino acid sequence of SEQ ID NO: 46. In some embodiments, IL-23 binding proteins comprise an Fc region, each Fc chain of which has an amino acid sequence that is at least 85%, at least 87.5%, at least 90%, at least 91%, at least 92%, at least 93%, at least 94%, at least 95%, at least 96%, at least 97%, at least 98%, or at least 99% identical to that of an Fc chain within a wild-type IgG4 Fc.

In some embodiments, the one or more modifications modify binding to Fc-gamma receptors, e.g., by promoting selective binding, reducing binding, or enhancing binding thereto.

In some embodiments, an IL-23 binding protein is an anti-IL-23 antibody with an improvement comprising modification of the Fc portion to increase half-life in humans compared to that antibody without such modification, e.g., substitutions corresponding to M252Y, S254T, and T256E (YTE) and/or M428L and N434S (LS), for example an increase by a factor of at least two, or at least three, or at least four. In some embodiments the half-life extension modification is or comprises the YTE modification. In some embodiments the half-life extension modification is or comprises the LS modification.

In some embodiments, an IL-23 binding protein is an anti-IL-23 antibody with an improvement comprising modification of the framework region (FR) sequence of the heavy chain. In some embodiments, the modification comprises one or more modifications of FR1, FR2, FR3 and FR4 of the heavy chain. In some embodiments, the modification comprises one or more modifications of FR1, FR2, FR3 and FR4. In some embodiments, the modification can comprise non-conservative and/or conservative modifications such as amino acid substitutions. Conservative substitutions of one amino acid for another generally retain side-chain properties. In some cases, conservative substitutions retain the shape or size of the original residue. In some embodiments, the modifications comprise conservative substitutions of one or more of amino acid sequence of FR1, FR2, FR3 and FR4, for example FR1, FR2 and FR3. In some embodiments, the one or modifications comprise asparagine at position 74. In some embodiments, the modification results in a heavy chain variable region sequence of SEQ ID NO: 28. In some embodiments an IL-23 binding protein is an anti-IL-23 antibody with an improvement comprising modification of the complementarity determining region (CDR) of the heavy chain. In some embodiments, the modification results in heavy chain CDR sequences corresponding to CDRs 1, 2, and 3 in Tables 1A, 1B, and 1D.

In some embodiments, the anti-IL-23 antibody has improved binding affinity to IL-23, more effective inhibition of IL-23-induced activation of STAT3 and/or more effective inhibition of IL-23-induced phosphorylation of STAT3, as compared to a reference antibody (e.g. Reference Antibody 1). In some embodiments, the anti-IL-23 binding antibody is capable of inhibiting activation of STAT3 at a relative $IC_{50}$ of less than 0.90. In some embodiments, the IL-23 binding protein is capable of inhibiting phosphorylation of STAT3 at a relative $IC_{50}$ reference of less than 0.80. In some embodiments an IL-23 binding protein comprises modification of the framework region (FR) sequence of the heavy chain and/or light chain, and/or modification of the complementarity determining region (CDR) of the heavy chain as compared to a reference antibody (e.g. Reference Antibody 1).

In some embodiments, an IL-23 binding protein is means for binding IL-23 with a Fc portion modified to increase half-life in humans compared to that antibody without such modification, e.g., M252Y, S254T, and T256E (YTE) and/or M428L and N434S (LS), for example an increase by a factor of at least two, or at least three, or at least four. In some embodiments the half-life extension modification is the YTE modification. In some embodiments the half-life extension modification is the LS modification.

In some embodiments, provided is an IL-23 binding protein comprising a means for binding IL-23 with a modified framework region (FR) sequence of the heavy chain. In some embodiments, the modification results in a heavy chain variable region sequence of SEQ ID NO: 28.

In some embodiments, provided is an IL-23 binding protein comprising a means for binding IL-23 with a modified complementarity determining region (CDR) of the heavy chain. In some embodiments, the modification results in heavy chain CDR sequences corresponding to CDRs 1, 2, and 3 in Tables 1A, 1B, and 1D.

Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991.

Amino acid sequences of exemplary Fc sequences are provided in Table 2.

TABLE 2

| | | Exemplary Fc Sequences | |
|---|---|---|---|
| Name | SEQ ID NO | Fc chain sequence | |
| hIgG1 | 44 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG | |
| IgG2 | 45 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCCVECPPCPAPPVAGPSVFLFPPKPKDTLMISRTPEVTCV VVDVSHEDPEVQFNWYVDGVEVHNAKTKPREEQFNSTFRVVSVLTVV HQDWLNGKEYKCKVSNKGLPAPIEKTISKTKGQPREPQVYTLPPSRE EMTKNQVSLTCLVKGFYPSDIAVEWESNGQPENNYKTTPPMLDSDGS FFLYSKLTVDKSRWQQGNVFSCSVMHEALHNHYTQKSLSLSP | |
| hIgG4 | 46 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLMISRTPEVTC | |

TABLE 2-continued

| | SEQ ID NO | Fc chain sequence |
|---|---|---|
| Name | | |
| | | VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| IgG4-SP (S228P) | 47 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| IgG4-SPLE (S228P/ L235E) | 48 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEELGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| hIgG1-N297A | 49 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-D265A | 50 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALA (L234A/ L235A) | 51 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LAGA (L235A/ G237A) | 52 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALAGA (L234A/ L235A/ G237A) | 53 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALAPG (L234A/ L235A/ P329G) | 54 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-YTE (M252Y/ S254T/ T256E) | 55 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYITREPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP |

TABLE 2-continued

Exemplary Fc Sequences

| Name | SEQ ID NO | Fc chain sequence |
|------|-----------|-------------------|
| | | PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-N297A/YTE | 56 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYITREPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-D265A/YTE | 57 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYITREPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALA/YTE | 58 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLYITREPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LAGA/YTE | 59 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLYITREPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALAGA/YTE | 60 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLYITREPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALALAPG/YTE | 61 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLYITREPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LS (M428L/N434S) | 62 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-N297A/LS | 63 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-D265A/LS | 64 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |

TABLE 2-continued

Exemplary Fc Sequences

| Name | SEQ ID NO | Fc chain sequence |
|---|---|---|
| hIgG1-LALA/LS | 65 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-LAGA/LS | 66 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-LALAGA/LS | 67 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-LALAPG/LS | 68 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHSHYTQKSLSLSPG |
| hIgG1-DHS (L309D/ Q311H/ N434S) | 69 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG1-N297A/DHS | 70 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG1-D265A/DHS | 71 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG1-LALA/DHS | 72 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG1-LAGA/DHS | 73 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |

TABLE 2-continued

Exemplary Fc Sequences

| Name | SEQ ID NO | Fc chain sequence |
|------|-----------|-------------------|
| hIgG1-LALAGA/DHS | 74 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVDHHDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG1-LALAPG/DHS | 75 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVDHHDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHSHYTQKSLSLSPG |
| hIgG4-YTE | 76 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLYITREPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| hIgG4-SP/YTE | 77 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLYITREPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| hIgG4-SPLE/YTE | 78 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEELGGPSVFLFPPKPKDTLYITREPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| hIgG4-LS | 79 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVLHEALHSHYTQKSLSLSLGK |
| hIgG4-SP/LS | 80 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVLHEALHSHYTQKSLSLSLGK |
| hIgG4-SPLE/LS | 81 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEELGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVLHEALHSHYTQKSLSLSLGK |
| hIgG4-DHS | 82 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLMISRTPEVTC VVVDVSQEDPEVQFNWYVDGVEVHNAKTKPREEQFNSTYRVVSVLTV DHHDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHSHYTQKSLSLSLGK |

TABLE 2-continued

Exemplary Fc Sequences

| Name | SEQ ID NO | Fc chain sequence |
|---|---|---|
| hIgG4-SP/DHS | 83 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTC VVVDVSQEDPEVQFNWYVDGVEVHNAKTKPREEQFNSTYRVVSVLTV DHHDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHSHYTQKSLSLSLGK |
| hIgG4-SPLE/DHS | 84 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEELGGPSVFLFPPKPKDTLMISRTPEVTC VVVDVSQEDPEVQFNWYVDGVEVHNAKTKPREEQFNSTYRVVSVLTV DHHDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHSHYTQKSLSLSLGK |
| hIgG2-YTE | 85 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCCVECPPCPAPPVAGPSVFLFPPKPKDTLYITREPEVTCV VVDVSHEDPEVQFNWYVDGVEVHNAKTKPREEQFNSTFRVVSVLTVV HQDWLNGKEYKCKVSNKGLPAPIEKTISKTKGQPREPQVYTLPPSRE EMTKNQVSLTCLVKGFYPSDIAVEWESNGQPENNYKTTPPMLDSDGS FFLYSKLTVDKSRWQQGNVFSCSVLHEALHSHYTQKSLSLSP |
| hIgG2-LS | 86 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCCVECPPCPAPPVAGPSVFLFPPKPKDTLMISRTPEVTCV VVDVSHEDPEVQFNWYVDGVEVHNAKTKPREEQFNSTFRVVSVLTVV HQDWLNGKEYKCKVSNKGLPAPIEKTISKTKGQPREPQVYTLPPSRE EMTKNQVSLTCLVKGFYPSDIAVEWESNGQPENNYKTTPPMLDSDGS FFLYSKLTVDKSRWQQGNVFSCSVLHEALHSHYTQKSLSLSP |
| hIgG2-DHS | 87 | ASTKGPSVFPLAPCSRSTSESTAALGCLVKDYFPEPVTVSWNSGALT SGVHTFPAVLQSSGLYSLSSVVTVPSSNFGTQTYTCNVDHKPSNTKV DKTVERKCCVECPPCPAPPVAGPSVFLFPPKPKDTLMISRTPEVTCV VVDVSHEDPEVQFNWYVDGVEVHNAKTKPREEQFNSTFRVVSVLTVD HHDWLNGKEYKCKVSNKGLPAPIEKTISKTKGQPREPQVYTLPPSRE EMTKNQVSLTCLVKGFYPSDIAVEWESNGQPENNYKTTPPMLDSDGS FFLYSKLTVDKSRWQQGNVFSCSVMHEALHSHYTQKSLSLSP |
| IgG4-SP | 88 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPPCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| hIgG1-LA | 89 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-N297A/LA | 90 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-D265A/LA | 91 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |

TABLE 2-continued

Exemplary Fc Sequences

| Name | SEQ ID NO | Fc chain sequence |
|---|---|---|
| hIgG1-LALA/LA | 92 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-LAGA/LA | 93 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-LALAGA/LA | 94 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-LALAPG/LA | 95 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHAHYTQKSLSLSPG |
| hIgG1-N434A | 96 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-N297A/N434A | 97 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-D265A/N434A | 98 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-LALA/N434A | 99 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-LAGA/N434A | 100 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |

TABLE 2-continued

| | | Exemplary Fc Sequences |
|---|---|---|
| Name | SEQ ID NQ | Fc chain sequence |

| Name | SEQ ID NQ | Fc chain sequence |
|---|---|---|
| hIgG1-LALALAGA/N434A | 101 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-LALALAPG/N434A | 102 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHAHYTQKSLSLSPG |
| hIgG1-N434W | 103 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-N297A/N434W | 104 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-D265A/N434W | 105 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRTPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-LALA/N434W | 106 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-LAGA/N434W | 107 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-LALALAGA/N434W | 108 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |
| hIgG1-LALALAPG/N434W | 109 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHWHYTQKSLSLSPG |

TABLE 2-continued

| | | |
|---|---|---|
| | | Exemplary Fc Sequences |

| Name | SEQ ID NQ | Fc chain sequence |
|---|---|---|
| hIgG1/DQ (T256D/ T307Q) | 110 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVHNAKTKPREEQYNSTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-N297A/DQ | 111 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVHNAKTKPREEQYASTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-D265A/DQ | 112 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVAVSHEDPEVKFNWYVDGVEVHNAKTKPREEQYNSTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LALA/DQ | 113 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRDPE<br>VTCVVVDVSHEDPEVKFNWYVDGVEVHNAKTKPREEQYNSTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LAGA/DQ | 114 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELAGAPSVFLFPPKPKDTLMISRDPE<br>VTCVVVDVSHEDPEVKFNWYVDGVEVHNAKTKPREEQYNSTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LALAGA/ DQ | 115 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRDPE<br>VTCVVVDVSHEDPEVKFNWYVDGVEVHNAKTKPREEQYNSTYRVVSV<br>LQVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LALAPG/ DQ | 116 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRDPE<br>VTCVVVDVSHEDPEVKFNWYVDGVEVHNAKTKPREEQYNSTYRVVSV<br>LQVLHQDWLNGKEYKCKVSNKALGAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1/DW (T256D/ T307W) | 117 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVHNAKTKPREEQYNSTYRVVSV<br>LWVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-N297A/DW | 118 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVHNAKTKPREEQYASTYRVVSV<br>LWVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |

TABLE 2-continued

| | | Exemplary Fc Sequences |
|---|---|---|
| Name | SEQ ID NO | Fc chain sequence |
| hIgG1-D265A/DW | 119 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLMISRDPE VTCVVVAVSHEDPEVKFNWYVDGVEVHNAKTKPREEQYNSTYRVVSV LWVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALA/DW | 120 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRDPE VTCVVVDVSHEDPEVKFNWYVDGVEVHNAKTKPREEQYNSTYRVVSV LWVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LAGA/DW | 121 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELAGAPSVFLFPPKPKDTLMISRDPE VTCVVVDVSHEDPEVKFNWYVDGVEVHNAKTKPREEQYNSTYRVVSV LWVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALAGA/DW | 122 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGAPSVFLFPPKPKDTLMISRDPE VTCVVVDVSHEDPEVKFNWYVDGVEVHNAKTKPREEQYNSTYRVVSV LWVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALAPG/DW | 123 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRDPE VTCVVVDVSHEDPEVKFNWYVDGVEVHNAKTKPREEQYNSTYRVVSV LWVLHQDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1/YD (M252Y/T256D) | 124 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYISRDPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-N297A/YD | 125 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYISRDPE VTCVVVDVSHEDPEVKFNWYVDGVEVHNAKTKPREEQYASTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-D265A/YD | 126 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPELLGGPSVFLFPPKPKDTLYISRDPE VTCVVVAVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |
| hIgG1-LALA/YD | 127 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLYISRDPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVMHEALHNHYTQKSLSLSPG |

TABLE 2-continued

| | | |
|---|---|---|

Exemplary Fc Sequences

| Name | SEQ ID NO | Fc chain sequence |
|---|---|---|
| hIgG1-LAGA/YD | 128 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELAGAPSVFLFPPKPKDTLYISRDPE<br>VTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LALAGA/YD | 129 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGAPSVFLFPPKPKDTLYISRDPE<br>VTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1-LALAPG/YD | 130 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLYISRDPE<br>VTCVVVDVSHEDPEVKFNWYVDGVEVHNAKTKPREEQYNSTYRVVSV<br>LTVLHQDWLNGKEYKCKVSNKALGAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG |
| hIgG1/QVV (T307Q/Q311V/A378V) | 131 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-N297A/QVV | 132 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVDVSHEDPEVKFNWYVDGVEVHNAKTKPREEQYASTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-D265A/QVV | 133 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVAVSHEDPEVKFNWYVDGVEVHNAKTKPREEQYNSTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LALA/QVV | 134 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRTPE<br>VTCVVVDVSHEDPEVKFNWYVDGVEVHNAKTKPREEQYNSTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LAGA/QVV | 135 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELAGAPSVFLFPPKPKDTLMISRTPE<br>VTCVVVDVSHEDPEVKFNWYVDGVEVHNAKTKPREEQYNSTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LALALAGA/QVV | 136 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRTPE<br>VTCVVVDVSHEDPEVKFNWYVDGVEVHNAKTKPREEQYNSTYRVVSV<br>LQVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |

TABLE 2-continued

Exemplary Fc Sequences

| Name | SEQ ID NO | Fc chain sequence |
| --- | --- | --- |
| hIgG1-LALAPG/QVV | 137 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRTPE<br>VTCVVVDVSHEDPEVKFNWYVDGVEVHNAKTKPREEQYNSTYRVVSV<br>LQVLHVDWLNGKEYKCKVSNKALGAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1/DDRVV (T256D/N286D/T307R/Q311V/A378V) | 138 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVDNAKTKPREEQYNSTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-N297A/DDRVV | 139 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVDVSHEDPEVKFNWYVDGVEVDNAKTKPREEQYASTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-D265A/DDRVV | 140 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRDPE<br>VTCVVVAVSHEDPEVKFNWYVDGVEVDNAKTKPREEQYNSTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LALA/DDRVV | 141 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRDPE<br>VTCVVVDVSHEDPEVKFNWYVDGVEVDNAKTKPREEQYNSTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LAGA/DDRVV | 142 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELAGAPSVFLFPPKPKDTLMISRDPE<br>VTCVVVDVSHEDPEVKFNWYVDGVEVDNAKTKPREEQYNSTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LALAGA/DDRVV | 143 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRDPE<br>VTCVVVDVSHEDPEVKFNWYVDGVEVDNAKTKPREEQYNSTYRVVSV<br>LRVLHVDWLNGKEYKCKVSNKALPAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-LALAPG/DDRVV | 144 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRDPE<br>VTCVVVDVSHEDPEVKFNWYVDGVEVDNAKTKPREEQYNSTYRVVSV<br>LRVLHVDWLNGKEYKCKVSNKALGAPIEKTISKAKGQPREPQVYTLP<br>PSRDELTKNQVSLTCLVKGFYPSDIVVEWESNGQPENNYKTTPPVLD<br>SDGSFFLYSKLTVDKSRWQQGNVFSCSVMHEALHNHYTQKSLSLSPG |
| hIgG1-Q311R/M428L | 145 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |

TABLE 2-continued

Exemplary Fc Sequences

| Name | SEQ ID NQ | Fc chain sequence |
|---|---|---|
| hIgG4-Q311R/M428L | 146 | ASTKGPSVFPLAPCSRSTSESTAALGCLVKDYFPEPVTVSWNSGALT<br>SGVHTFPAVLQSSGLYSLSSVVTVPSSSLGTKTYTCNVDHKPSNTKV<br>DKRVESKYGPPCPSCPAPEFLGGPSVFLFPPKPKDTLMISRTPEVTC<br>VVVDVSQEDPEVQFNWYVDGVEVHNAKTKPREEQFNSTYRVVSVLTV<br>LHRDWLNGKEYKCKVSNKGLPSSIEKTISKAKGQPREPQVYTLPPSQ<br>EEMTKNQVSLTCLVKGFYPSDIAVEWESNGQPENNYKTTPPVLDSDG<br>SFFLYSRLTVDKSRWQEGNVFSCSVLHEALHNHYTQKSLSLSLGK |
| IgG4-SP/Q311R/M428L | 147 | ASTKGPSVFPLAPCSRSTSESTAALGCLVKDYFPEPVTVSWNSGALT<br>SGVHTFPAVLQSSGLYSLSSVVTVPSSSLGTKTYTCNVDHKPSNTKV<br>DKRVESKYGPPCPPCPAPEFLGGPSVFLFPPKPKDTLMISRTPEVTC<br>VVVDVSQEDPEVQFNWYVDGVEVHNAKTKPREEQFNSTYRVVSVLTV<br>LHRDWLNGKEYKCKVSNKGLPSSIEKTISKAKGQPREPQVYTLPPSQ<br>EEMTKNQVSLTCLVKGFYPSDIAVEWESNGQPENNYKTTPPVLDSDG<br>SFFLYSRLTVDKSRWQEGNVFSCSVLHEALHNHYTQKSLSLSLGK |
| IgG4-SPLE/Q311R/M428L | 148 | ASTKGPSVFPLAPCSRSTSESTAALGCLVKDYFPEPVTVSWNSGALT<br>SGVHTFPAVLQSSGLYSLSSVVTVPSSSLGTKTYTCNVDHKPSNTKV<br>DKRVESKYGPPCPPCPAPEELGGPSVFLFPPKPKDTLMISRTPEVTC<br>VVVDVSQEDPEVQFNWYVDGVEVHNAKTKPREEQFNSTYRVVSVLTV<br>LHRDWLNGKEYKCKVSNKGLPSSIEKTISKAKGQPREPQVYTLPPSQ<br>EEMTKNQVSLTCLVKGFYPSDIAVEWESNGQPENNYKTTPPVLDSDG<br>SFFLYSRLTVDKSRWQEGNVFSCSVLHEALHNHYTQKSLSLSLGK |
| IgG2-Q311R/M428L | 149 | ASTKGPSVFPLAPCSRSTSESTAALGCLVKDYFPEPVTVSWNSGALT<br>SGVHTFPAVLQSSGLYSLSSVVTVPSSNFGTQTYTCNVDHKPSNTKV<br>DKTVERKCCVECPPCPAPPVAGPSVFLFPPKPKDTLMISRTPEVTCV<br>VVDVSHEDPEVQFNWYVDGVEVHNAKTKPREEQFNSTFRVVSVLTVV<br>HRDWLNGKEYKCKVSNKGLPAPIEKTISKTKGQPREPQVYTLPPSRE<br>EMTKNQVSLTCLVKGFYPSDIAVEWESNGQPENNYKTTPPMLDSDGS<br>FFLYSKLTVDKSRWQQGNVFSCSVLHEALHNHYTQKSLSLSP |
| hIgG1-N297A/Q311R/M428L | 150 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVDVSHEDPEVKFNWYVDGVEVHNAKTKPREEQYASTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |
| hIgG1-D265A/Q311R/M428L | 151 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELLGGPSVFLFPPKPKDTLMISRTPE<br>VTCVVVAVSHEDPEVKFNWYVDGVEVHNAKTKPREEQYNSTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |
| hIgG1-LALA/Q311R/M428L | 152 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGGPSVFLFPPKPKDTLMISRTPE<br>VTCVVVDVSHEDPEVKFNWYVDGVEVHNAKTKPREEQYNSTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |
| hIgG1-LAGA/Q311R/M428L | 153 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPELAGAPSVFLFPPKPKDTLMISRTPE<br>VTCVVVDVSHEDPEVKFNWYVDGVEVHNAKTKPREEQYNSTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |
| hIgG1-LALALAGA/Q311R/M428L | 154 | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKKVEPKSCDKTHTCPPCPAPEAAGAPSVFLFPPKPKDTLMISRTPE<br>VTCVVVDVSHEDPEVKFNWYVDGVEVHNAKTKPREEQYNSTYRVVSV<br>LTVLHRDWLNGKEYKCKVSNKALPAPIEKTISKAKGQPREPQVYTLP<br>PSRDELTKNQVSLTCLVKGFYPSDIAVEWESNGQPENNYKTTPPVLD<br>SDGSFFLYSKLTVDKSRWQQGNVFSCSVLHEALHNHYTQKSLSLSPG |

TABLE 2-continued

Exemplary Fc Sequences

| Name | SEQ ID NO | Fc chain sequence |
|------|-----------|-------------------|
| hIgG1-LALAPG/Q311R/M428L | 155 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHRDWLNGKEYKCKVSNKALGAPIEKTISKAKGQPREPQVYTLP PSRDELTKNQVSLTCLVKGFYPSDIAVEWESNGQPENNYKTTPPVLD SDGSFFLYSKLTVDKSRWQQGNVFSCSVLHEALHNHYTQKSLSLSPG |

In some embodiments, the IL-23 binding protein comprises an Fc region comprising one or more modifications in SEQ ID NO: 44. In some embodiments, the IL-23 binding protein comprises an Fc region comprising one or more modifications in SEQ ID NO: 45. In some embodiments, the IL-23 binding protein comprises an Fc region comprising one or more modifications in SEQ ID NO: 46. In some embodiments, the Fc region comprises an Fc chain whose amino acid sequence has at least 80%, at least 85%, at least 90%, at least 95%, at least 96%, at least 97%, at least 98%, or at least 99% sequence identity with the amino acid sequence according to any one of SEQ ID NOs: 44-46. In some embodiments, the Fc region comprises an Fc chain whose amino acid sequence is according to any one of SEQ ID NOs: 44-46.

In certain embodiments, IL-23 binding proteins comprise an Fc region ("modified Fc region") with at least one amino acid modification relative to a wild-type Fc region. IL-23 binding proteins with a modified Fc region may comprise mutations in one Fc chain, or in multiple Fc chains (e.g., when two or more Fc chains are present). Within an IL-23 binding protein with modifications in multiple Fc chains, the modifications on each Fc chain may be the same or different. In some embodiments the modified Fc region comprises a half-life extending mutation or set of mutations, e.g., M252Y, S254T, and T256E (YTE) and/or M428L and N434S (LS).

In some embodiments, the modified Fc region comprises a modification selected from the group consisting of: S298A, E333A, K334A, K326A, F243L, R292P, Y300L, V305I, P396L, F243L, R292P, Y300L, L235V, P396L, F243L, S239D, I332E, A330L, S267E, L328F, D265S, S239E, K326A, A327H, G237F, K326E, G236A, D270L, H268D, S324T, L234F, N325L, V266L, S267D, and combinations thereof. In some embodiments, the modified Fc region comprises a modification selected from the group consisting of S228P, M252Y, S254T, T256E, T256D, T250Q, H285D, T307A, T307Q, T307R, T307W, L309D, Q411H, Q311V, A378V, E380A, M428L, N434A, N434S, N297A, D265A, L234A, L235A, N434W, and combinations thereof.

In some embodiments, the modified Fc region comprises a specific combination of amino acid substitutions selected from the group consisting of: L234A/L235A; V234A/G237A; L235A/G237A/E318A; S228P/L236E; H268Q/V309L/A330S/A331S; C220S/C226S/C229S/P238S; C226S/C229S/E3233P/L235V/L235A; L234F/L235E/P331S; C226S/P230S; L234A/G237A; L234A/L235A/G237A; Q311R/M428L; L234A/L235A/P329G; and combinations thereof.

In some embodiments, the modified Fc region comprises a specific combination of amino acid substitutions selected from the group consisting of M428L/N434S (LS); M252Y/S254T/T256E (YTE); T250Q/M428L; T307A/E380A/N434A; T256D/T307Q (DQ); T256D/T307W (DW); M252Y/T256D (YD); T307Q/Q311V/A378V (QVV); T256D/H285D/T307R/Q311V/A378V (DDRVV); L309D/Q311H/N434S (DHS); S228P/L235E (SPLE); L234A/L235A (LALA); M428L/N434A (LA); L234A/G237A (LAGA); L234A/L235A/G237A (LALAGA); L234A/L235A/P329G (LALAPG); N297A/YTE; D265A/YTE; LALA/YTE; LAGA/YTE; LALAGA/YTE; LALAPG/YTE; N297A/LS; D265A/LS; LALA/LS; LAGA/LS; LALAGA/LS; LALAPG/LS; N297A/DHS; D265A/DHS; LALA/DHS; LAGA/DHS; LALAGA/DHS; LALAPG/DHS; SP/YTE; SPLE/YTE; SP/LS; SPLE/LS; SP/DHS; SPLE/DHS; N297A/LA; D265A/LA; LALA/LA; LAGA/LA; LALAGA/LA; LALAPG/LA; N297A/N434A; D265A/N434A; LALA/N434A; LAGA/N434A; LALAGA/N434A; LALAPG/N434A; N297A/N434W; D265A/N434W; LALA/N434W; LAGA/N434W; LALAGA/N434W; LALAPG/N434W; N297A/DQ; D265A/DQ; LALA/DQ; LAGA/DQ; LALAGA/DQ; LALAPG/DQ; N297A/DW; D265A/DW; LALA/DW; LAGA/DW; LALAGA/DW; LALAPG/DW; N297A/YD; D265A/YD; LALA/YD; LAGA/YD; LALAGA/YD; LALAPG/YD; N297A/QVV; D265A/QVV; LALA/QVV; LAGA/QVV, LALAGA/QVV; LALAPG/QVV; N297A/DDRVV; D265A/DDRVV; LALA/DDRVV; LAGA/DDRVV; LALAGA/DDRVV; LALAPG/DDRVV; SP/Q311R/M428L; SPLE/Q311R/M428L; N297A/Q311R/M428L; D265A/Q311R/M428L; LALA/Q311R/M428L; LAGA/Q311R/M428L; LALAGA/Q311R/M428L; LALAPG/Q311R/M428L; and combinations thereof. In some embodiments, the modified Fc region comprises a specific combination of amino acid substitutions selected from the group consisting of M428L/N434S (LS) and M252Y/S254T/T256E (YTE). In some embodiments, the modified Fc region comprises M428L/N434S (LS) (e.g., SEQ ID NO: 62, SEQ ID NO: 79, SEQ ID NO: 86) modifications. In some embodiments, the modified Fc region comprises M252Y/S254T/T256E (YTE) (e.g., SEQ ID NO: 55, SEQ ID NO: 76, SEQ ID NO: 85) modifications.

In some embodiments, IL-23 binding proteins described herein include modifications to improve their ability to mediate effector function. Such modifications are known in the art and include afucosylation, or engineering of the affinity of the Fc region towards an activating receptor, mainly FCGR3a for antibody-dependent cellular cytotoxicity (ADCC), and towards C1q for complement-dependent cytotoxicity (CDC).

In some embodiments, the Fc region comprises one or more amino acid substitutions, wherein the one or more substitutions result in a decrease in one or more of ADCC activity, ADCP activity, or CDC activity compared with the Fc without the one or more substitutions.

In some aspects, an antibody provided herein comprises an Fc region (e.g., an IgG1 Fc region) with reduced fucose content at position Asn 297 (EU numbering) compared to a naturally occurring Fc region. Such Fc regions are known to confer improved ADCC activity to the binding proteins which comprise them. In some aspects, such binding proteins do not comprise any fucose at position Asn 297.

In some embodiments, IL-23 binding proteins described herein comprise an Fc region with one or more amino acid substitutions which improve ADCC, such as a substitution at one or more of positions 298, 333, and 334 of an Fc chain. In some embodiments, an antibody provided herein comprises an Fc region with one or more amino acid substitutions at positions 239, 332, and 330.

In some embodiments, the Fc region comprises an Fc chain whose amino acid sequence has at least 80%, at least 85%, at least 90%, at least 95%, at least 96%, at least 97%, at least 98%, or at least 99% sequence identity with the amino acid sequence according to any one of SEQ ID NOs: 44-155. In some embodiments, the Fc region comprises an Fc chain whose amino acid sequence is according to any one of SEQ ID NOs: 44-155.

In some embodiments, IL-23 binding proteins described herein comprise an Fc region with at least one galactose residue in the oligosaccharide attached to the Fc region. Such antibody variants may have improved CDC function.

In some embodiments, IL-23 binding proteins described herein comprise one or more alterations that improve or diminish C1q binding and/or CDC.

In certain embodiments, IL-23 binding proteins comprise an Fc region with one or more amino acid substitutions, wherein the one or more substitutions result in an increase in antibody half-life, and a decrease in one or more of ADCC activity, ADCP activity, or CDC activity compared with a comparable IL-23 binding protein whose Fc region lacks the one or more substitutions. In certain embodiments, the one or more amino acid substitutions results in increased binding protein half-life at pH 6.0 compared to binding protein comprising a wild-type Fc region. In certain embodiments, the antibody has an increased half-life that is about 10,000-fold, 1,000-fold, 500-fold, 100-fold, 50-fold, 20-fold, 10-fold, 9-fold, 8-fold, 7-fold, 6-fold, 5-fold, 4.5-fold, 4-fold, 3.5-fold, 3-fold, 2.5-fold, 2-fold, 1.95-fold, 1.9-fold, 1.85-fold, 1.8-fold, 1.75-fold, 1.7-fold, 1.65-fold, 1.6-fold, 1.55-fold, 1.50-fold, 1.45-fold, 1.4-fold, 1.35-fold, 1.3-fold, 1.25-fold, 1.2-fold, 1.15-fold, 1.1-fold, or 1.05-fold longer compared to an antibody comprising a wild-type Fc region.

In certain embodiments, IL-23 binding proteins comprise an Fc region which comprise one or more amino acid substitutions, wherein the one or more substitutions result in a decrease in one or more of ADCC activity, ADCP activity, or CDC activity compared comparable IL-23 binding protein whose Fc region lacks the one or more substitutions.

In certain embodiments, the Fc region binds an Fcγ Receptor selected from the group consisting of: FcγRI, FcγRIIa, FcγRIIb, FcγRIIc, FcγRIIIa, and FcγRIIIb. In certain embodiments, the Fc region binds an Fcγ Receptor with higher affinity at pH 6.0 compared to an antibody comprising a wild-type Fc region.

In some embodiments, the IL-23 binding proteins comprise an extended half-life (i.e., serum half-life), e.g., in human serum or in humans. In some embodiments, the IL-23 binding proteins comprise a half-life of at least about 14, 28, 42, 56, 70, 84, 96, or more than 96 weeks. In some embodiments, the IL-23 binding proteins comprise a half-life in a range of about 14 days to about 96 days, about 14 days to about 84 days, about 14 days to about 70 days, about 14 days to about 56 days, about 14 days to about 42 days, about 14 days to about 28 days, of about 28 days to about 96 days, about 28 days to about 84 days, about 28 days to about 70 days, about 28 days to about 56 days, about 28 days to about 42 days, of about 42 days to about 96 days, about 42 days to about 84 days, about 42 days to about 70 days, or about 42 days to about 56 days. In some embodiments, the IL-23 binding proteins comprise a half-life in a range of about 42 days to about 56 days. In some embodiments, the IL-23 binding proteins comprise a half-life in a range of about 74 days to about 93 days. In some embodiments, the IL-23 binding proteins comprise a half-life of at least about 50 days, at least about 55 days, at least about 60 days, at least about 65 days, at least about 70 days, at least about 75 days, at least about 80 days, at least about 85 days, at least about 90 days, or at least about 93 days. In some embodiments, the IL-23 binding proteins comprise a half-life of about 50 days, about 55 days, about 60 days, about 65 days, about 70 days, about 75 days, about 80 days, about 85 days, about 90 days, about 93 days or about 100 days. Methods of measuring half-life are known in the art. In some embodiments, the half-life is measured in a non-human primate. In some embodiments, the half-life is measured in a human. In some embodiments, the half-life is measured following intravenous administration. In some embodiments, the half-life is measured following subcutaneous administration.

In some embodiments, IL-23 binding proteins described herein have a half-life that is at least 20% longer than a reference binding protein. In some embodiments, the half-life of IL-23 binding proteins described herein is at least 30%, at least 40%, at least 50%, at least 60%, at least 70%, at least 80%, or at least 90% longer than the half-life of the reference binding protein. In some embodiments, the half-life of the IL-23 binding proteins described herein is longer than the half-life of the reference binding protein by at least 2 fold, at least 3 fold, at least 4 fold, at least 5 fold, at least 6 fold, at least 7 fold, at least 8 fold, at least 9 fold, or at least 10 fold.

Antibody Fragments

In certain embodiments, provided are antibody fragments, rather than whole antibodies.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the production of large amounts of these fragments. Antibody fragments can be isolated from, e.g., antibody phage libraries. Alternatively or additionally, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. Fab and F(ab')2 fragment with increased in vivo half-life comprising a salvage receptor binding epitope residues are described, e.g., in U.S. Pat. No. 5,869,046. Other techniques for the production of antibody fragments will be apparent to the skilled practitioner.

In some embodiments, the antigen-binding fragment is a single chain Fv fragment (scFv). See, e.g., WO 93/16185; U.S. Pat. Nos. 5,571,894; and 5,587,458. Fv and scFv are species with intact combining sites that are devoid of constant regions; thus, these fragments may be suitable for reduced nonspecific binding during in vivo use. scFv fusion proteins may be constructed to yield fusion of an effector protein at either the amino or the carboxy terminus of an scFv. See, e.g., Antibody Engineering, ed. Borrebaeck. An antigen-binding antibody fragment may also be a "linear antibody", e.g., as described in U.S. Pat. No. 5,641,870.

Vectors, Host Cells and Recombinant Methods

Also provided are isolated nucleic acids encoding IL-23 binding proteins (e.g., antibodies and antigen-binding fragments), vectors and host cells comprising the nucleic acid, and recombinant techniques for the production of the antibody.

For recombinant production of the antibody or antigen-binding fragment, a nucleic acid encoding the antibody or antigen-binding fragment may be isolated and inserted into a replicable vector for further cloning (amplification of the DNA) or for expression. DNA encoding the monoclonal antibody can be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Pharmaceutical Compositions

The present disclosure also includes pharmaceutical compositions that contain therapeutically effective amounts of the IL-23 binding proteins or methods using such pharmaceutical compositions.

In certain embodiments, provided antibodies are incorporated together with one or more pharmaceutically acceptable carriers into a pharmaceutical composition suitable for administration to a subject. As used herein, "pharmaceutically acceptable carrier" refers to any of a variety of solvents, dispersion media, coatings, antibacterial and antifungal agents, isotonic and absorption delaying agents, and the like that are physiologically compatible. Examples of pharmaceutically acceptable carriers include, but are not limited to, water, saline, phosphate buffered saline, dextrose, glycerol, ethanol and the like, as well as combinations thereof.

In some embodiments, pharmaceutical compositions comprise one or more tonicity agents or stabilizers. Non-limiting examples of such tonicity agents or stabilizers include sugars (e.g., sucrose), polyalcohols (e.g., mannitol or sorbitol), and sodium chloride.

In some embodiments, pharmaceutical compositions comprise one or more bulking agents and/or lyoprotectants (e.g., mannitol or glycine), buffers (e.g., phosphate, acetate, or histidine buffers), surfactants (e.g., polysorbates), antioxidants (e.g., methionine), and/or metal ions or chelating agents (e.g., ethylenediaminetetraacetic acid (EDTA)).

In some embodiments, pharmaceutical compositions comprise one or more auxiliary substances such as wetting or emulsifying agents, preservatives (e.g., benzyl alcohol) or buffers, which may enhance the shelf life and/or effectiveness of antibodies disclosed herein.

A detergent or surfactant may also be added to a pharmaceutical composition. Exemplary detergents include non-ionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In some embodiments, the formulation may include a surfactant which is a polysorbate. In some embodiments, the formulation may contain the detergent polysorbate 80 or Tween 20. Tween 20 is a term used to describe polyoxyethylene (20) sorbitanmonooleate (see Fiedler, Lexikon der Hifsstoffe, Editio Cantor Verlag Aulendorf, 4th edi., 1996).

Pharmaceutical compositions may be provided in any of a variety of forms. These include, for example, liquid, semi-solid and solid dosage forms, such as liquid solutions (e.g., injectable and infusible solutions), dispersions or suspensions, tablets, pills, powders, liposomes and suppositories. Suitability of certain forms may depend on the intended mode of administration and therapeutic application.

In some embodiments, the pharmaceutical composition is a liquid composition. In some embodiments, the pharmaceutical composition is formulated for subcutaneous administration. In some embodiments, the pharmaceutical composition is formulated for intravenous administration. In some embodiments, the liquid composition contains at least about 100 mg/mL, at least about 125 mg/mL or at least about 150 mg/mL of an IL-23 binding antibody.

In some embodiments, pharmaceutical compositions are in the form of injectable or infusible solutions. In some embodiments, the injectable or infusible solution is suitable for intravenous injection or infusion. In some embodiments, the injectable or infusible solution is suitable for subcutaneous injection or infusion.

In some embodiments, the injectable dosage form comprises at least about 100 mg/mL, at least 125 mg/mL or at least about 150 mg/mL of an IL-23 binding antibody. For example, the injectable dosage form comprises from at least about 100 mg/mL to at least 110 mg/mL, from at least about 110 mg/mL to at least 120 mg/mL, from at least about 120 mg/mL to at least 130 mg/mL, from at least about 130 mg/mL to at least 140 mg/mL, from at least about 140 mg/mL to at least 150 mg/mL of the IL-23 binding antibody.

Pharmaceutical compositions are typically sterile and stable under conditions of manufacture, transport, and storage. Pharmaceutical compositions may be formulated as, for example, a solution, microemulsion, dispersion, liposome, or other ordered structure. In some embodiments, a pharmaceutical composition is formulated as a structure particularly suitable for high drug concentration. For example, sterile injectable solutions can be prepared by incorporating a therapeutic agent (e.g., antibody) in a desired amount in an appropriate solvent with one or a combination of ingredients enumerated herein, optionally followed by sterilization (e.g., filter sterilization). Generally, dispersions may be prepared by incorporating an antibody into a sterile vehicle that contains a basic dispersion medium and other ingredient(s) such as those additional ingredients mentioned herein. In the case of sterile powders for the preparation of sterile injectable solutions, examples of preparation methods include vacuum drying and freeze-drying to yield a powder of the antibody and any additional desired ingredient(s), e.g., from a previously sterile-filtered solution thereof.

Proper fluidity of a solution can be maintained, for example, by the use of a coating such as lecithin, by maintaining certain particle sizes (e.g., in the case of dispersions), and/or by using surfactants. Prolonged absorption of injectable compositions can be brought about, e.g., by including in the composition an agent that delays absorption (for example, monostearate salts and/or gelatin).

The IL-23 binding protein may be lyophilized to produce a lyophilized formulation including the proteins and a lyo-protectant. The lyoprotectant may be sugar, e.g., disaccharides. In some embodiments, the lyoprotectant is sucrose or maltose. The lyophilized formulation may also include one or more of a buffering agent, a surfactant, a bulking agent, and/or a preservative.

Methods of Preparation

The IL-23 binding proteins described herein can be made using recombinant DNA technology well known to a skilled person in the art. For example, one or more isolated poly-nucleotides encoding the IL-23 binding protein can be ligated to other appropriate nucleotide sequences, including, for example, constant region coding sequences, and expression control sequences, to produce conventional gene expression constructs (i.e., expression vectors) encoding the desired IL-23 binding proteins. Production of defined gene constructs is within routine skill in the art.

Nucleic acids encoding desired IL-23 binding proteins can be incorporated (ligated) into expression vectors, which can be introduced into host cells through conventional transfection or transformation techniques. Exemplary host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells that do not otherwise produce IgG protein. Transformed host cells can be grown under conditions that permit the host cells to express the genes that encode IL-23 binding proteins.

Specific expression and purification conditions will vary depending upon the expression system employed. For example, if a gene is to be expressed in *E. coli*, it is first cloned into an expression vector by positioning the engi-neered gene downstream from a suitable bacterial promoter, e.g., Trp or Tac, and a prokaryotic signal sequence. The expressed protein may be secreted. The expressed protein may accumulate in refractile or inclusion bodies, which can be harvested after disruption of the cells by French press or sonication. The refractile bodies can then be solubilized, and the protein may be refolded and/or cleaved by methods known in the art.

If the engineered gene is to be expressed in eukaryotic host cells, e.g., CHO cells, it is first inserted into an expression vector containing a suitable eukaryotic promoter, a secretion signal, a poly A sequence, and a stop codon. Optionally, the vector or gene construct may contain enhanc-ers and introns. In embodiments involving fusion proteins comprising an IL-23 binding protein or portion thereof, the expression vector optionally contains sequences encoding all or part of a constant region, enabling an entire, or a part of, a heavy or light chain to be expressed. The gene construct can be introduced into eukaryotic host cells using conven-tional techniques.

In some embodiments, in order to express an IL-23 binding protein, an N-terminal signal sequence is included in the protein construct. Exemplary N-terminal signal sequences include signal sequences from interleukin-2, CD-5, IgG kappa light chain, trypsinogen, serum albumin, and prolactin.

After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the IL-23 binding proteins.

The IL-23 binding proteins can be isolated and purified using methods known in the art including centrifugation, depth filtration, cell lysis, homogenization, freeze-thawing, affinity purification, gel filtration, ion exchange chromatog-raphy, hydrophobic interaction exchange chromatography, and mixed-mode chromatography.

In some aspects, the disclosure provides a method of treating a patient suffering from a gastrointestinal inflam-matory disease by administering an IL-23 binding protein with an Fc domain, the improvement comprising said Fc region having a modification that extends half-life of the IL-23 binding protein as compared to an IL-23 binding protein that does not comprise the modification. In some embodiments the modification comprises amino acid modi-fications M252Y, S254T, and T256E (YTE) and/or M428L and N434S (LS).

In some aspects, the disclosure provides a method of treating a patient suffering from a gastrointestinal inflam-matory disease by administering an IL-23 binding protein with a heavy chain variable region, the improvement com-prising modification of the framework region sequence of the heavy chain that results in the IL-23 binding protein having an improved binding affinity to IL-23 as compared to a reference antibody having a heavy chain variable region sequence of SEQ ID NO: 156. In some embodiments, the modification results in a heavy chain variable region sequence of SEQ ID NO: 28 and a light chain variable region of SEQ ID NO: 29.

In some aspects, the disclosure provides a method of treating a patient suffering from a gastrointestinal inflam-matory disease by administering an IL-23 binding protein with a heavy chain variable region, the improvement com-prising modification of the complementarity determining regions (CDRs) sequences of the heavy chain that results in the IL-23 binding protein inhibiting activation of STAT3 at a relative $IC_{50}$ of less than 0.90 and inhibiting phosphory-lation of STAT3 at a relative $IC_{50}$ reference of less than 0.80 as compared to a Reference Antibody 1 having CDRs as set forth in Table 3. In some embodiments, the modification results in heavy chain CDR sequences corresponding to CDRs 1, 2, and 3 in Tables 1A, 1B, and 1D.

In some aspects, the disclosure provides a method of treating a gastrointestinal inflammatory disease in a subject comprising a step of administering to the subject a means for binding IL-23 with a Fc portion modified to increase half-life in humans compared to that means for binding IL-23 without such modification. In some embodiments, the modi-fication comprises amino acid modifications M252Y, S254T, and T256E (YTE) and/or M428L and N434S (LS). In some embodiments, the modification increases half-life by a factor of at least two, at least three, or at least four times as compared to the half-life of the IL-23 binding protein without the modification.

In some aspects, the disclosure provides a method of treating a gastrointestinal inflammatory disease in a subject comprising a step of administering to the subject a means for binding IL-23 with a modified framework region sequence of the heavy chain that improves binding affinity to IL-23 as compared to reference antibody having a heavy chain vari-able region sequence of SEQ ID NO: 156. Examples of means for binding human IL-23 include the antibodies or fragments described herein, including the IL-23 binding proteins having certain amino acid sequences of immuno-globulin heavy chain and/or light chains as described herein.

In some embodiments, the modification results in a heavy chain variable region sequence of SEQ ID NO: 28 and a light chain variable region of SEQ ID NO: 29.

In some aspects, the disclosure provides a method of treating a gastrointestinal inflammatory disease in a subject comprising a step of administering to the subject a means for binding IL-23 with a modified complementarity determining region of the heavy chain that inhibits activation of STAT3 at a relative $IC_{50}$ of less than 0.90 and/or inhibits phosphorylation of STAT3 at a relative $IC_{50}$ reference of less than 0.85 relative to a reference antibody having CDRs as set forth in Table 3. In some embodiments, the modification results in heavy chain CDR sequences corresponding to CDRs 1, 2, and 3 in Tables 1A, 1B, and 1D.

In some aspects, the disclosure provides an IL-23 binding protein with an Fc domain, the improvement comprising said Fc region having a modification that extends half-life of the IL-23 binding protein as compared to an IL-23 binding protein that does not comprise the modified Fc region. In some embodiments, the Fc region modification comprises amino acid modifications M252Y, S254T, and T256E (YTE) and/or M428L and N434S (LS)

In some aspects, the disclosure provides an IL-23 binding protein with a heavy chain variable region, the improvement comprising modification of the framework region sequence of the heavy chain that results in the IL-23 binding protein having an improved binding affinity to IL-23 as compared to reference antibody having a heavy chain variable region sequence of SEQ ID NO: 156. In some embodiments, the modification results in a heavy chain variable region sequence of SEQ ID NO: 28 and a light chain variable region of SEQ ID NO: 29.

In some aspects, the disclosure provides an IL-23 binding protein with a heavy chain variable region, the improvement comprising modification of the complementarity determining regions sequences of the heavy chain that results in the IL-23 binding protein inhibiting activation of STAT3 at a relative $IC_{50}$ of less than 0.90 and/or inducing phosphorylation of STAT3 at a relative $IC_{50}$ reference of less than 0.85 relative to a reference antibody having CDRs as set forth in Table 3. In some embodiments, the modification results in heavy chain CDR sequences corresponding to CDRs 1, 2, and 3 in Tables 1A, 1B, and 1D.

In some aspects, the disclosure provides a means for binding IL-23 with a Fc portion modified to increase half-life in humans compared to that means for binding IL-23 without such modification. In some embodiments, the modification comprises amino acid modifications M252Y, S254T, and T256E (YTE) and/or M428L and N434S (LS). In some embodiments, the modification increases half-life by a factor of at least two, at least three, or at least four.

In some aspects, the disclosure provides a means for binding IL-23 having a modified framework region sequence of a heavy chain that results in improved binding affinity to IL-23 as compared to reference antibody having a heavy chain variable region sequence of SEQ ID NO: 156. In some embodiments, the modification results in a heavy chain variable region sequence of SEQ ID NO: 28 and a light chain variable region of SEQ ID NO: 29.

In some aspects, the disclosure provides means for binding IL-23 having a modified complementarity determining region (CDR) of a heavy chain that results in inhibiting activation of STAT3 at a relative $IC_{50}$ of less than 0.90 and/or inhibiting phosphorylation of STAT3 at a relative $IC_{50}$ reference of less than 0.85 relative to a reference antibody having CDRs as set forth in Table 3. In some embodiments, the modification results in heavy chain CDR sequences corresponding to CDRs 1, 2, and 3 in Tables 1A, 1B, and 1D.

In some aspects, the disclosure provides an IL-23 binding protein comprising a means for binding human IL-23 with higher affinity than a reference antibody comprising a heavy chain variable region sequence of SEQ ID NO: 156 and a light chain variable region and a constant region of SEQ ID NO: 2, and a constant region which has been modified to increase in vivo half-life by at least 1, 2 or 3 fold compared to the same binding protein with an unmodified constant region. In some embodiments, the constant region is a human IgG1 region comprising amino acid modifications M252Y, S254T, and T256E (YTE) and/or M428L and N434S (LS).

In another aspect, the disclosure provides the IL-23 binding protein or composition as provided herein for use in treatment of a disease of condition. In another aspect, the disclosure provides use of the IL-23 binding protein or composition as provided herein in a method of treating a disease or condition. In another aspect, the disclosure provides use of the IL-23 binding protein or composition as provided herein in the manufacture of a medicament for treating a disease or condition. In some embodiments, the disease or condition is an inflammatory disease or condition. In some embodiments, the disease or condition is gastrointestinal inflammatory disease. In some embodiments, the disease or condition is inflammatory bowel disease. In some embodiments, the disease or condition is Crohn's disease. In some embodiments, the disease or condition is ulcerative colitis.

EXAMPLES

Example 1. Affinity Maturation of Anti-IL-23p19 Antibody

An anti-human IL-23p19 antibody whose sequences are shown in Table 3 below ("Reference Antibody 1") was used as a parental antibody for further CDR diversification to identify clones with improvements in potency, manufacturability, and pharmacokinetics.

TABLE 3

| Reference Antibody 1 - characteristic sequences CDR sequences shown are according to Kabat. | |
|---|---|
| Heavy chain | Light chain |
| Full sequence: | Full sequence: |
| QVQLVQSGAEVKKPGSSVKVSCKASGYTFTDQ | DIQMTQSPSSLSASVGDRVTITCKASRDVAIAV |
| TIHWMRQAPGQGLEWIGYIYPRDDSPKYNENF | AWYQQKPGKVPKLLIYWASTRHTGVPSRFSGSG |
| KGKVTITADKSTSTAYMELSSLRSEDTAVYYC | SRTDFTLTISSLQPEDVADYFCHQYSSYPFTFG |
| AIPDRSGYAWFIYWGQGTLVTVSSASTKGPSV | SGTKLEIKRTVAAPSVFIFPPSDEQLKSGTASV |
| FPLAPSSKSTSGGTAALGCLVKDYFPEPVTVS | VCLLNNFYPREAKVQWKVDNALQSGNSQESVTE |
| WNSGALTSGVHTFPAVLQSSGLYSLSSVVTVP | QDSKDSTYSLSSTLTLSKADYEKHKVYACEVTH |

TABLE 3-continued

Reference Antibody 1 - characteristic sequences
CDR sequences shown are according to Kabat.

| Heavy chain | Light chain |
|---|---|
| SSSLGTQTYICNVNHKPSNTKVDKRVEPKSCD | QGLSSPVTKSFNRGEC |
| KTHTCPPCPAPEAAGGPSVFLFPPKPKDTLMI | (SEQ ID NO: 174) |
| SRTPEVTCVVVDVSHEDPEVKFNWYVDGVEVH | Variable domain (VL) |
| NAKTKPREEQYNSTYRVVSVLTVLHQDWLNGK | DIQMTQSPSSLSASVGDRVTITCKASRDVAIAV |
| EYKCKVSNKALPAPIEKTISKAKGQPREPQVY | AWYQQKPGKVPKLLIYWASTRHTGVPSRFSGSG |
| TLPPSREEMTKNQVSLTCLVKGFYPSDIAVEW | SRTDFTLTISSLQPEDVADYFCHQYSSYPFTFG |
| ESNGQPENNYKTTPPVLDSDGSFFLYSKLTVD | SGTKLEIK |
| KSRWQQGNVFSCSVMHEALHNHYTQKSLSLSP | (SEQ ID NO: 2) |
| G | CDR-L1: |
| (SEQ ID NO: 173) | KASRDVAIAVA |
| Variable domain (VH) | (SEQ ID NO: 6) |
| QVQLVQSGAEVKKPGSSVKVSCKASGYTFTDQ | CDR-L2: |
| TIHWMRQAPGQGLEWIGYIYPRDDSPKYNENF | WASTRHT |
| KGKVTITADKSTSTAYMELSSLRSEDTAVYYC | (SEQ ID NO: 7) |
| AIPDRSGYAWFIYWGQGTLVTVSS | CDR-L3: |
| (SEQ ID NO: 156) | HQYSSYPFT |
| CDR-H1: | (SEQ ID NO: 8) |
| DQTIH | |
| (SEQ ID NO: 30) | |
| CDR-H2: | |
| YIYPRDDSPKYNENFKG | |
| (SEQ ID NO: 31) | |
| CDR-H3: | |
| PDRSGYAWFIY | |
| (SEQ ID NO: 32) | |

Site-directed PCR mutagenesis was employed to generate distinct libraries for heavy chain CDR1/2 and heavy chain CDR3. Additionally, an additional library consisting of naïve human kappa light chain CDRs was prepared. This approach resulted in three unique libraries. Individual mutants were displayed as Fabs in a phage display system and within each library, mutants were panned through two or three rounds of selection.

For the heavy chain mutant libraries, the first round of selection consisted of 0.01 nM biotinylated human IL-23 (hIL-23) while also being washed for 2 hours at room temperature in buffer containing 1 nM unlabeled hIL-23. The output of that round was subsequently split into four distinct secondary rounds of parallel selection consisting of A) 0.01 nM biotinylated hIL-23 while also being washed for 20 hours at room temperature in buffer containing 10 nM of unlabeled hIL-23, B) 0.001 nM biotinylated hIL-23 while also being washed for 20 hours at room temperature in buffer containing 1 nM of unlabeled hIL-23, C) 0.01 nM biotinylated cynomolgus monkey IL-23 (cyIL-23) while also being washed for 20 hours at room temperature in buffer containing 10 nM of unlabeled cyIL-23, and D) 0.001 nM biotinylated cyIL-23 while also being washed for 20 hours at room temperature in buffer containing 1 nM of unlabeled cyIL-23.

For the light chain mutant libraries, the first round of selection consisted of 10 nM biotinylated hIL-23 while also being washed for 2 hours at room temperature in buffer containing 1000 nM unlabeled hIL-23. The output of that round was subsequently split into two distinct secondary rounds of parallel selection consisting of A) 1 nM biotinylated hIL-23 while also being washed for 16 hours at room temperature in buffer containing 100 nM of unlabeled hIL-23, B) 0.1 nM biotinylated hIL-23 while also being washed for 16 hours at room temperature in buffer containing 10 nM of unlabeled hIL-23. These outputs were then subsequently split into two additional tertiary rounds of parallel selection consisting of A) 0.1 nM biotinylated cyIL-23 while also being washed for 20 hours at room temperature in buffer containing 100 nM of unlabeled cyIL-23 and B) 0.01 nM biotinylated cyIL-23 while also being washed for 20 hours at room temperature in buffer containing 10 nM of unlabeled cyIL-23.

Mutant clones from the output of each arm of secondary and tertiary selection were analyzed for off rate (kd) as a proxy for binding affinity by using periplasmic extracts of each mutant clone through surface plasmon resonance (SPR) using a BIACORE™ 8K+SPR system (Cytiva). Sensor chips (Series S Sensor Chip CM5-Cytiva) were prepared by immobilizing hIL-23 (Acro Biosciences) and interaction with periplasmic extracts was analyzed in order to determine the kd. Bioinformatic analyses of sequences to identify patterns of enrichment were also employed to characterize mutant clones. Mutants that exhibited no loss or improved binding relative to the reference antibody as well as population enrichment throughout the selection were combined into a single library comprising all mutants in both the heavy and light chain.

Clones containing a random combinatorial mix of these individual CDR mutants were again screened in a phage display system, with multiple combinations of selection strategies outlined in Table 4. Mutant clones from the output of each arm of secondary selection were once again analyzed for kd as described.

TABLE 4

| Strategy | Round 1 Selection | Round 2 Selection |
|---|---|---|
| Strategy 1 | Antigen: 0.01 nM biotinylated hIL-23 Wash: 16 hr R.T w/ 1 nM unlabeled hIL- | Antigen: 0.01 nM biotinylated hIL-23 Wash: 48 hr R.T. w/ 1 nM unlabeled hIL-23 |

TABLE 4-continued

| Strategy | Round 1 Selection | Round 2 Selection |
|---|---|---|
| Strategy 2 | Antigen: 0.01 nM biotinylated hIL-23 Wash: 16 hr R.T w/ 1 nM unlabeled hIL-23 | Antigen: 0.001 nM biotinylated hIL-23 Wash: 24 hr R.T. w/ 1 nM unlabeled hIL-23 |
| Strategy 3 | Antigen: 0.01 nM biotinylated hIL-23 Wash: 16 hr R.T w/ 1 nM unlabeled hIL-23 | Antigen: 0.0001 nM biotinylated hIL-23 Wash: 24 hr R.T. w/ 0.1 nM unlabeled hIL-23 |
| Strategy 4 | Antigen: 0.01 nM biotinylated hIL-23 Wash: 16 hr R. T w/ 1 nM unlabeled hIL-23 | Antigen: 0.001 nM biotinylated cyIL-23 Wash: 24 hr R.T. w/ 1 nM unlabeled cyIL-23 |
| Strategy 5 | Antigen: 0.01 nM biotinylated hIL-23 Wash: 16 hr R. T w/ 1 nM unlabeled hIL-23 | Antigen: 0.0001 nM biotinylated cyIL-23 Wash: 24 hr R.T. w/ 0.1 nM unlabeled cyIL-23 |

Mutant clones of interest (clones MAb001 and MAb003) were then reformatted to full antibody format. Briefly, the coding sequences for the heavy chain and light chain of the antibody were generated by DNA synthesis and PCR, then subsequently subcloned into plasmids for protein expression in a mammalian cell system. The gene sequences in the expression vectors were confirmed by DNA sequencing. Antibodies were then purified by a two-step affinity chromatography (Protein A) and size-exclusion chromatography process.

Example 2. Humanization of an Anti-IL-23p19 Antibody

Complementarity-determining region (CDR) grafting technology was used to humanize the parental mouse hybridoma sequence of Reference Antibody 1 (see Table 3 above).

The parental mAb light chain sequence of the mouse hybridoma sequence was compared to a group of human variable region light chain (VK) germline amino acid sequences (Lefranc, M.-P. IMGT, the international ImMu-noGeneTics database; Nucleic Acids Res., 29, D207-209 (2001). DOI: 10.1093/nar/29.1.207. PMID: 11125093). Human germline IGKV3-15 and human germline IGKJ4 were selected.

The parental mAb heavy chain sequence of the mouse hybridoma sequence was compared to a group of human variable region heavy chain (VH) germline amino acid sequences (Lefranc, M.-P. IMGT, the international ImMu-noGeneTics database; Nucleic Acids Res., 29, D207-209 (2001). DOI: 10.1093/nar/29.1.207. PMID: 11125093). Human germline IGKV3-23 and human germline IGHJ6 were selected.

The resulting humanized VL and VH were then combined and reformatted to full antibody format, generating clone mAb002. Briefly, the coding sequences for the heavy chain and light chain of the antibody were generated by DNA synthesis and PCR, then subsequently subcloned into plasmids for protein expression in a mammalian cell system. The gene sequences in the expression vectors were confirmed by DNA sequencing. Antibodies were then purified by a two-step affinity chromatography (Protein A) and size-exclusion chromatography process.

Example 3. Affinity Maturation and Humanization of Anti-IL-23p19 Antibody

Reference Antibody 1 (see Table 3 above) was used as a parental antibody for further CDR diversification to identify clones with improvements in potency, manufacturability, and pharmacokinetics.

Site-directed PCR mutagenesis was employed to generate distinct libraries for heavy chain CDR1/2 and heavy chain CDR3. Additionally, an additional library consisting of naïve human kappa light chain CDRs was prepared. This approach resulted in 3 unique libraries. Individual mutants were displayed as Fabs in a phage display system and within each library, mutants were panned through two or three rounds of selection.

For the heavy chain mutant libraries, the first round of selection consisted of 0.01 nM biotinylated human IL-23 (hIL-23) while also being washed for 2 hours at room temperature in buffer containing 1 nM unlabeled hIL-23. The output of that round was subsequently split into four distinct secondary rounds of parallel selection consisting of A) 0.01 nM biotinylated hIL-23 while also being washed for 20 hours at room temperature in buffer containing 10 nM of unlabeled hIL-23, B) 0.001 nM biotinylated hIL-23 while also being washed for 20 hours at room temperature in buffer containing 1 nM of unlabeled hIL-23, C) 0.01 nM biotinylated cynomolgus monkey IL-23 (cyIL-23) while also being washed for 20 hours at room temperature in buffer containing 10 nM of unlabeled cyIL-23, and D) 0.001 nM biotinylated cyIL-23 while also being washed for 20 hours at room temperature in buffer containing 1 nM of unlabeled cyIL-23.

For the light chain mutant libraries, the first round of selection consisted of 10 nM biotinylated hIL-23 while also being washed for 2 hours at room temperature in buffer containing 1000 nM unlabeled hIL-23. The output of that round was subsequently split into two distinct secondary rounds of parallel selection consisting of A) 1 nM biotinylated hIL-23 while also being washed for 16 hours at room temperature in buffer containing 100 nM of unlabeled hIL-23, B) 0.1 nM biotinylated hIL-23 while also being washed for 16 hours at room temperature in buffer containing 10 nM of unlabeled hIL-23. These outputs were then subsequently split into two additional tertiary rounds of parallel selection consisting of A) 0.1 nM biotinylated cyIL-23 while also being washed for 20 hours at room temperature in buffer containing 100 nM of unlabeled cyIL-23 and B) 0.01 nM biotinylated cyIL-23 while also being washed for 20 hours at room temperature in buffer containing 10 nM of unlabeled cyIL-23.

Mutant clones from the output of each arm of secondary and tertiary selection were analyzed for off rate (kd) as a proxy for binding affinity by using periplasmic extracts of each mutant clone through surface plasmon resonance (SPR) using a BIACORE™ 8K+SPR system (Cytiva). Sensor chips (Series S Sensor Chip CM5—Cytiva) were prepared by immobilizing hIL-23 (Acro Biosciences) and interaction with periplasmic extracts was analyzed in order to determine the kd. Bioinformatic analyses of sequences to identify patterns of enrichment were also employed to characterize mutant clones. Mutants that exhibited no loss or improved binding relative to the reference antibody as well as population enrichment throughout the selection were combined into a single library comprising all mutants in both the heavy and light chain.

Clones containing a random combinatorial mix of these individual CDR mutants were again screened in a phage display system, with multiple combinations of selection strategies outlined in Table 4 in Example 1. Mutant clones from the output of each arm of secondary selection were once again analyzed for kd as described.

Additionally, complementarity-determining region (CDR) grafting technology was used to rehumanize the light chain output of the mutant clones.

The light chain sequence was compared to a group of human variable region light chain (VK) germline amino acid sequences (Lefranc, M.-P. IMGT, the international ImMu-noGeneTics database; Nucleic Acids Res., 29, D207-209 (2001). DOI: 10.1093/nar/29.1.207. PMID: 11125093). Human germline IGKV3-15 and human germline IGKJ4 were selected.

The resulting humanized VL was then combined with the VH with affinity matured heavy chain CDRs reformatted to full antibody format, with the final antibody (antibody clone Mab004) having the VH and VL sequences of SEQ ID NO: 38 and SEQ ID NO: 29, respectively. (See Table 1D.) Briefly, the coding sequences for the heavy chain and light chain of the antibody were generated by DNA synthesis and PCR, then subsequently subcloned into plasmids for protein expression in a mammalian cell system. The gene sequences in the expression vectors were confirmed by DNA sequencing. Antibodies were then purified by a two-step affinity chromatography (Protein A) and size-exclusion chromatography process.

Example 4: Determination of Antibody Affinity to IL-23

Binding affinities ($K_D$) of antibodies to human IL-23 (generated as described in Examples 1-3) were determined through surface plasmon resonance (SPR) using a BIA-CORE™ 8K SPR system (Cytiva). Series S Sensor Chip CM5 (Cytiva) sensor chips were prepared by immobilizing goat anti-human IgG (Jackson ImmunoResearch) and ultimately used to determine the binding kinetic rate and affinity constants at 25° C. and in a running buffer of HBS-P+ (10 mM HEPES pH 7.4, 150 mM NaCl, 0.05% Surfactant P20). Anti-IL23 mAb constructs (diluted to 2 µg/mL) were captured onto flow cell 2 (active) for 60 sec at a flow rate of 10 µL/min. Recombinant Human IL-23 was prepared at concentrations of 0, 1.23, 3.7, 11.11, 33.33, 100 nM and injected over flow cell 1 (reference) and flow cell 2 (active) for 180 sec at a flow rate of 50 µL/min. Samples were injected in a multi-cycle manner over freshly captured mAb, by regenerating the capture surfaces with injection of 10 mM glycine, pH 1.5 for 30 sec at a flow rate of 30 µL/min. A 1:1 kinetic binding model was utilized to determine the apparent association (ka) and dissociation rate constants (kd). Their ratio provides the apparent equilibrium dissociation constant or affinity constant ($K_D$=kd/ka). Results for clones of interest are shown in Table 5.

Under the conditions tested, the kd (and thus $K_D$) of the reference antibody and the tested clones were not able to be determined, as the limit of detection of BIACORE™ 8K SPR is $1\times10^{-6}$ l/s (both antibodies tested had dissociation rates below this limit).

The strength of the interaction between the antigen-binding site and the epitope can be measured by the equilibrium association constant, ka. ka is the amount of antibody-antigen complex that exists at equilibrium.

Table 5 shows optimization of affinity of the clones of interest: Mab001 and Mab003 have a comparable ka as Reference Antibody 1; Mab002 and Mab004 have a higher ka as Reference Antibody 1.

TABLE 5

| Antibody | hIL-23 ka (1/Ms) | hIL-23 kd (1/s) | hIL-23 KD (nM) |
|---|---|---|---|
| Reference Antibody 1 | $1.67 \times 10^5$ | $<1 \times 10^{-6}$ | ND |
| Clone MAb001 | $1.51 \times 10^5$ | $<1 \times 10^{-6}$ | ND |
| Clone MAb003 | $1.64 \times 10^5$ | $<1 \times 10^{-6}$ | ND |
| Clone MAb002 | $2.66 \times 10^5$ | $<1 \times 10^{-6}$ | ND |
| Clone MAb004 | $2.47 \times 10^5$ | $<1 \times 10^{-6}$ | ND |

Example 5: Inhibition of IL-23-Induced Activation of STAT3 in HEK 293F IL-23R+/IL 12Rβ1+STAT3 Luciferase Reporter Cells Inhibition of STAT3 activation in HEK 293F cells expressing IL-23R, IL-12Rβ1, and a STAT3-linked luciferase reporter was used to evaluate the functional activity of antibodies (generated as described in Examples 1-3) to block IL-23-induced biological activity. Briefly, reporter cells were seeded into a 96-well plate. A mixture of hIL-23 and purified IL-23 antibodies were allowed to associate for 30 min at room temperature before adding to cells, resulting in a final concentration of 20 ng/ml of hIL-23 and 0-50 nM of antibody. Cells were incubated at 37° C. for 5 hours and subsequently lysed with One-Glo luciferase assay buffer (Promega) at room temperature for 10 min under dark conditions. Luminescence was quantified by a SpectraMax® M5e plate reader (Molecular Devices) and subsequent data were analyzed using GraphPad Prism. $IC_{50}$ values were determined as the concentration of antibody required to inhibit 50% of the maximum luminescent signal detected with incubation of 20 ng/ml of hIL-23 alone.

As shown in Table 6, the tested clones demonstrated more effective inhibition of IL-23-induced activation of STAT3 as compared to the Reference Antibody 1.

TABLE 6

| Antibody | Relative $IC_{50}$ |
|---|---|
| Reference antibody 1 | 1.000 |
| Clone MAb001 | 0.612 |
| Clone MAb003 | 0.868 |
| Clone MAb002 | 0.640 |
| Clone MAb004 | 0.409 |
| Values relative to Reference Antibody 1. | <1.000 is more potent. |

Example 6. Inhibition of IL-23-Induced Phosphorylation of STAT3 in DB Cells

Inhibition of STAT3 phosphorylation in DB cells was used to evaluate the functional activity of antibodies to block IL-23-induced biological activity. Briefly, $6\times10^5$ DB cells were seeded into TC-treated round-bottom 96-well plates. A mixture of hIL-23 and purified IL-23 antibodies were allowed to associate for 1 hr at room temperature before adding to cells, resulting in a final concentration of 25 ng/mL of hIL-23 and 0-10 nM of antibody. Cells were incubated at 37° C. for 1 hr and phosphorylated STAT3 (pSTAT3) was quantified using a pSTAT3 Sandwich ELISA kit (Cell Signaling Technology). Subsequent data were analyzed using GraphPad Prism. $IC_{50}$ values were determined as the concentration of antibody required to inhibit 50% of the maximum pSTAT levels detected with incubation of 25 ng/mL of hIL-23 alone.

As shown in Table 7, the affinity matured clones demonstrated more effective inhibition of IL-23-induced phosphorylation of STAT3 as compared to the Reference Antibody 1.

TABLE 7

| Antibody | Relative $IC_{50}$ |
|---|---|
| Reference Antibody 1 | 1.000 |
| Clone MAb001 | 0.573 |
| Clone MAb003 | 0.799 |
| Values relative to Reference Antibody 1. | <1.000 is more potent. |

Example 7. Pharmacokinetic (PK) Analysis of IL-23p19 Binding Proteins in Cynomolgus Monkeys In order to evaluate the impact of half-life extension mutations on IL-23p19 binding protein pharmacokinetics (PK), male cynomolgus monkeys (*Macaca fascicularis*) ranging from 2.4 to 3.4 kg in weight were administered a single bolus dose (5 mg/kg) of the reference antibody described in Example 1 (Reference Antibody 1, see sequences in Table 3 above) containing Fc LALA mutations with and without Fc YTE mutations (see SEQ ID NOs: 51 and 55, respectively in Table 2) by either intravenous (IV) and/or subcutaneous (SC) injection on Day 0. Serum samples were taken regularly through the study.

Figure 2:
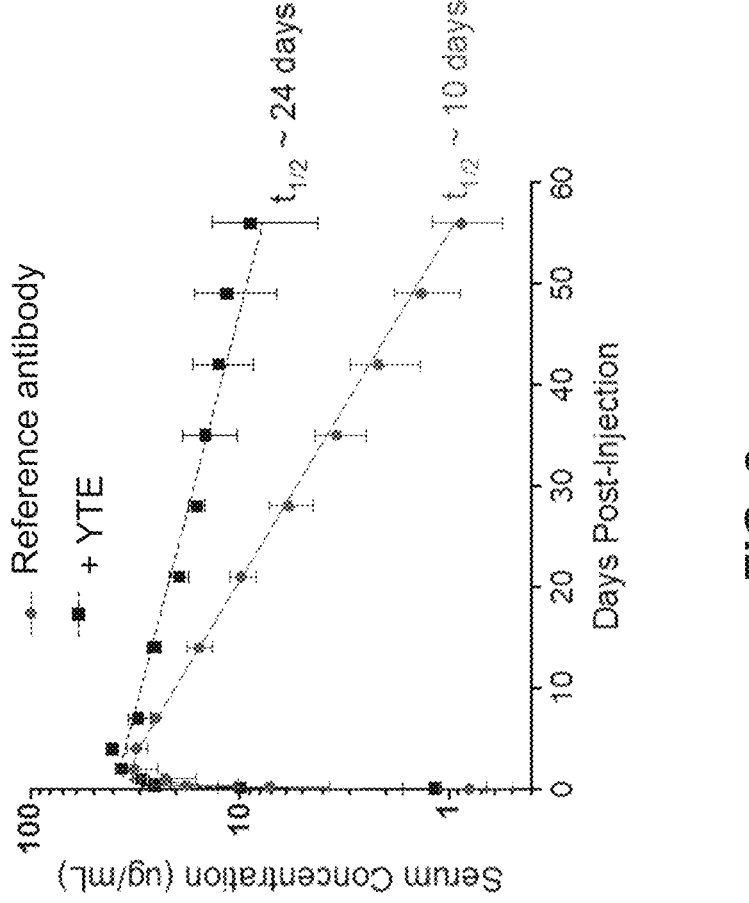
FIG. 2 is a graph of serum concentration in μg/mL (y-axis) plotted against days post-injection (x-axis) in cynomolgus monkeys subcutaneously administered a single bolus dose (5 mg/kg) of an IL-23p19 binding protein with ("+YTE") or without ("reference antibody") Fc YTE mutations (Reference Antibody 1). See Example 7.

Half-life was determined from cynomolgus serum samples for each dose-cohort up to day 56, with average PK curves shown in FIG. 1 for IV administration and FIG. 2 for SC administration. The β-elimination half-life of IL-23p19 binding proteins with Fc YTE mutations was observed to be 30 days and 24 days for IV and SC dosing, respectively. In contrast, the observed half-life of the Reference Antibody 1 (without Fc YTE mutations) was 11 days and 10 days for IV and SC dosing, respectively.

Scaling of the observed half-life in cynomolgus monkey of IL-23p19 binding protein with YTE modifications led to a human half-life projection of 74-93 days.

Therefore, the present example demonstrates enhanced half-life of an IL-23p19 binding protein having a half-life extending mutations in the Fc region.

Example 8. Pharmacokinetic Modeling and Simulation of Potential Clinical Dosing Regimens Pharmacokinetic modeling and simulation were utilized in order to identify potential clinical dosing regimens that would maintain serum concentration of IL-23p19 binding proteins above a specific level at a given time during the regimen or at steady state. Achieving these thresholds has been demonstrated to translate into better responses and patient outcomes in relevant indications.

A two compartment linear model with parameters for central volume of distribution ($V_c$), peripheral volume of distribution ($V_p$), clearance from the central volume (CL), first-order absorption rate constant from a subcutaneous depot into the central volume ($k_a$), and subcutaneous bioavailability (F) relative to the intravenous administration was used to identify dosing regimens. Given the results from the PK analysis in cynomolgus monkey described in Example 4, an IL-23p19 binding protein with YTE may be expected to have a longer serum half-life than normal IgG. Therefore, the effective half-life used in these simulations was 74 days, in line with the lower end of projections based on the cynomolgus monkey PK study.

Figure 3:
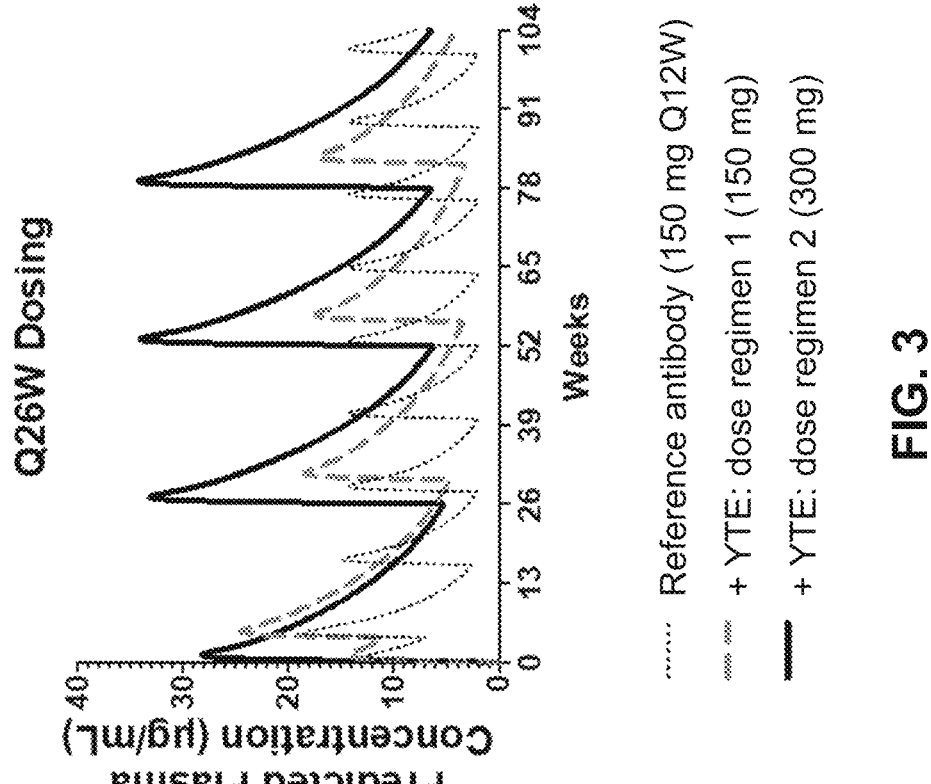
FIG. 3 is a graph of predicted plasma concentrations in μg/mL (y-axis) plotted against days post-injection (x-axis) for an IL-23p19 binding protein dosing regimen which includes an induction regimen and subsequent dosing every 6 months (e.g., 26 weeks) based on pharmacokinetic modeling and simulation experiments described in Example 8. Shown are the predicted plasma concentration curves for an IL-23p19 binding protein with YTE mutations ("+YTE") ($t_{1/2}$=74 days) dosed at 150 mg at weeks 0 and 4 and every 26 weeks thereafter ("dose regimen 1 (150 mg)") or at 300 mg at week 0 and every 26 weeks thereafter ("dose regimen 2 (300 mg)"). For comparison, also shown are predicted plasma concentration curves for an IL-23p19 binding protein Reference Antibody 1 ("Reference antibody") without any half-life extending mutations ($t_{1/2}$=28 days) dosed at 150 mg at weeks 0 and 4 and every 12 weeks thereafter.
Figure 4:
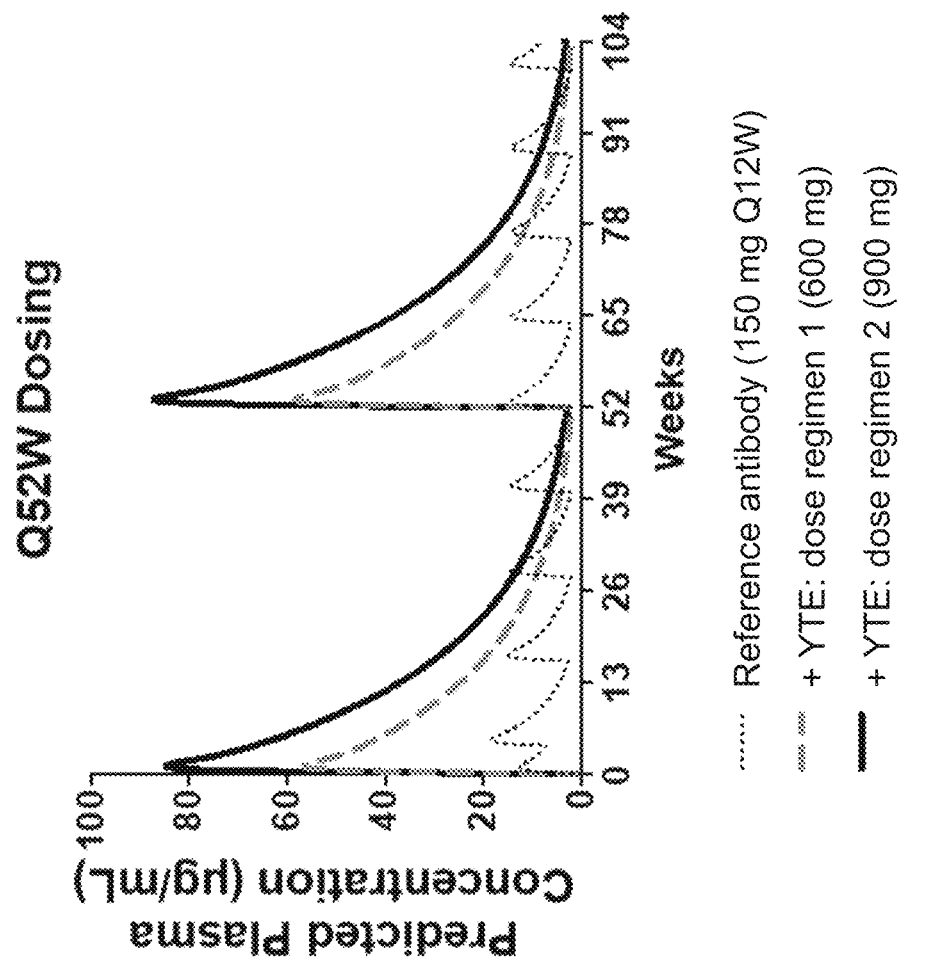
FIG. 4 is a graph of predicted plasma concentrations in µg/mL (y-axis) plotted against days post-injection (x-axis) for an IL-23p19 binding protein dosing regimen which includes an induction regimen and subsequent dosing every year (e.g., 52 weeks) based on pharmacokinetic modeling and simulation experiments described in Example 8. Shown are the predicted plasma concentration curves for an IL-23p19 binding protein with YTE mutations ("+YTE") ($t_{1/2}$=74 days) dosed at 600 mg at week 0 and every 52 weeks thereafter ("dose regimen 1 (600 mg)") or at 900 mg at week 0 and every 52 weeks thereafter (("dose regimen 2 (900 mg)"). For comparison, also shown are predicted plasma concentration curves for an IL-23p19 binding protein Reference Antibody 1 without any half-life extending mutations ("Reference antibody") ($t_{1/2}$=28 days) dosed at 150 mg at weeks 0 and 4 and every 12 weeks thereafter.

In order to achieve optimal patient outcomes, subcutaneous dosing regimens which achieved an average concentration from week 0-16 ($C_{avg;\ W0\text{-}16}$) of 16.0 μg/mL or higher and a trough concentration at steady state ($C_{trough;\ SS}$) of 2.0 μg/mL or higher were identified (Table 8). Based on these simulations, IL-23p19 binding proteins with a half-life of 74 days can be dosed subcutaneously with a maintenance frequency of every 6 months, e.g., every 26 weeks (FIG. 3) or every year (e.g., every 12 months or every 52 weeks) (FIG. 4) and maintain clinically relevant serum concentrations.

TABLE 8

| Induction Regimen | Maintenance Frequency | Dose (mg) |
|---|---|---|
| Week 0, Week 4 | Every 26 weeks | 150 |
| Week 0 | Every 26 weeks | 300 |
| Week 0 | Every 52 weeks | 600, 900, 1200 |

Example 9. Characteristics of Anti-IL-23 Antibody MAb002

The cytokine IL-23 is secreted by activated macrophage and dendritic cells (DC) and promotes the expansion and/or activity of Th17 cells, CD8+ T cells, macrophages, and DCs. Its pathogenic role in IBD is suggested by genetic association and has been confirmed in clinical trials, demonstrating IL-23 antagonism as an effective and safe treatment for Crohn's disease (CD) and ulcerative colitis (UC).

MAb002 is a novel, extended half-life humanized IgG1 monoclonal antibody (mAb) that binds IL-23. This Example evaluates the characteristics of MAb002. In particular, MAb002 binds specifically to IL-23 with picomolar affinity. It inhibits STAT3 activity and phosphorylation with $IC_{50}$ values<1 nM, as well as IL-17 secretion in IL-23-stimulated mouse splenocytes and human PBMC. IL-23 binding potency and $IC_{50}$ values for IL-23 antagonism are comparable to those of two different reference antibodies, Reference Antibody 1 (see Table 3 in Example 1), and Reference Antibody 2, whose characteristic sequences are shown in Table 9 below.

TABLE 9

| Reference Antibody 2 - characteristic sequences CDR sequences shown are according to Kabat. | |
|---|---|
| Heavy chain variable domain | Light chain variable domain |
| EVQLVQSGAEVKKPGESLKISCKGSGYSFSNY WIGWVRQMPGKGLEWMGIIDPSNSYTRYSPSF QGGQVTISADKSISTAYLQWSSLKASDTAMYYC ARWYYKPFDVWGQGTLVTVSS (SEQ ID NO: 157) CDR-H1: NYWIG (SEQ ID NO: 159) CDR-H2: IIDPSNSYTRYSPSFQG (SEQ ID NO: 160) CDR-H3: WYYKPFDV (SEQ ID NO: 161) | QSVLTQPPSVSGAPGQRVTISCTGSSSNIGSGY DVHWYQQLPGTAPKLLIYGNSKRPSGVPDRFSG SKSGTSASLAITGLQSEDEADYYCASWTDGLSL VVFGGGTKLTVL (SEQ ID NO: 158) CDR-L1: TGSSSNIGSGYDVH (SEQ ID NO: 162) CDR-L2: GNSKRPS (SEQ ID NO: 163) CDR-L3: ASWTDGLSLVV (SEQ ID NO: 164) |

Cryo-EM demonstrates the binding epitope of MAb002 is within IL-23. The half-life of MAb002 is significantly extended in cynomolgus monkeys compared to both Reference Antibody 1 and Reference Antibody 2. Based on allometric scaling of the clearance of Mab002 observed in this study, predictive simulations of MAb002 pharmacokinetics in humans suggest that subcutaneous dosing at intervals once every three months or longer, e.g., between once every three months and once every six months, or even longer intervals (Q3M-Q6M+) will achieve therapeutic exposures in patients across a wide range of body weights and albumin concentrations.

Materials and Methods

MAb002 was evaluated in multiple in vitro and ex vivo assays compared to a reference anti-IL-23 antibody. Binding affinity to IL-23 was determined by surface plasmon resonance (SPR) and kinetic exclusion assays (KinExA). Antagonism of IL-23 signaling was measured via a STAT3 reporter cell line and phospho-STAT3 ELISA. Antibody-induced reduction of IL-17 secretion in response to human IL-23 was assessed in mouse splenocytes and human peripheral blood mononuclear cells (PBMC). The binding epitope of the Reference Antibody 1 and MAb002 to IL-23 was determined using cryogenic electron microscopy. Half-life extension was measured via pharmacokinetic analysis in cynomolgus monkeys given a single bolus of MAb002 and Reference Antibody 1 by intravenous and/or subcutaneous (SC) administration.

Results

Figure 5B:
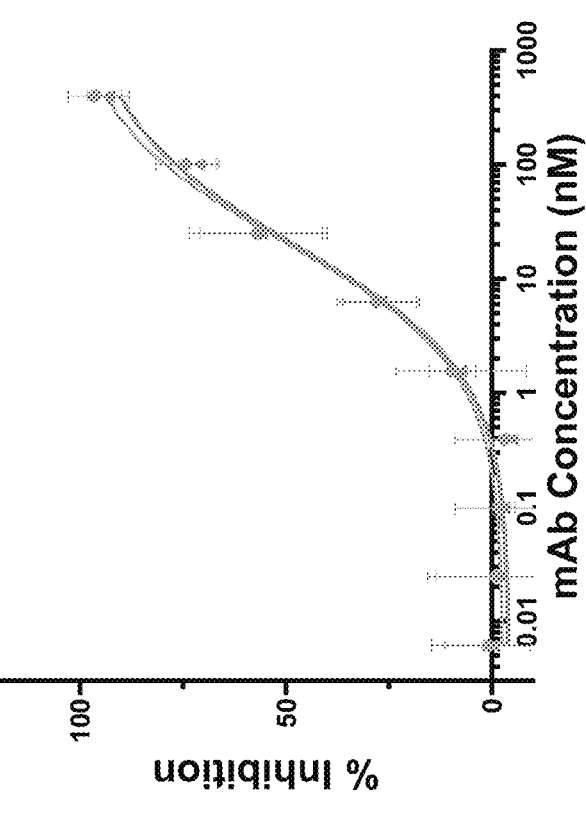
FIG. 5B depicts inhibition of IL-17 release by MAb002 and by Reference Antibody 1.
Figure 5A:
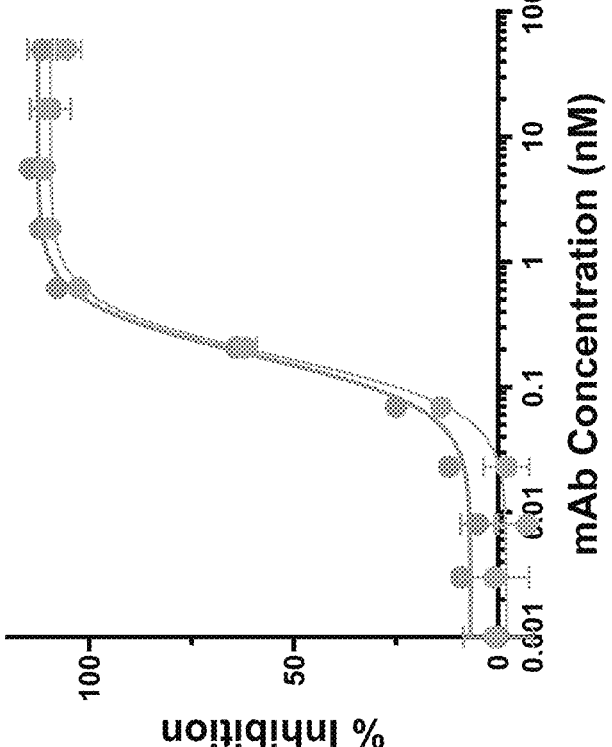
FIG. 5A depicts inhibition of pSTAT signaling by MAb002 and by a reference anti-IL-23 antibody ("Reference Antibody 1"; see Table 3 in Example 1).
Figure 6:
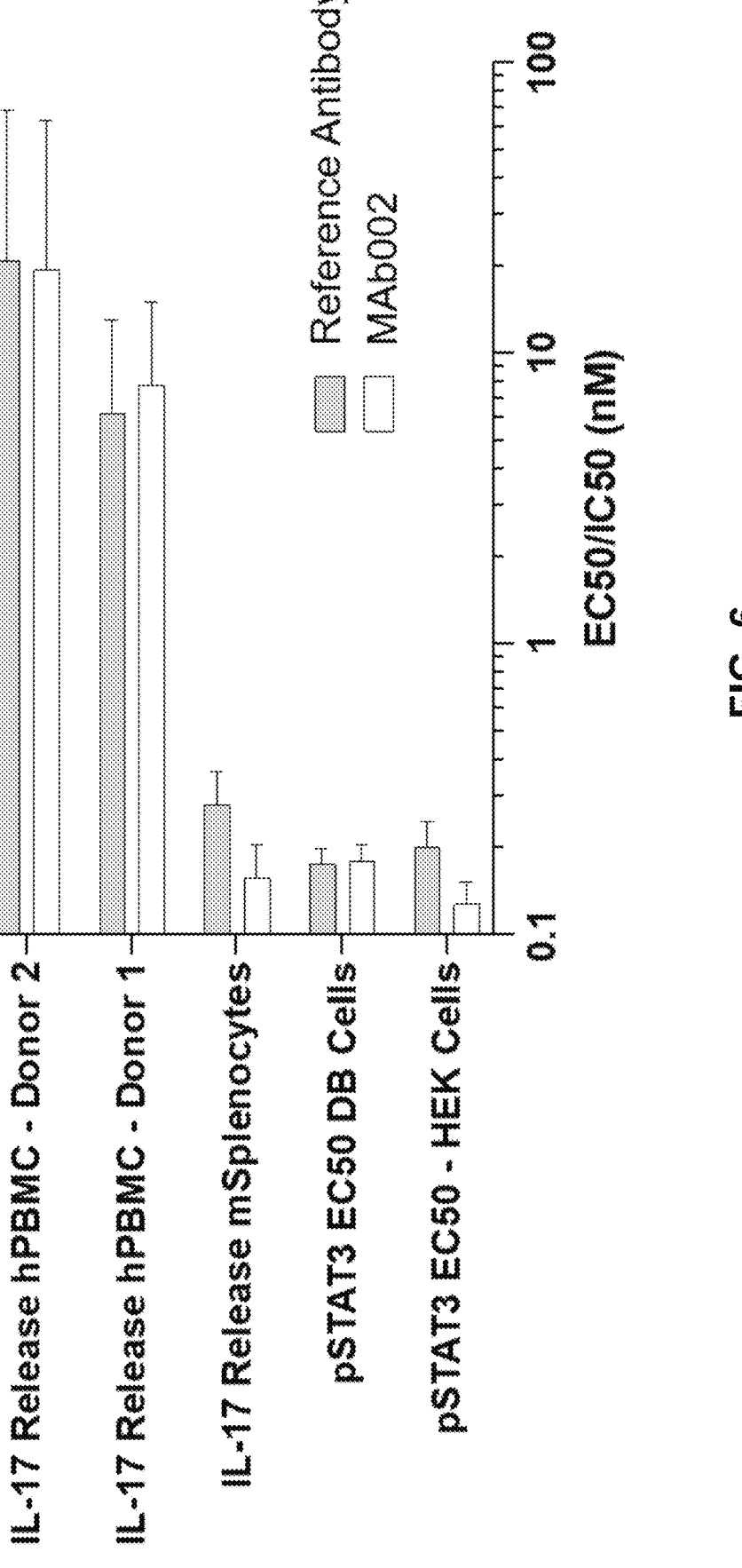
FIG. 6 depicts reduction of IL-17 release by human PBMCs and by murine splenocytes stimulated with IL-23 and inhibition of pSTAT in DB and HEK cells by Reference Antibody 1 (gray bars) or by MAb002 (white bars).

MAb002 inhibits STAT3 activity and phosphorylation with $IC_{50}$ values<1 nM, as well as IL-17 secretion in IL-23-stimulated mouse splenocytes and human PBMC (FIG. 5A). IL-23 binding potency and IC values for IL-23 antagonism are comparable to those of the Reference Antibody 1 (FIG. 5B). MAb002 also inhibits IL-17 release after IL-23 stimulation in human PBMC and murine splenocytes about as effectively as the Reference Antibody 1 (FIG. 6). In addition, the $EC_{50}$ for suppression of pSTAT in DB and HEK cells was similar for both MAb002 and the Reference Antibody 1 (FIG. 6).

Figure 7:
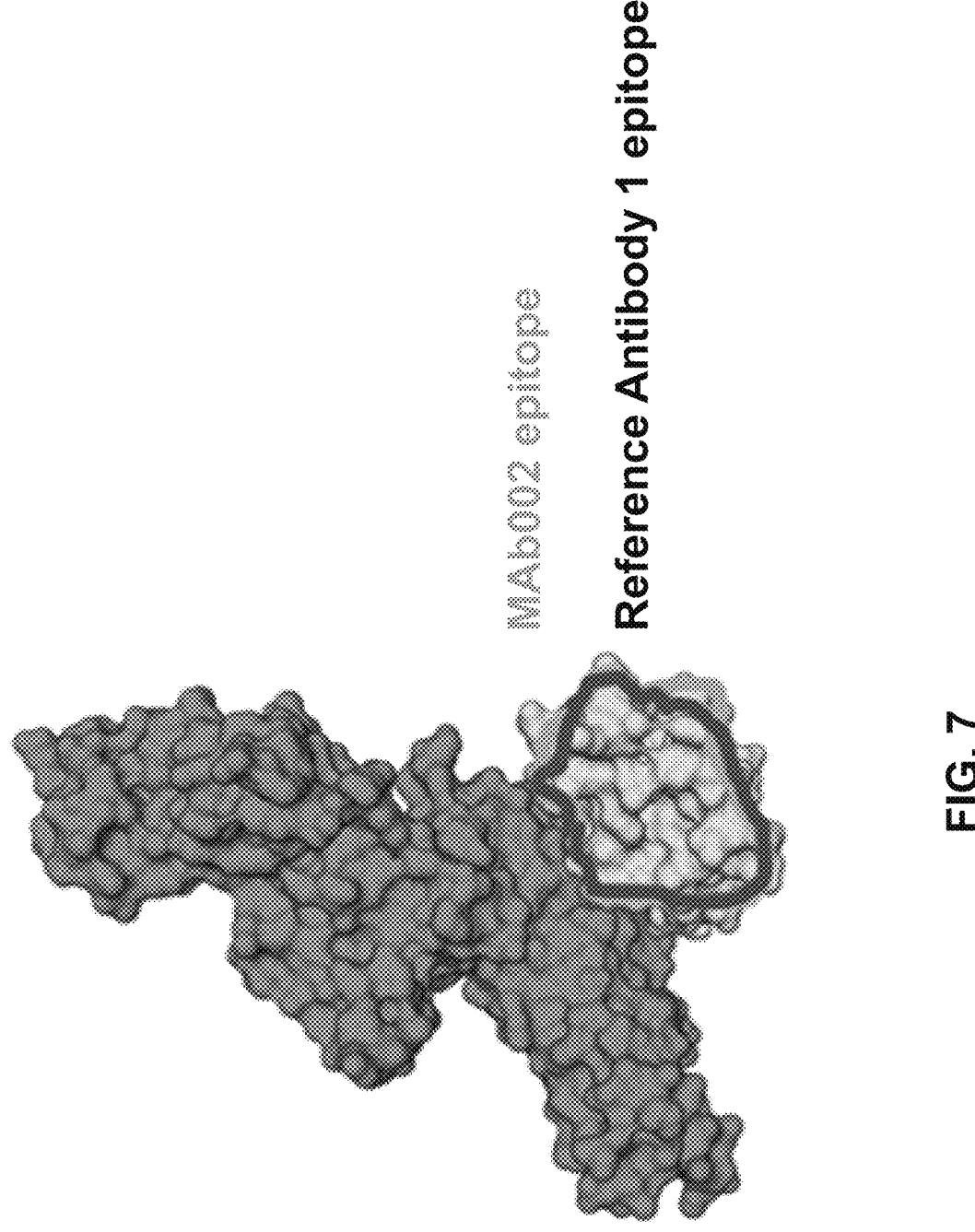
FIG. 7 shows the binding epitopes of Reference Antibody 1 and of MAb002 on IL-23 as determined by cryogenic electron microscopy (cryo-EM).

Cryo-EM demonstrates that MAb002 binds to a similar epitope on the p19 subunit of IL-23 as Reference Antibody 1 (FIG. 7).

Figure 8:
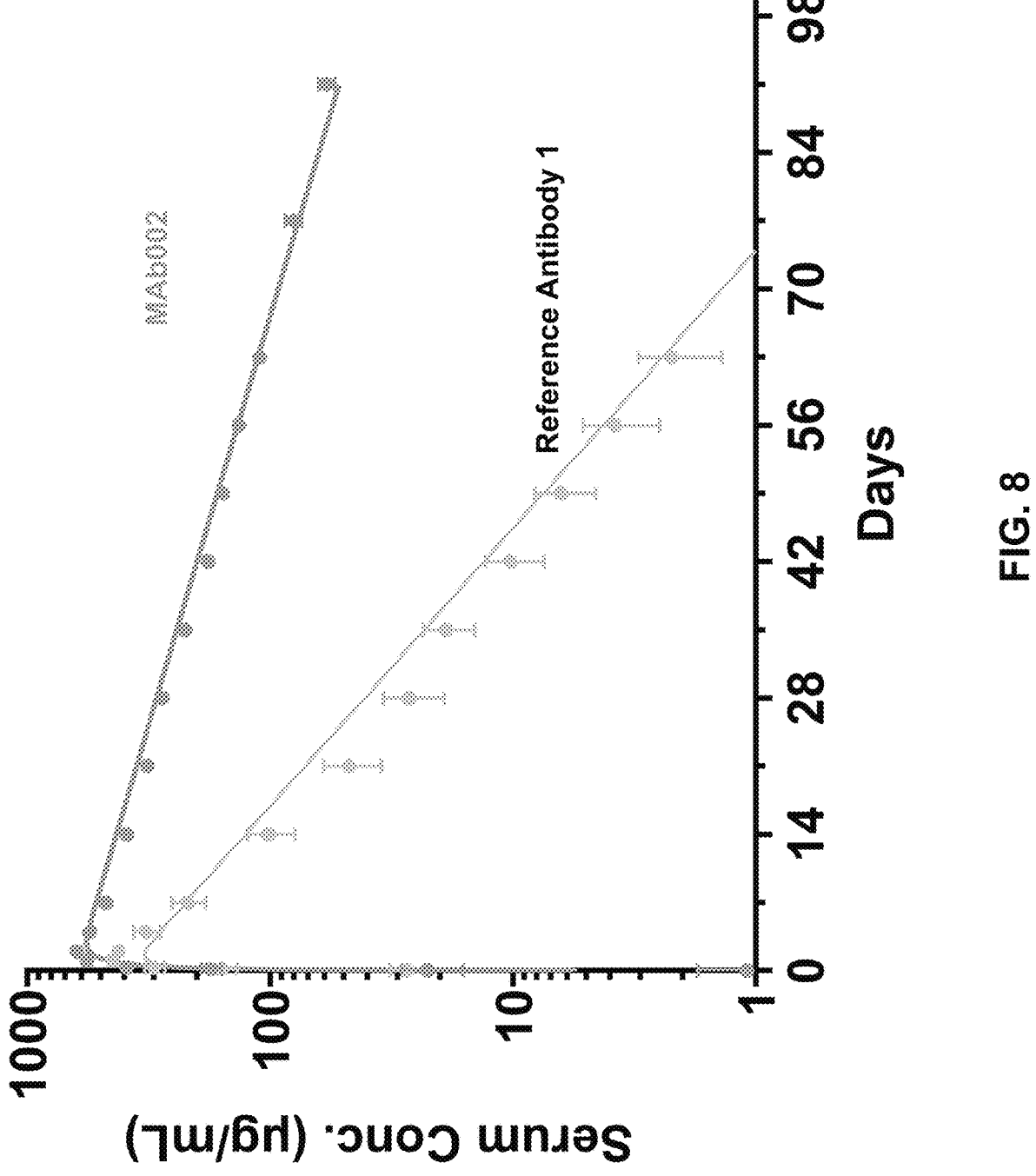
FIG. 8 depicts the half-life of MAb002 (upper curve) and the Reference Antibody 1 (lower curve) in non-human primates (cynomolgus monkeys).
Figure 9:
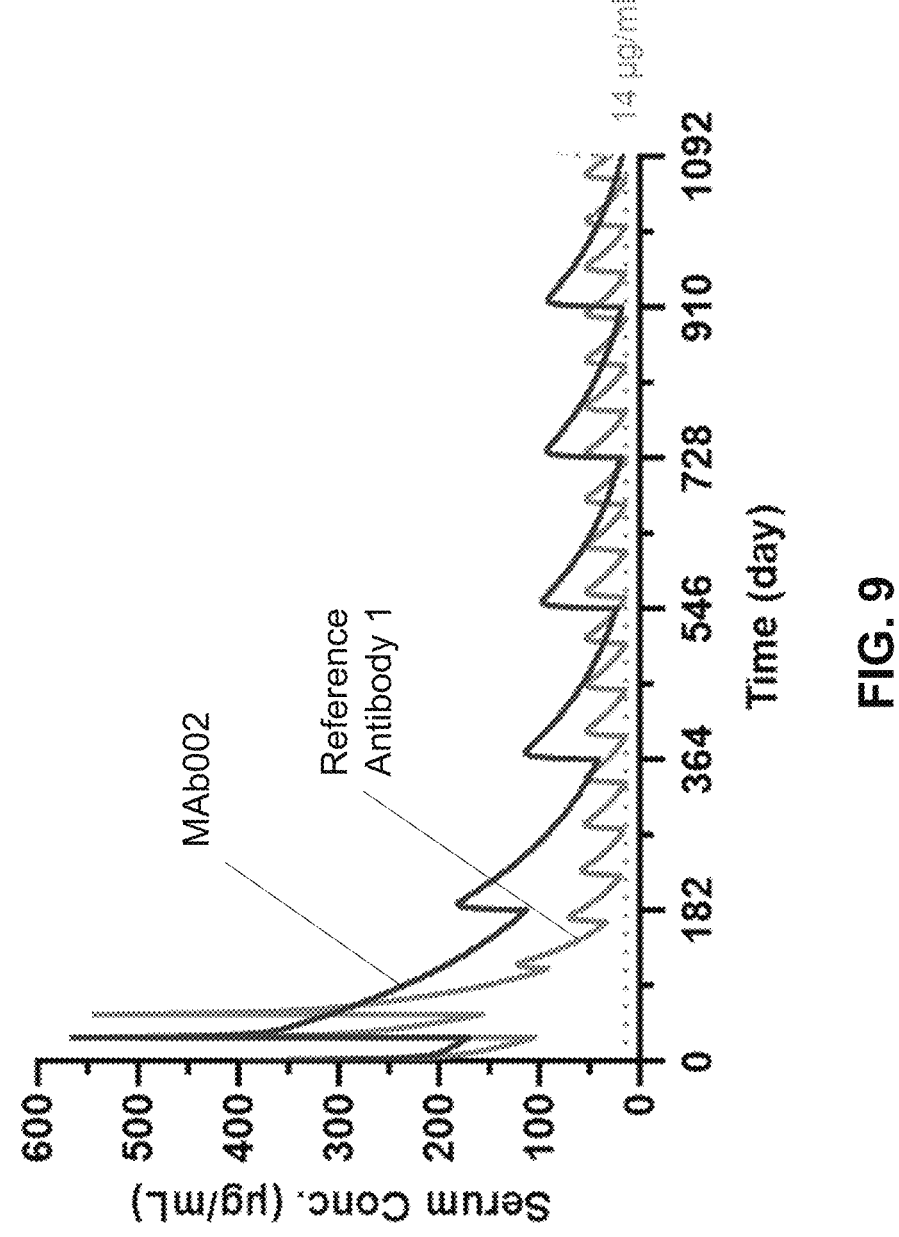
FIG. 9 depicts predictive simulations of MAb002 (darker line) and Reference Antibody 1 (lighter line) pharmacokinetics in humans. MAb002 was modeled based on a half-life of 90 days with 1200 mg intravenous administration at weeks 0 and 4 followed by 600 mg subcutaneous administration every 26 weeks (Q26W). Reference Antibody 1 was modeled based on a half-life of 28 days with 1200 mg intravenous administration at weeks 0, 4, and 8 followed by 360 mg subcutaneous administration every 8 weeks (Q8W).
Figure 10A:
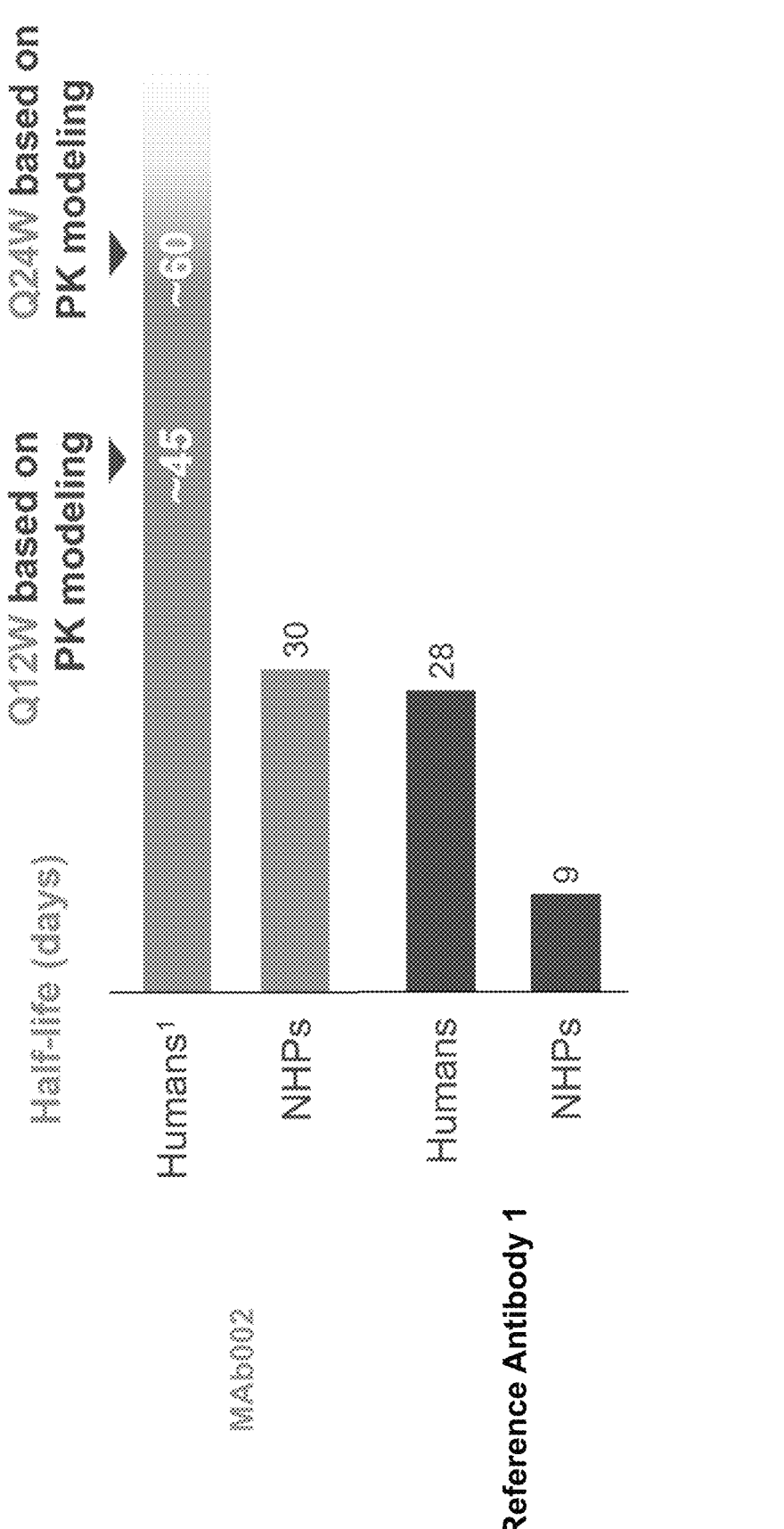
FIG. 10A is a graph showing human half-lives (in days) as predicted by non-human primate (NHP) data for MAb002 and Reference Antibody 1 and based on an average Mab002 half-life that is about 3 times greater than average Reference Antibody 1 half-life.
Figure 10B:
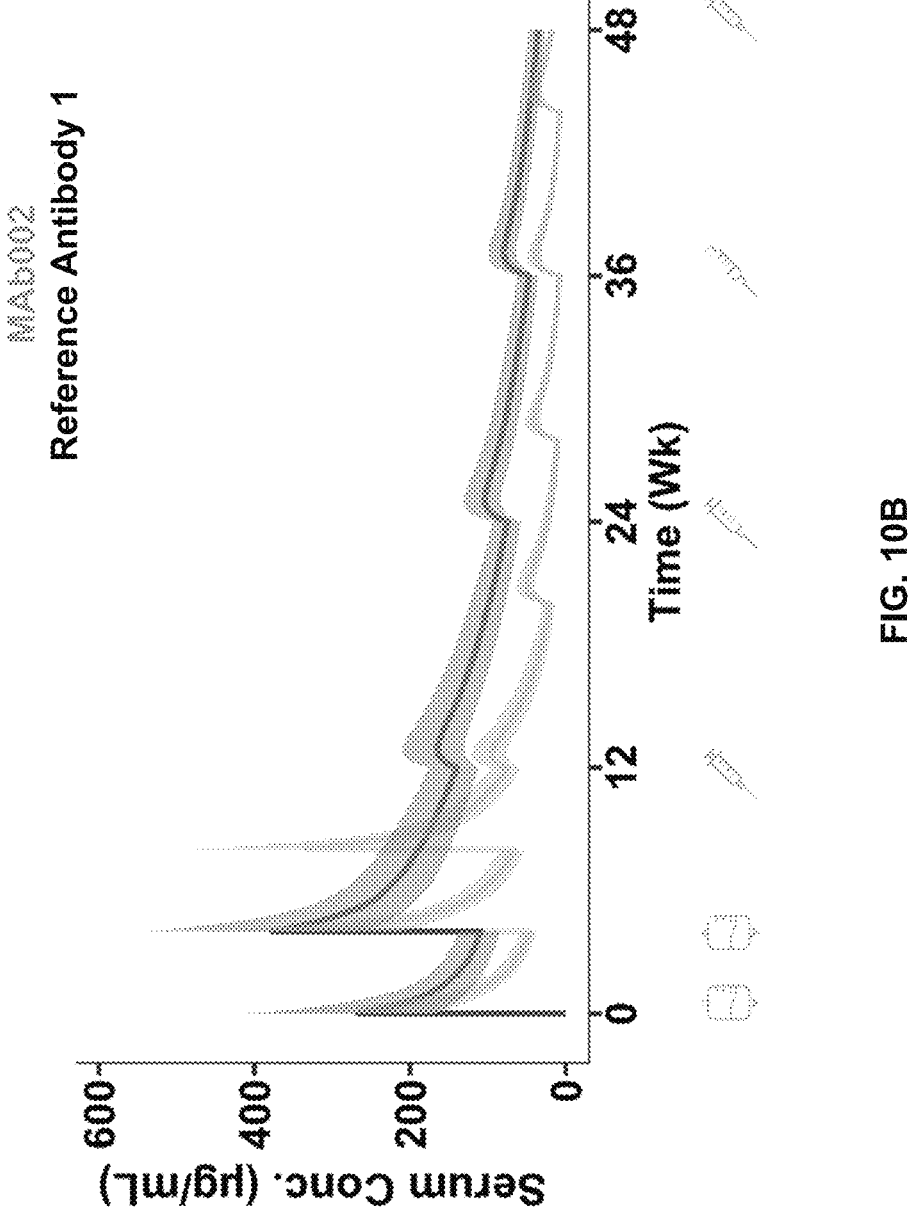
FIG. 10B depicts predictive simulations of MAb002 (darker line, intravenous administration at weeks 0 and 4 followed by subcutaneous administration at 12 weeks and every 12 weeks (Q12W)) and Reference Antibody 1 (lighter line, intravenous administration at weeks 0, 4 and 8 followed by subcutaneous administration every 8 weeks (Q8W)) pharmacokinetics in humans based on an average Mab002 half-life that is about 3 times greater than average Reference Antibody 1 half-life. Lines show the simulated median; shaded area shows the IQR. Stochastic simulations: n=2,000 virtual subjects.

The half-life of MAb002 is extended in cynomolgus monkeys about 3-times compared to the reference antibody (FIG. 8, about 30 days for Mab002 vs. about 9 days for Reference Antibody 1). Based on allometric scaling of the clearance of MAb002 and the reference antibody observed in this study, predictive simulations of MAb002 PK in humans suggest that Q3M-Q6M+ subcutaneous (SC) dosing will achieve therapeutic exposures in patients across a wide range of body weights and albumin concentrations in comparison to a Q2M dosing frequency of the Reference Antibody 1 (FIG. 9, FIG. 10A, and FIG. 10B).

Conclusions

MAb002 exhibits high selectivity and affinity for IL-23 and potently inhibits downstream cellular signaling. With an extended half-life in NHP, MAb002 demonstrates therapeutic potential for effective and safe treatment of Crohn's disease and ulcerative colitis with the potential advantage of twice a year subcutaneous dosing. Further preclinical and clinical studies may further demonstrate this potential.

EQUIVALENTS

The entire disclosure of each of the patent documents and scientific articles referred to herein is incorporated by reference for all purposes.

The disclosure may be embodied in other specific forms without departing from the spirit or essential characteristics thereof. The foregoing embodiments are therefore to be considered in all respects illustrative rather than limiting the disclosure described herein.

Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

What is claimed is:

1. An IL-23 binding protein comprising:
   (a) a heavy chain variable domain (VH), the VH comprising:
      an amino acid sequence that is at least 85% identical to that of SEQ ID NO: 28, and an asparagine at position 74 of SEQ ID NO: 28; and
      complementarity-determining regions CDR-H1 comprising the amino acid sequence of SEQ ID NO: 30, CDR-H2 comprising the amino acid sequence of SEQ ID NO: 31, and CDR-H3 comprising the amino acid sequence of SEQ ID NO: 32;
   and
   (b) a light chain variable domain (VL), the VL comprising:
      an amino acid sequence that is at least 85% identical to that of SEQ ID NO: 29, and a phenylalanine at position 49 of SEQ ID NO: 29; and
      complementarity-determining regions CDR-L1 comprising the amino acid sequence of SEQ ID NO: 6, CDR-L2 comprising the amino acid sequence of SEQ ID NO: 7, and CDR-L3 comprising the amino acid sequence of SEQ ID NO: 8.

2. The IL-23 binding protein of claim 1, wherein the VH comprises one or more of the following: glutamic acid at position 1, leucine at position 5, glutamic acid at position 6, glycine at position 9, glycine at position 10, leucine at position 11, valine at position 12, glutamine at position 13, glycine at position 16, leucine at position 18, arginine at position 19, leucine at position 20, alanine at position 23, valine at position 37, lysine at position 43, arginine at position 67, leucine at position 70, serine at position 71, alanine at position 68, lysine at position 76, asparagine at position 77, leucine at position 81, glutamine at position 82, methionine at position 83, asparagine at position 84, alanine at position 88, or threonine at position 115 of SEQ ID NO: 28.

3. The IL-23 binding protein of claim 1, wherein the VL comprises one or more of the following: glutamic acid at position 1, valine at position 3, alanine at position 9, threonine at position 10, valine at position 13, proline at position 15, glutamic acid at position 17, alanine at position 19, leucine at position 21, serine at position 22, glutamine at position 42, alanine at position 43, arginine at position 45, leucine at position 48, isoleucine at position 58, alanine at position 60, glutamic acid at position 70, serine at position 80, phenylalanine at position 83, valine at position 85, tyrosine at position 87, glycine at position 100 or valine at position 104 of SEQ ID NO: 29.

4. The IL-23 binding protein of claim 1, wherein the VH comprises an amino acid sequence that is at least 95% identical to that of SEQ ID NO: 28, and the VL comprises an amino acid sequence that is at least 95% identical to that of SEQ ID NO: 29.

5. The IL-23 binding protein of claim 1, wherein the VH comprises an amino acid sequence that is at least 98% identical to that of SEQ ID NO: 28, and the VL comprises an amino acid sequence that is at least 98% identical to that of SEQ ID NO: 29.

6. The IL-23 binding protein of claim 1, wherein the VH comprises the amino acid sequence of SEQ ID NO: 28, and the VL comprises the amino acid sequence of SEQ ID NO: 29.

7. The IL-23 binding protein of claim 1, wherein upon contacting human embryonic kidney (HEK) cells expressing IL-23R, the IL-23 binding protein inhibits activation of STAT3 in HEK at a relative $IC_{50}$ of less than 0.9, less than 0.8, less than 0.7, or from about 0.6 to about 0.7, wherein the relative $IC_{50}$ refers to a ratio of an $IC_{50}$ value of the IL-23 binding protein relative to the $IC_{50}$ of a reference antibody that comprises a VH sequence of SEQ ID NO: 156 and a VL sequence of SEQ ID NO: 2.

8. The IL-23 binding protein of claim 1, wherein the IL-23 binding protein is a humanized antibody or antigen-binding fragment thereof and the antibody or antigen binding fragment thereof comprises an Fc region.

9. The IL-23 binding protein of claim 8, wherein the Fc region is a modified Fc region, wherein the modified Fc region comprises a half-life extending modification or set of modifications.

10. The IL-23 binding protein of claim 9, wherein the modified Fc region comprises amino acid modifications M252Y, S254T, and T256E (YTE) and/or M428L and N434S (LS) according to EU numbering system.

11. The IL-23 binding protein of claim 1, comprising:
   (a) a heavy chain comprising an amino acid sequence that is at least 95% identical to that of SEQ ID NO: 171; and
   (b) a light chain comprising an amino acid sequence that is at least 95% identical to that of SEQ ID NO: 172.

12. An isolated nucleic acid encoding the IL-23 binding protein of claim 1.

13. An expression vector comprising the isolated nucleic acid of claim 12.

14. A host cell comprising the isolated nucleic acid of claim 12.

15. A host cell comprising the expression vector of claim 13.

16. A composition comprising an IL-23 binding protein, and a pharmaceutically acceptable carrier,
   wherein the IL-23 binding protein comprises:
   (a) a heavy chain variable domain (VH), the VH comprising:
      an amino acid sequence that is at least 85% identical to that of SEQ ID NO: 28, and an asparagine at position 74 of SEQ ID NO: 28; and
      complementarity-determining regions CDR-H1 comprising the amino acid sequence of SEQ ID NO: 30, CDR-H2 comprising the amino acid sequence of SEQ ID NO: 31, and CDR-H3 comprising the amino acid sequence of SEQ ID NO: 32;
   and
   (b) a light chain variable domain (VL), the VL comprising:
      an amino acid sequence that is at least 85% identical to that of SEQ ID NO: 29, and a phenylalanine at position 49 of SEQ ID NO: 29; and
      complementarity-determining regions CDR-L1 comprising the amino acid sequence of SEQ ID NO: 6, CDR-L2 comprising the amino acid sequence of SEQ ID NO: 7, and CDR-L3 comprising the amino acid sequence of SEQ ID NO: 8.

17. A method of treating an inflammatory condition in a subject in need thereof, comprising a step of administering to the subject an effective amount of the composition of claim 16.

18. The method of claim 17, wherein the effective amount of the composition is administered subcutaneously or intravenously.

19. A method of treating a gastrointestinal inflammatory disease in a subject in need thereof, comprising a step of administering subcutaneously or intravenously to the subject an effective amount of the composition of claim 16.

20. The method of claim 19, wherein the gastrointestinal inflammatory disease is Crohn's disease or ulcerative colitis.

*   *   *   *   *